United States Patent [19]
Bigge et al.

[11] Patent Number: 5,721,234
[45] Date of Patent: Feb. 24, 1998

[54] GLUTAMATE RECEPTOR ANTAGONISTS: FUSED CYCLOALKYLOUINOXALINEDIONES

[75] Inventors: Christopher Franklin Bigge, Ann Arbor; Daniel Martin Retz, Ypsilanti, both of Mich.

[73] Assignee: Warner-Lambert Company, Morris Plains, N.J.

[21] Appl. No.: 534,526

[22] Filed: Oct. 23, 1995

Related U.S. Application Data

[63] Continuation-in-part of Ser. No. 350,765, Dec. 7, 1994, abandoned.

[51] Int. Cl.[6] ............ C07D 241/38; C07D 401/12; C07D 405/12; A61K 31/495
[52] U.S. Cl. ............ 514/250; 544/344; 562/433; 562/434; 552/8; 564/218; 560/20; 560/21
[58] Field of Search ............... 514/250; 544/344

[56] References Cited

U.S. PATENT DOCUMENTS

| | | | |
|---|---|---|---|
| 4,889,855 | 12/1989 | Jacobsen et al. | 514/250 |
| 5,081,123 | 1/1992 | Honoré et al. | 514/250 |
| 5,308,845 | 5/1994 | Honoré et al. | 514/250 |
| 5,389,687 | 2/1995 | Schaus et al. | 574/657 |

FOREIGN PATENT DOCUMENTS

| | | |
|---|---|---|
| 0283959/A1 | 9/1988 | European Pat. Off. |
| 488959 | 6/1992 | European Pat. Off. |

OTHER PUBLICATIONS

K. Lippert et al., Eur. J. Pharmacol. 253 (3), 207–13 (1994).
W. Loescher et al., Eur. J. Neurosci. 5(11), 1545–50 (1993).
J. Mosinger et al., Exp. Neurol. 113, 10–17 (1991).
C.F. Bigge and T.C. Malone, Curr. Opin. Ther. Pat., 951 (1993).
M. A. Rogawski, TiPS 14, 325 (1993).
H. Li and A.M. Buchan, J. Cerebr. Blood Flow Metab. 13, 933 (1993).
B. Nellgard and T. Wieloch, J. Cerebr. Blood Flow Metab. 12, 2 (1992).
R. Bullock et al., J. Cerebr. Blood Flow Metab. 14, 466 (1994).
D. Xue et al., J. Cerebr. Blood Flow Metab. 14, 251 (1994).
X.-J. Xu et al., J. Pharmacol. Exp. Ther. 267, 140 (1993).
T. Namba et al., Brain Res. 638, 36 (1994).
S. E. Browne and J. McCulloch, Brain Res. 641, 10 (1994).
S.I. Yamaguchi et al., Epilepsy Res. 15, 179 (1993).
S.E. Smith et al., Eur. J. Pharmacol. 201, 179 (1991).
T. Klockgether et al., Ann Neurol. 34 (4), 585–593 (1993).
P.T. Francis et al., J. Neurochem. 60 (5), 1589–1604 (1993).
S. Lipton, TINS 16 (12), 527–532 (1993).
S. Lipton et al., New Eng. J. Med. 330 (9), 613–622 (1994).
C.F. Bigge, Biochem Pharmacol. 45, 1547–1561 (1993).
A.M. Buchan et al., Neurosci. Lett (Ireland) 132 (2), 255–8 (1991).
L. Dalgaard et al., Drug Metabolism and Disposition 22 (2), 289–93 (1994).

*Primary Examiner*—Mark L. Berch
*Attorney, Agent, or Firm*—Elizabeth M. Anderson

[57] ABSTRACT

Novel glutamate receptor antagonists represented by the formula

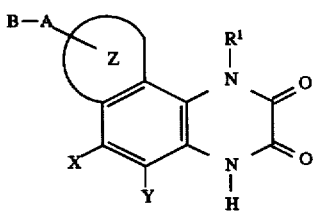

or a pharmaceutically acceptable salt thereof,
wherein
Z is an alicyclic fused ring having 5 to 7 carbon atoms;
$R^1$ is hydrogen, an alkyl or an arylalkyl; and
A is O, $CH_2$, $NR^4$, $CH_2NR^4$, CN, tetrazole or CO wherein $R^4$ is hydrogen, alkyl, hydroxyalkyl, aminoalkyl or aralkyl, wherein
(i) when A is O, $CH_2$, $NR^4$ or $CH_2NR^4$ then B is hydrogen, alkyl, alkenyl, alkynyl, aryl, aralkyl, hydroxyalkyl, alkoxy, aminoalkyl, heterocyclic, alkylheterocyclic, heterocyclic-methyl, heterocyclic-ethyl, alkylcarbonyl, cycloalkylcarbonyl, arylcarbonyl, aralkylcarbonyl, heterocyclic-carbonyl, alkylheterocyclic-carbonyl, or when A is $NR^4$ or $CH_2NR^4$ then B is a naturally occurring α-amino acid moiety joined by an amide bond or B joins with $R^4$ and the nitrogen to form a four to seven membered heterocyclic ring, provided that when Z is a fused cyclohexyl ring and $R^4$ is hydrogen then B is not hydrogen;
(ii) when A is CN then B is not present and Z is not a fused cyclohexyl ring;
(iii) when A is tetrazole then B is hydrogen or alkyl having 1 to 6 carbon atoms; and
(iv) when A is CO then B is hydroxy, alkoxy, aralkoxy, alkyl having 1 to 6 carbon atoms, aralkyl, $NR^7R^8$.

13 Claims, No Drawings

GLUTAMATE RECEPTOR ANTAGONISTS: FUSED CYCLOALKYLQUINOXALINEDIONES

RELATED APPLICATIONS

This is a continuation-in-part of U.S. patent application Ser. No. 08/350,765, filed Dec. 7, 1994 abandoned.

BACKGROUND OF THE INVENTION

FIELD OF THE INVENTION

This invention is related to 2,3-quinoxalinediones having a substituted alicyclic ring fused with the quinoxaline system. The substituted alicyclic ring fused 2,3-quinoxalinediones are active as excitatory amino acid receptor antagonists acting at glutamate receptors, including either or both N-methyl-D-aspartate (NMDA) receptors and non-NMDA receptors such as the α-amino-3-hydroxy-5-methyl-4-isoxazole propionic acid (AMPA) receptor and the kainate receptor. The invention also relates to the use of those quinoxalinediones as neuroprotective agents for treating conditions such as cerebral ischemia or cerebral infarction resulting from a range of phenomena, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as to treat chronic neurodegenerative disorders such as lathyrism, Alzheimer's Disease, Parkinsonism and Huntington's Disease and as anticonvulsants. The compounds of the present invention may also be useful in the treatment of schizophrenia, epilepsy, anxiety, pain and drug addiction.

RELATED BACKGROUND ART

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA) receptor, the α-amino-3-hydroxy-5-methyl-4-isoxazole propionic acid (AMPA) receptor, and the kainate receptor. AMPA/kainate receptors may be referred to jointly as non-NMDA receptors. This excitotoxic action is considered responsible for the loss of neurons in cerebrovascular disorders such as cerebral ischemia or cerebral infarction resulting from a range of conditions, such as thromboembolic or hemorrhagic stroke, cerebral vasospasms, hypoglycemia, cardiac arrest, status epilepticus, perinatal asphyxia, anoxia such as from drowning, pulmonary surgery and cerebral trauma, as well as lathyrism, Alzheimer's Disease, Parkinson's Disease and Huntington's Disease.

Several classes of quinoxalinedione derivatives have been disclosed as glutamate (EAA) receptor antagonists. For example, U.S. Pat. No. 4,889,855, generically discloses compounds of the formula:

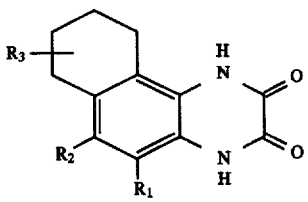

wherein $R_1$, $R_2$ and $R_3$ are independently H, halogen, CN, $NH_2$, $NO_2$, $SO_3H$, $SO_2NH_2$, and $CONH_2$. This reference specifically discloses 6-amino, 6-cyano, 5-carbamoyl, 6-nitro and 5,6-dinitro-7,8,9,10-tetrahydro-2,3-dihydroxybenzo(f)quinoxalines. The reference, however, does not disclose any compounds with substitution of the fused cyclohexyl ring i.e., where $R_3$ is other than hydrogen. Nor does the reference disclose or suggest any methods which would allow substitution of the cyclohexyl ring. U.S. Pat. No. 5,081,123 and U.S. Pat. No. 5,308,845, describe similar structures except that there is respectively a hydroxy or alkoxy function at the nitrogen on the quinoxalinedione skeleton. Again, however, these references do not suggest or illustrate any examples of substituted cyclohexyl rings.

Having both NMDA and non-NMDA antagonist properties in a single entity may provide a superior pharmacological profile. Combinations of NMDA and non-NMDA receptor antagonists have shown synergistic activity in focal and global ischemia [K. Lippert, M. Welsch and J. Krieglstein, Eur. J. Pharmacol. 253 (3), 207–13 (1994)], as anticonvulsants [W. Loescher, C. Rundfelt, D. Hoenack, Eur. J. Neurosci. 5 (11), 1545–50 (1993)], and in protection of neuronal degeneration in retina [J. Mosinger, M. Price, H. Bai, H. Xiao, D. Wozniak and J. Olney, Exp. Neurol. 113, 10–17 (1991).

Among excitatory amino acid receptor antagonists recognized for usefulness in the treatment of disorders are those that block AMPA receptors [C. F. Bigge and T. C. Malone, Curr. Opin. Ther. Pat., 951 (1993); M. A. Rogawski, TiPS 14, 325 (1993)]. AMPA receptor antagonists have prevented neuronal injury in several models of global cerebral ischemia [H. Li and A. M. Buchan, J. Cerebr. Blood Flow Metab. 13, 933 (1993); B. Nellgård and T. Wieloch, J. Cerebr. Blood Flow Metab. 12, 2 (1992)] and focal cerebral ischemia [R. Bullock, D. I. Graham, S. Swanson, J. McCulloch, J. Cerebr. Blood Flow Metab. 14, 466 (1994); D. Xue, Z.-G. Huang, K. Barnes, H. J. Lesiuk, K. E. Smith, A. M. Buchan, J. Cerebr. Blood Flow Metab. 14, 251 (1994)]. AMPA antagonists have also shown efficacy in models for analgesia [X.-J. Xu, J.-X Hao, A. Seiger, Z. Wiesenfeld-Hallin, J. Pharmacol. Exp. Ther. 267, 140 (1993)], and epilepsy [T. Namba, K. Morimoto, K. Sato, N. Yamada, S. Kuroda, Brain Res. 638, 36 (1994); S. E. Brown, J. McCulloch, Brain Res. 641, 10 (1994); S. I. Yamaguchi, S. D. Donevan, M. A. Rogawski, Epilepsy Res. 15, 179 (1993); S. E. Smith, N. Durmuller, B. S. Meldrum, Eur. J. Pharmacol. 201, 179 (1991)]. AMPA receptor antagonists have also demonstrated promise in chronic neurodegenerative disorders such as Parkinsonism. [T. Klockgether, L. Turski, T. Honoré, Z. Zhang, D. M. Gash, R. Kurlan, J. T. Greenamyre, Ann. Neurol., 34(4), 585–593 (1993)].

Excitatory amino acid receptor antagonists that block NMDA receptors are also recognized for usefulness in the treatment of disorders. NMDA receptors are intimately involved in the phenomenon of excitotoxicity, which may be a critical determinant of outcome of several neurological disorders. Disorders known to be responsive to blockade of the NMDA receptor include acute cerebral ischemia (stroke or cerebral trauma, for example), muscular spasm, convulsive disorders, neuropathic pain and anxiety, and may be a significant causal factor in chronic neurodegenerative disorders such as Parkinson's disease [T. Klockgether, L. Turski, Ann. Neurol. 34, 585–593 (1993)], human immunodeficiency virus (HIV) related neuronal injury, amyotrophic lateral sclerosis (ALS), Alzheimer's disease [P. T. Francis, N. R. Sims, A. W. Procter, D. M. Bowen, J. Neurochem. 60 (5), 1589–1604 (1993)] and Huntington's disease. [See S. Lipton, TINS 16 (12), 527–532 (1993); S. A. Lipton, P. A. Rosenberg, New Eng. J. Med. 330 (9), 613–622 (1994); and C. F. Bigge, Biochem. Pharmacol. 45, 1547–1561 (1993) and references cited therein.]. NMDA receptor antagonists may also be used to prevent tolerance to opiate analgesia or to help control withdrawal symptoms from addictive drugs (Eur. Pat. Appl. 488,959A).

An object of this invention is to provide novel substituted alicyclic ring fused 2,3-quinoxalinediones which function as either or both NMDA antagonists or non-NMDA antagonists.

A further object of this invention is to provide a pharmaceutical composition containing an effective amount of the substituted alicyclic fused ring 2,3-quinoxalinediones to treat cerebrovascular disorders responsive to blocking any or all of NMDA receptors, AMPA receptors and kainate-receptors.

Another object of this invention is to provide a method of treating disorders responsive to the antagonism of glutamate or aspartate receptors in a human by administering a pharmaceutically effective amount of the substituted alicyclic fused ring 2,3-quinoxalinediones of this invention.

Another object of this invention is to provide novel methods of preparing substituted alicyclic ring fused 2,3-quinoxalinediones.

A further object of this invention is directed to novel intermediates of the substituted alicyclic ring fused 2,3-quinoxalinediones of this invention.

SUMMARY OF THE INVENTION

The present invention is directed to compounds represented by the formula (I):

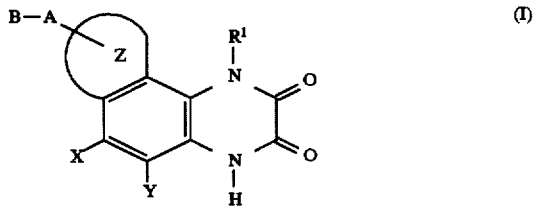

or a pharmaceutically acceptable salt thereof
wherein

Z is an alicyclic fused ring having 5 to 7 carbon atoms;

$R^1$ is hydrogen, an alkyl or an arylalkyl;

X and Y are independently hydrogen, halogen, nitro, cyano, COOH, $CONR^2R^3$, $SONR^2R^3$ wherein $R^2$ and $R^3$, are independently hydrogen, alkyl having 1 to 6 carbon atoms, cycloalkyl or aralkyl; and A is O, $CH_2$, $NR^4$, $CH_2NR^4$, CN, tetrazole or CO wherein $R^4$ is hydrogen, alkyl, hydroxyalkyl, aminoalkyl amine or aralkyl, wherein (i) when a is O, $CH_2$ $NR^4$ or $CH_2NR^4$ then B is hydrogen, alkyl, alkenyl, alkynyl, aryl, aralkyl, hydroxyalkyl, alkoxy, aminoalkyl, heterocyclic, alkylheterocyclic, heterocyclic-methyl, heterocyclic-ethyl alkylcarbonyl, cycloalkylcarbonyl, arylcarbonyl, aralkylcarbonyl, heterocyclic-carbonyl, alkylheterocyclic-carbonyl, any of which may be unsubstituted or substituted by one or more hydroxy, $CO_2H$, mercapto, amino, alkyl or butoxy-carbonyl group, $CONR^5R^6$ wherein $R^5$ is hydrogen, alkyl having 1 to 6 carbon atoms, or aralkyl, and $R^6$ is alkyl, aryl, or aralkyl, or N, $R^5$, and $R^6$ taken together form a cyclic amine, or when A is $NR^4$ or $CH_2NR^4$ then B is a common amino acid moiety joined by an amide bond or B joins with $R^4$ and the nitrogen to form a four to seven membered hetero- cyclic ring, provided that when Z is a fused cyclohexyl ring and $R^4$ is hydrogen then B is not hydrogen;

(ii) when A is CN then B is not present and Z is not a fused cyclohexyl ring;

(iii) when A is tetrazole then B is hydrogen or alkyl having 1 to 6 carbon atoms; and (iv) when A is CO then B is hydroxy, alkoxy, aralkoxy, alkyl having 1 to 6 carbon atoms, aralkyl, $NR^7R^8$ wherein $R^7$ is hydrogen, alkyl having 1 to 6 carbon atoms, or aralkyl, and $R^8$ is alkyl, aryl, or aralkyl, or N, $R^7$, and $R^8$ taken together form a cyclic amine.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate. Alternatively, pharmaceutically acceptable inorganic and organic base addition salts may be used such as sodium hydroxide, potassium hydroxide, lithium hydroxide and the like.

Halogen is fluorine, chlorine, bromine, or iodine; fluorine, chlorine, and bromine are preferred groups.

Alkyl means a straight chained or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Alkenyl means a straight chained or branched chain alkenyl group of two to six carbon atoms or a cyclic alkenyl group of three to seven carbon atoms, for example, but not limited to ethylene, 1,2- or 2,3-propylene, 1-2, 2,3-, or 3,4-butylene, cyclopentene, or cyclohexene.

Alkynyl means a straight chained or branched chain alkynyl group of two to six carbon atoms, for example, but not limited to ethynyl, 2,3-propynyl, 2,3- or 3,4-butynyl.

Aryl means a monocyclic or bicyclic carbocyclic aromatic ring system, for example, but not limited to phenyl, 2-naphthyl, or 1-naphthyl.

Aralkyl means aryl as defined above and alkyl as defined above, for example, but not limited to benzyl, 2-phenylethyl, 3-phenylpropyl; a preferred group is benzyl.

Hydroxyalkyl means alkyl as defined above substituted by a hydroxy group, for example, but not limited to hydroxymethyl, hydroxyethyl, hydroxypropyl, hydroxybutyl, hydroxyheptyl or hydroxyhexyl.

Alkoxy means an alkoxy group containing an alkyl group as defined above.

Aminoalkyl means alkyl as defined above substituted by an amino group, for example, but not limited to aminomethyl, aminoethyl, aminopropyl, aminobutyl, aminoheptyl or aminohexyl.

Heterocyclic means a monocyclic or bicyclic carbocyclic non-aromatic or aromatic 4 to 16 member ring system substituted by one or more hetero atoms, which can be the same or different, and includes, for example, piperidinyl, piperazinyl, morpholinyl, pyrrolidinyl, thienyl, benzo[b] thienyl, naphtho[2,3[b]]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbozolyl, carbozolyl, β-carbolinyl, phenanthridinyl, acrindinyl, perimidinyl, phenanthrolinyl, phenazinyl, isothiazolyl, phenothiazinyl, isoxazoly, furazanyl and phenoxazinyl groups. The heterocyclic group can be unsubstituted or substituted by, for example, hydroxy, thiol, amine, alkyl or butoxycarbonyl groups.

Common amino acid moiety means the naturally occurring α-amino acids.

The instant invention is also related to a pharmaceutical composition containing the compound defined by formula I in an amount effective to treat cerebrovascular disorders responsive to the blockade of glutamate receptors, including either or both NMDA receptors and non-NMDA receptors (such as the α-amino-3-hydroxy-5-methyl-4-isoxazole propionic acid (AMPA) receptor and the kainate receptor), and a pharmaceutically acceptable carrier. Exemplary disorders responsive to such treatment include cerebral ischemia caused by cerebral trauma, stroke, hypoglycemia, heart attack, and surgery; anxiety and schizophrenia; and chronic neurodegenerative disorders such as Huntington's disease, ALS, Parkinsonism and Alzheimer's disease. The pharmaceutical composition of this invention may also be employed as an analgesic or the treatment of epilepsy.

The invention further relates to a method of treating cerebrovascular disorders responsive to antagonism of glutamate receptors including either or both NMDA receptors and non-NMDA receptors by administering a compound of above-defined formula I in a unit dosage form.

The invention is also related to a method for preparing the compound of formula (I) comprising the steps of:

(a) reacting a compound of formula

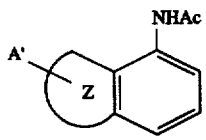

wherein Z is an alicyclic fused ring having 5 to 7 carbon atoms and A' is OH, N$_3$, COOH, COO-alkyl, COO-benzyl, a heterocyclic ring or a protected amine, with a halogenating reagent to produce a compound of formula

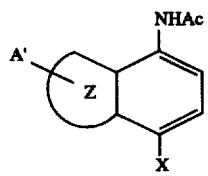

wherein X is a halogen, (b) nitrating the compound formed in step (a) to produce a compound of formula

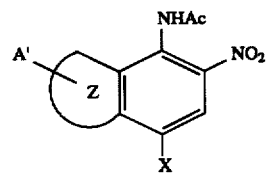

(c) sequentially hydrolyzing an acetamide of the compound of step (b) and then catalytically hydrogenating the hydrolyzed compound to produce a compound of formula

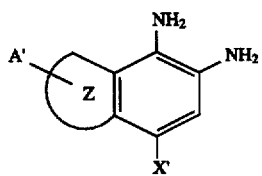

wherein X' is a halogen or hydrogen, (d) condensation of the compound of step (c) with oxalic acid or an oxalic acid ester to produce a compound of formula

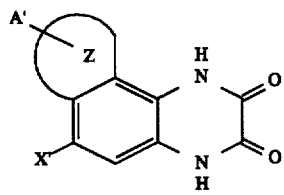

(e) optionally hydrogenating the compound of step (d) when X' is halogen to produce a compound of formula

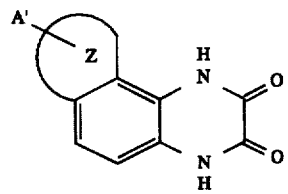

(f) optionally reacting the compound of steps (d) or (e) with an electrophilic substituent to produce a compound of formula

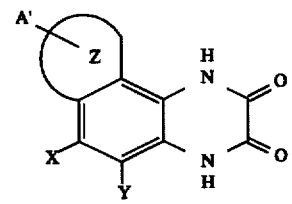

wherein X and Y are independently hydrogen, halogen, nitro, cyano, COOH, CONR$^2$R$^3$, SONR$^2$R$^3$, wherein R$^2$ and R$^3$ are independently hydrogen, alkyl, cycloalkyl or aralkyl; and (g) optionally reacting the compound of steps (d), (e) or (f) when A' is amine or OH with a reagent selected from the group consisting of electrophilic reagents and hydride reagents to produce a compound of formula

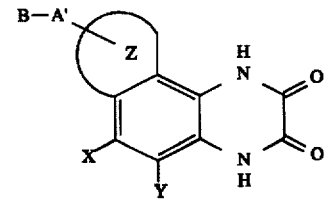

wherein A and B are as defined for formula (I).

Typically the halogenating agent employed in the methods of this invention is selected from the group consisting of bromine, N-bromosuccinimide, chlorine, and iodochloride or the like. When a brominating agent is employed it is preferably present in an acetic acid/sodium acetate solution. The halogenation step is generally carried out at a temperature of about 15°–50° C. for about 15 minutes to 24 hours.

Either fuming nitric acid or potassium nitrate in an acid selected from the group consisting of trifluoroacetic acid, acetic acid, concentrated sulfuric acid or the like are generally employed during the steps of nitrating in the methods described herein.

More particularly, fuming nitric acid in trifluoroacetic acid, acetic acid or the like is employed at about 0° C. to room temperature for about 15 minutes to about 8 hours. Alternatively, fuming nitric acid, potassium nitrate or the like in concentrated sulfuric acid may be used.

Hydrogenation in the methods of this invention is generally accomplished with a nickel or palladium catalyst in a hydrogen atmosphere. For example, deactivated Raney nickel can be used in a hydrogen atmosphere of about 1 atm to 100 psi in a solvent such as methanol, ethanol or tetrahydrofuran or the like. Such a reaction is normally carried out at ambient temperature to about 100° C. It is also possible to employ a more powerful catalyst, such as 20% palladium on carbon under similar conditions in order to dehalogenate the intermediates of this invention.

The step of condensation in the methods of this invention is generally accomplished with oxalic acid or an oxalic acid ester such as dimethyl oxalate or the like. The condensation reaction is preferably carried out at a temperature of about 25°–150° C. for about 30 minutes to 24 hours in an aqueous acidic media or an organic solvent such as acetonitrile, methanol or the like.

The electrophilic reagents typically employed in the methods of this invention are selected from the group consisting of alkyl halides, acylhalide, aldehydes, isocyanates and mixtures thereof. These reagents are generally used in a solvent such as methanol, dimethylformamide or the like at a temperature of about 0° to 100° C. A hydride reagent such as sodium cyanoborohydride or the like may be employed in the methods of this invention when a reductive step is desired such as with reductive amination of an intermediate.

The invention is further related to a method for preparing substituted cyclopentyl fused ring quinoxalinediones comprising the steps of:

(a) acetylating and nitrating a compound of the formula

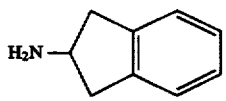

to form a compound of the formula

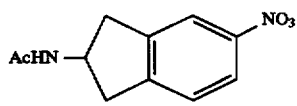

(b) hydrogenation of a nitro group, acetylating a resulting aniline and halogenating the compound formed in step (a) to form a compound of the formula

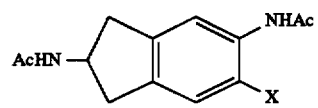

wherein X is a halogen.

(c) nitrating the compound of step (b) to form a compound of the formula

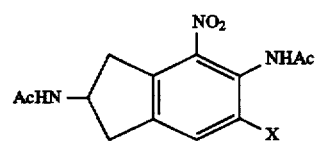

(d) hydrolysis of the compound of step (c) to form a compound of the formula

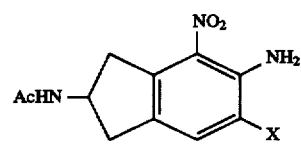

(e) hydrogenating the compound of step (d) to form a diamine compound of the formula

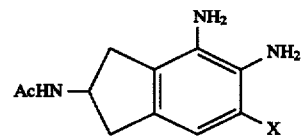

or reacting the compound of step (d) with

wherein $R^{16}$ is hydrogen, alkyl or aralkyl, to form an amide compound of the formula

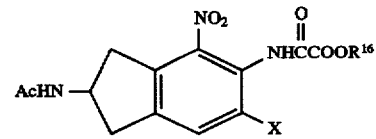

(f) optionally hydrogenating the diamino compound of step (d) to form a compound of the formula

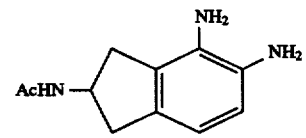

(g) condensation of the diamino compound of step (d) or the compound of step (f) with oxalic acid or an oxalic acid ester or hydrogenation of the amide compound of step (e) to form a compound of the formula

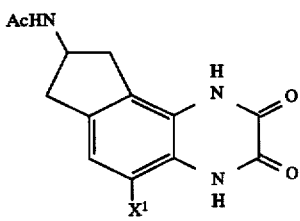

wherein X' is a halogen or hydrogen, or (h) optionally reacting the compound of step (g) with an electrophilic substituent to produce a compound of formula

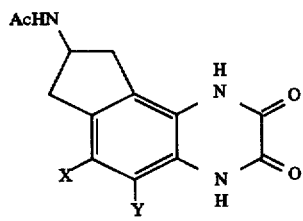

wherein X and Y are the same as defined for formula (I), and (i) optionally hydrolyzing compound of steps (g) or (i) with a reagent selected from the group consisting of electrophilic reagents and hydride reagents to produce a compound of the formula

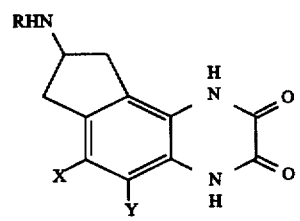

wherein R is hydrogen, alkyl, alkenyl, alkynyl, aryl, aralkyl, alkylheterocyclic, alkylcarbonyl, aralkylcarbonyl, alkylheterocycliccarbonyl, $CONR^5R^6$ wherein $R^5$ is hydrogen, alkyl, aralkyl or $NR^5$ is a cyclic amine and $R^6$ is alkyl, aryl or aralkyl, or a common amino acid moiety joined by an amide bond.

Generally the step of acetylating in this method is performed with acetyl chloride or acetic anhydride at a temperature of about 25° to 80° C. for about 5 minutes to 2 hours. Hydrolysis of the acetamide intermediate in this process can be accomplished with 2N HCL or the like. Other steps in the methods described herein may be readily accomplished by those skilled in the art.

This invention is further directed to novel intermediates which may be prepared during the preparation of the substituted alicyclic ring fused quinoxalinediones of this invention. The novel intermediate compounds are represented by the formulae II, III, IV and V:

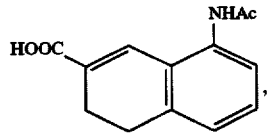
(II)

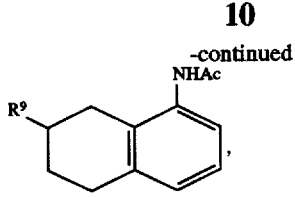
(III)

wherein $R^9$ is $N_3$ or $R^{10}HN$— wherein $R^{10}$ is hydrogen alkyl, alkenyl, alkynl, aryl, aralkyl, alkylheterocyclic, alkylcarbonyl, aralkylcarbonyl, alkylheterocycliccarbonyl, $CONR^5R^6$ wherein $R^5$ is hydrogen, alkyl, aralkyl or $NR^5$ is a cyclic amine and $R^6$ is alkyl, aralkyl, or a common amino acid moiety joined by an amide bond,

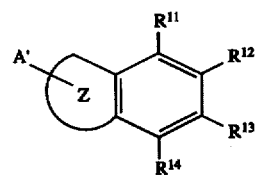
(IV)

wherein A' is OH, $N_3$ or $R^{10}HN$— and $R^{10}$ is as previously described, Z is an alycyclic fused ring having 5 to 7 carbon atoms, $R^{11}$ and $R^{12}$ are independently NHAc,

$NH_2$ or $NO_2$ and $R^{13}$ and $R^{14}$ are independently hydrogen or Br provided that at least one of $R^{13}$ and $R^{14}$ is Br, $R^{17}$ is hydrogen, alkyl or aryl, and

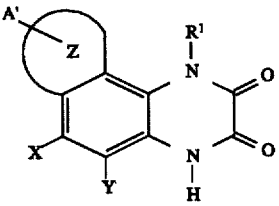
(V)

wherein A' and Z are as previously described provided that when Z is a fused cyclohexyl ring $R^{10}$ is not hydrogen, and $R^1$, X and wherein Y are as described for formula (I). Preferred intermediates of this invention illustrated by formula (IV) include those where when Z is a fused cyclohexyl ring, $R^{11}$ is NHAc or $NH_2$, $R^{12}$ is $NO_2$ or $NH_2$, $R^{13}$ is hydrogen and $R^{14}$ is Br and when Z is a fused cyclopentyl ring $R^{11}$ is $NO_2$ or $NH_2$, $R^{12}$ is NHAc or $NH_2$, $R^{13}$ is Br and $R^{14}$ is hydrogen. Preferred intermediates illustrated by formula (V) include those where Z is a fused cyclopentyl or cyclohexyl ring.

DETAILED DESCRIPTION OF THE PREFERRED EMBODIMENTS

The substituted alicyclic ring fused quinoxalinediones of this invention are represented by previously defined formula I.

Preferably, X and Y are independently hydrogen, bromo and nitro. It is also preferred that $R^1$ is a hydrogen and Z is a fused cyclopentyl or cyclohexyl ring, either of which are substituted by hydroxy, benzyloxy, acetamide, benzyl amino, piperidine-4-carboxylic acid tert-butylester, piperidine-1-carboxylic acid amide, benzamide and cyclohexylamide groups.

More particularly, when A is O then preferably B is hydrogen or a benzyl. When A is $NR^4$ or $CH_2NR^4$, then preferably $R^4$ is hydrogen, methyl or ethyl, and B is methyl, ethyl, acetyl,

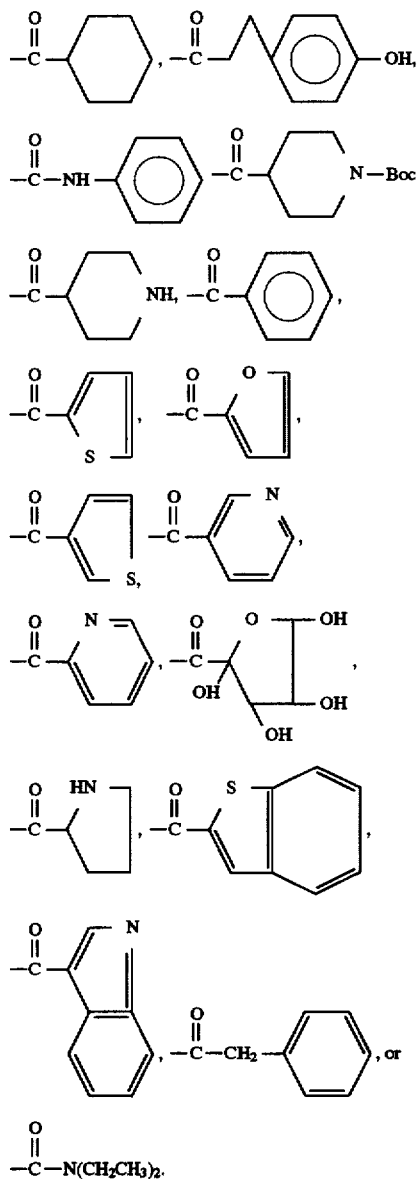

It is also preferred that when A is $NR^4$ or $CH_2NR^4$ then B may join with $R^4$ to form a heterocyclic ring, more preferably a pyrrolidine or piperidine ring.

Exemplary preferred compounds of Formula I include, without limitation:

9-benzyloxy-6-bromo-1,4,7,8,9,10-hexahydrobenzo[f] quinoxaline-2,3-dione;
6-bromo-9-hydroxy-1,4,7,8,9,10-hexahydrobenzo[f] quinoxaline-2,3-dione;
piperidine-4-carboxylic acid (6-nitro-2,3-dioxo-1,2,3,4,7,8, 9,10-octahydro-benzo[f]quinoxalin-9-yl) amide;
N-(6-nitro-2,3-dioxo-1,2,3,4,7,8,9,10-octahydrobenzo[f] quinoxalin-9-yl)-acetamide;
9-benzylamino-6-bromo-1,4,7,8,9,10-hexahydrobenzo[f] quinoxaline-2,3-dione;
N-(5-bromo-2,3-dioxo-2,3,4,7,8,9-hexahydro-1H-cyclopenta[f]-quinoxalin-8-yl)-acetamide;
N-(5-bromo-6-nitro-2,3-dioxo-2,3,4,7,8,9-hexahydro-1H-cyclopenta[f]quinoxalin-8-yl)-acetamide;
N-(2,3-dioxo-2,3,4,7,8,9-hexahydro-1H-cyclopenta[f] quinoxalin-8-yl)-acetamide;
N-(6-nitro-2,3-dioxo-2,3,4,7,8,9-hexahydro-1H-cyclopenta [f]quinoxalin-8-yl)-acetamide;
8-amino-4,7,8,9-tetrahydro-1H-cyclopenta[f]quinoxaline-2, 3-dione hydrochloride;
4-(2,3,-dioxo-2,3,4,7,8,9-hexahydro-1H-cyclopenta[f] quinoxalin-8-ylcarbamoyl)-piperidine-1-carboxylic acid tert-butyl ester;
4-(6-nitro-2,3,-dioxo-2,3,4,7,8,9-hexahydro-1H cyclopenta [f]quinoxalin-8-yl-carbamoyl)-piperidine hydrochloride;
N-(6-nitro-2,3-dioxo-1,2,3,4,7,8,9,10-octahydrobenzo[f] quinoxalin-9-yl)-benzamide;
N-(6-nitro-2,3-dioxo-1,2,3,4,7,8,9,10-octahydrobenzo[f] quinoxalin-9-yl) cyclohexylamide;
8-amino-6-nitro-4,7,8,9-tetrahydro-1H-cyclopenta[f]-quinoxaline-2,3-dione hydrochloride;
N-(6-nitro-2,3-dioxo-4,7,8,9-tetrahydro-1H cyclopenta[f] quinoxalin-8-yl)-benzamide;
4-(6-nitro-2,3-dioxo-1,2,3,4,7,8,9,10-octahydrobenzo[f] quinoxalin-9-ylcarbamoyl)-piperidine hydrochloride;
2-(6-nitro-2,3-dioxo-1,2,3,4,7,8,9,10-octahydrobenzo[f] quinoxalin-9-ylcarbamoyl)ethyl-(4-hydroxy)benzene;
N-phenyl-N'-(6-nitro-2,3-dioxo-1,2,3,4,7,8,9,10-octahydrobenzo[f]quinoxalin-9-yl)-urea;
N-methyl-N-(6-nitro-2,3-dioxo-1,2,3,4,7,8,9,10-octahydrobenzo[f]quinoxalin-9-yl)-benzamide;
thiophene-2-carboxylic acid (6-nitro-2,3-dioxo-2,3,4,7,8,9-hexahydro-1H-cyclopenta[f]quinoxaline-8-yl)-amide;
furan-2-carboxylic acid (6-nitro-2,3-dioxo-2,3,4,7,8,9-hexahydro-1H-cyclopenta[f]quinoxalin-8-yl)-amide;
thiophene-3-carboxylic acid (6-nitro-2,3-dioxo-2,3,4,7,8,9-hexahydro-1H-cyclopenta[f]quinoxalin-8-yl)amide;
N-(6-nitro-2,3-dioxo-2,3,4,7,8,9-hexahydro-1H-cyclopenta [f]quinoxalin-8-yl)-nicotinamide;
pyridine-2-carboxylic acid (6-nitro-2,3-dioxo-2,3,4,7,8,9-hexahydro-1H-cyclopenta[f]quinoxalin-8-yl)amide;
2,3,4,5-tetrahydroxy-tetrahydro-furan-2-carboxylic acid (6-nitro-2,3-dioxo-2,3,4,7,8,9-hexahydro-1H-cyclopenta [f]quinoxalin-8-yl)-amide;
pyrrolidine-2-carboxylic acid (6-nitro-2,3-dioxo-2,3,4,7,8, 9-hexahydro-1H-cyclopenta[f]quinoxalin-8-yl)amide;
benzo[b]thiophene-2-carboxylic acid (6-nitro-2,3,-dioxo-2, 3,4,7,8,9-hexahydro-1H-cyclopenta[f]quinoxalin-8-yl)-amide;
2-(1H-indol-3-yl)-N-(6-nitro-2,3-dioxo-2,3,4,7,8,9-hexahydro-1H-cyclopenta[f]quinoxalin-8-yl)-acetamide;
N-methyl thiophene-2-carboxylic acid-(6-nitro-2,3-dioxo-2, 3,4,7,8,9-hexahydro-1H-cyclopenta[f]quinoxalin-8-yl)-amide;
N-methyl-N-(6-nitro-2,3-dioxo-2,3,4,7,8,9-hexahydro-1H-cyclopenta[f]quinoxalin-8-yl)-benzamide;
6-nitro-2,3-dioxo-2,3,4,7,8,9-hexahydro-1H-cyclopenta[f] quinoxaline-8-carboxylic acid methylphenyl-amide;
6-nitro-2,3,-dioxo-2,3,4,7,8,9-hexahydro-1H-cyclopenta[f] quinoxaline-8-carboxylic acid;
6-nitro-2,3,-dioxo-2,3,4,7,8,9-hexahydro-1H-cyclopenta[f] quinoxaline-8-carboxylic acid phenylamide;
9-methylamino-6-nitro-1,4,7,8,9,10-hexahydrobenzo[f] quinoxaline-2,3-dione;
6-nitro-9-pyrrolidin-1-yl-1,4,7,8,9,10-hexahydrobenzo[f] quinoxaline-2,3-dione;
8-dimethylamino-6-nitro -4,7,8,9-tetrahydro-1H-cyclopenta [f]quinoxaline -2,3-dione;
8-methylamino-6-nitro-4,7,8,9-tetrahydro-1H-cyclopenta[f] quinoxaline-2,3-dione methane sulfonate salt;

2-[bis-(2-hydroxy-ethyl)-amino]-N-(6-nitro-2,3-dioxo-2,3,4,7,8,9-hexahydro-1H-cyclopenta[f]quinoxalin-8-yl) acetamide;

6-nitro-8-pyrrolidin-1-yl-4,7,8,9-tetrahydro-1H-cyclopenta[f]quinoxaline-2,3-dione;

N-methyl-N-(6-nitro-2,3,-dioxo-2,3,4,7,8,9-hexahydro-1H-cyclopenta[f]quinoxaline-8-yl)-acetamide;

6-nitro-8-piperidin-1-yl-4,7,8,9-tetrahydro-1H-cyclopenta[f]quinoxaline-2,3-dione;

8-diethylamino-6-nitro-4,7,8,9, -tetrahydro-1H-cyclopenta[f]quinoxaline-2,3-dione;

6-nitro-8-(thiophen-2-ylmethoxy)-4,7,8,9-tetrahydro-1H-cyclopenta[f]quinoxaline-2,3-dione;

6-nitro-9-(thiophen-2-ylmethoxy)-1,4,7,8,9,10-hexahydro-benzo[f]quinoxaline-2,3-dione;

6-(6-nitro-2,3-dioxo-2,3,4,7,8,9-hexahydro-1H-cyclopenta[f]quinoxalin-8-yloxymethyl)-1,2,3,4-tetrahydro-isoquinoline-3-carboxylic acid;

6-(6-nitro-2,3-dioxo-1,4,7,8,9,10-hexahydrobenzo[f]quinoxalin-9-yloxymethyl)-1,2,3,4-tetrahydro-isoquinoline-3-carboxylic acid;

6-nitro-8-[2-(1H-pyrrol-2-yl)-ethoxy]-4,7,8,9-tetrahydro-1H -cyclopenta[f]quinoxaline-2,3-dione;

6-nitro-9-[2-(1H-pyrrol-2-yl)-ethoxy]-1,4,7,8,9,10-hexahydro-benzo[f]quinoxaline-2,3-dione;

6-nitro-8-{[(1H-tetrazol-5-ylmethyl)-amino]-methyl}-4,7,8,9-tetrahydro-1H-cyclopenta[f]quinoxaline-2,3-dione;

6-nitro-9-{[(1H-tetrazol-5-ylmethyl)-amino]-methyl}-1,4,7,8,9,10-hexahydro-benzo[f]quinoxaline-2,3-dione;

6-nitro-8-[(1H-tetrazol-5-ylmethyl)-amino]-4,7,8,9-tetrahydro-1H-cyclopenta[f]quinoxaline-2,3-dione;

6-nitro-8-[(1H-tetrazol-5-ylmethyl)-amino]-1,4,7,8,9,10-hexahydro-benzo[f]quinoxaline-2,3-dione;

8-{[methyl-(1H-tetrazol-5-ylmethyl)-amino]-methyl}-6-nitro-4,7,8,9-tetrahydro-1H-cyclopenta[f]quinoxaline-2,3-dione;

9-{[methyl-(1H-tetrazol-5-ylmethyl)-amino]-methyl}-6-nitro-1,4,7,8,9,10-hexahydro-benzo[f]quinoxaline-2,3-dione;

6-nitro-8-[2-(1H-tetrazol-5-yl)-ethoxy]-4,7,8,9-tetrahydro-1H-cyclopenta[f]quinoxaline-2,3-dione;

6-nitro-9-[2-(1H-tetrazol-5-yl)-ethoxy]-1,4,7,8,9,10-hexahydro-benzo[f]quinoxaline-2,3-dione;

6-nitro-8-[2-(1H-tetrazol-5-yl)-ethylamino]-4,7,8,9-tetrahydro-1H-cyclopenta[f]quinoxaline-2,3-dione;

6-nitro-9-[2-(1H-tetrazol-5-yl)-ethylamino]-1,4,7,8,9,10-hexahydro-benzo[f]quinoxaline-2,3-dione;

6-nitro-8-(1H-tetrazol-5-ylmethoxy)-4,7,8,9-tetrahydro-1H-cyclopenta[f]quinoxaline-2,3-dione;

6-nitro-9-(1H-tetrazol-5-ylmethoxy)-1,4,7,8,9,10-hexahydro-benzo[f]quinoxaline-2,3-dione;

N-(6-nitro-2,3-dioxo-2,3,4,7,8,9-hexahydro-1H-cyclopenta[f]quinoxalin-8-ylmethyl)-2-(1H-tetrazol-5-yl)-acetamide;

N-(6-nitro-2,3-dioxo-1,4,7,8,9,10-hexahydrobenzo[f]quinoxalin-9-ylmethyl)-2-(1H-tetrazol-5-yl)acetamide;

2-(3-hydroxy-5-methyl-isoxazol-4-yl)-N-(6-nitro-2,3-dioxo-2,3,4,7,8,9-hexahydro-1H-cyclopenta[f]quinoxalin-8-yl)-acetamide;

2-(3-hydroxy-5-methyl-isoxazol-4-yl)-N-(6-nitro-2,3-dioxo-1,4,7,8,9,10-hexahydro-benzo[f]quinoxalin-9-yl)-acetamide;

2-(3-hydroxy-5-methyl-isoxazol-4-yl)-N-(6-nitro-2,3-dioxo-2,3,4,7,8,9-hexahydro-1H-cyclopenta[f]quinoxalin-8-ylmethyl)-acetamide;

2-(3-hydroxy-5-methyl-isoxazol-4-yl)-N-(6-nitro-2,3-dioxo-1,4,7,8,9,10-hexahydro-benzo[f]quinoxalin-9-ylmethyl)-acetamide;

8-(3-hydroxy-5-methyl-isoxazol-4-ylmethoxy)-6-nitro-4,7,8,9-tetrahydro-1H-cyclopenta[f]quinoxaline-2,3-dione;

9-(3-hydroxy-5-methyl-isoxazol-4-ylmethoxy)-6-nitro-1,4,7,8,9,10-hexahydro-benzo[f]quinoxaline-2,3-dione;

N-(6-nitro-2,3-dioxo-2,3,4,7,8,9-hexahydro-1H-cyclopenta[f]quinoxalin-8-yl)-2-(1H-tetrazol-5-yl)-acetamide;

N-(6-nitro-2,3-dioxo-1,4,7,8,9,10-hexahydrobenzo[f]quinoxalin-9-yl)-2-(1H-tetrazol-5-yl)-acetamide;

3-[(6-nitro-2,3-dioxo-2,3,4,7,8,9-hexahydro-1H-cyclopenta[f]quinoxalin-8-ylmethyl)-carbamoyl]-1,2,3,4-tetrahydro-isoquinoline-6-carboxylic acid;

3-[(6-nitro-2,3-dioxo-1,4,7,8,9,10-hexahydrobenzo[f]quinoxalin-9-ylmethyl)-carbamoyl]-1,2,3,4-tetrahydro-isoquinoline-6-carboxylic acid;

8-[2-(3-hydroxy-5-methyl-isoxazol-4-yl)-ethoxy]-6-nitro-4,7,8,9-tetrahydro-1H-cyclopenta[f]quinoxaline-2,3-dione;

9-[2-(3-hydroxy-5-methyl-isoxazol-4-yl)-ethoxy]-6-nitro-1,4,7,8,9,10-hexahydro-benzo[f]quinoxaline-2,3-dione;

2-(2-hydroxy-phenyl)-N-(6-nitro-2,3-dioxo-2,3,4,7,8,9-hexahydro-1H-cyclopenta[f]quinoxalin-8-yl)-acetamide;

2-(2-hydroxy-phenyl)-N-(6-nitro-2,3-dioxo-1,4,7,8,9,10-hexahydro-benzo[f]quinoxalin-9-yl)-acetamide;

2-hydroxy-N-(6-nitro-2,3-dioxo-2,3,4,7,8,9-hexahydro-1H-cyclopenta[f]quinoxalin-8-ylmethyl)-benzamide;

2-hydroxy -N-(6-nitro-2,3-dioxo-1,4,7,8,9,10-hexahydrobenzo[f]quinoxalin-9-ylmethyl)-benzamide;

6-nitro-8-(2-pyridin-2-yl-ethoxy)-4,7,8,9-tetrahydro-1H-cyclopenta[f]quinoxaline-2,3-dione;

6-nitro-9-(2-pyridin-2-yl-ethoxy)-1,4,7,8,9,10-hexahydro-benzo[f]quinoxaline-2,3-dione;

N-(6-nitro-2,3-dioxo-2,3,4,7,8,9-hexahydro-1H-cyclopenta[f]quinoxalin-8-yl)-2-[2-(1H-tetrazol-5-yl)phenyl]-acetamide;

N-(6-nitro-2,3-dioxo-1,4,7,8,9,10-hexahydrobenzo[f]quinoxalin-9-yl)-2-[2-(1H-tetrazol-5-yl)phenyl]-acetamide;

1-methyl-2,4-dioxo-1,2,3,4-tetrahydro-pyrimidine-5-carboxylic acid (6-nitro-2,3-dioxo-2,3,4,7,8,9-hexahydro-1H-cyclopenta[f]quinoxalin-8-ylmethyl)-amide;

1-methyl-2,4-dioxo-1,2,3,4-tetrahydro-pyrimidine-5-carboxylic acid (6-nitro-2,3-dioxo-1,4,7,8,9,10-hexahydro-benzo[f]quinoxalin-9-ylmethyl)-amide;

6-nitro-8-(5-oxo-4,5-dihydro-[1,3,4]oxadiazol-2-ylmethoxy)-4,7,8,9-tetrahydro-1H-cyclopenta[f]quinoxaline-2,3-dione;

6-nitro-9-(5-oxo-4,5-dihydro-[1,3,4]oxadiazol-2-ylmethoxy)-1,4,7,8,9,10-hexahydro-benzo[f]quinoxaline-2,3-dione;

6-nitro-8-(pyridin-2-ylamino)-4,7,8,9-tetrahydro-1H-cyclopenta[f]quinoxaline-2,3-dione;

6-nitro-9-(pyridin-2-ylamino)-1,4,7,8,9,10-hexahydro-benzo[f]quinoxaline-2,3-dione;

4-{[(6-nitro-2,3-dioxo-2,3,4,7,8,9-hexahydro-1H-cyclopenta[f]quinoxalin-8-ylmethyl)-amino]methyl}-benzoic acid;

4-{[(6-nitro-2,3-dioxo-1,4,7,8,9,10-hexahydrobenzo[f]quinoxalin-9-ylmethyl)-amino]methyl}-benzoic acid;

2-hydroxy-benzoic acid 6-nitro-2,3-dioxo-2,3,4,7,8,9-hexahydro-1H-cyclopenta[f]quinoxalin-8-yl ester;

2-hydroxy-benzoic acid 6-nitro-2,3-dioxo-1,4,7,8,9,10-hexahydro-benzo[f]quinoxalin-9-yl ester;

N-(6-nitro-2,3-dioxo-2,3,4,7,8,9-hexahydro-1H-cyclopenta[f]quinoxalin-8-yl)-phthalamic acid;

N-(6-nitro-2,3-dioxo-1,4,7,8,9,10-hexahydro-benzo[f]quinoxalin-9-yl)-phthalamic acid;

2-(6-nitro-2,3-dioxo-2,3,4,7,8,9-hexahydro-1H-cyclopenta[f]quinoxalin-8-yloxy)-benzoic acid;

2-(6-nitro-2,3-dioxo-1,4,7,8,9,10-hexahydro-benzo[f]
  quinoxalin-9-yloxy)-benzoic acid;
(3-hydroxy-5-methyl-isoxazol-4-yl)-acetic acid 6-nitro-2,3-
  dioxo-2,3,4,7,8,9-hexahydro-1H-cyclopenta[f]
  quinoxalin-8-yl ester;
(3-hydroxy-5-methyl-isoxazol-4-yl)-acetic acid 6-nitro-2,3-
  dioxo-1,4,7,8,9,10-hexahydro-benzo[f]quinoxalin-9-yl
  ester;
2-hydroxy-N-(6-nitro-2,3-dioxo-2,3,4,7,8,9-hexahydro-1H-
  cyclopenta[f]quinoxalin-8-yl)-benzamide; and
2-hydroxy-N-(6-nitro-2,3-dioxo-1,4,7,8,9,10-
  hexahydrobenzo[f]quinoxalin-9-yl)-benzamide.

This invention is also directed to methods for preparing the substituted alicyclic fused ring 2,3-quinoxalinedione compounds of formula I. One embodiment of this invention is directed to the method employing the exemplary reaction schemes set forth in Schemes II and III employing starting materials prepared, for example, via the method set forth in Scheme I. Yet another embodiment of this invention is directed to the method of preparing the substituted cyclopentyl fused ring compounds of formula I via the reaction Scheme IV. The starting materials employed in these reaction schemes are either readily available, can be prepared by known methods or by the method set forth in Scheme I.

Scheme I

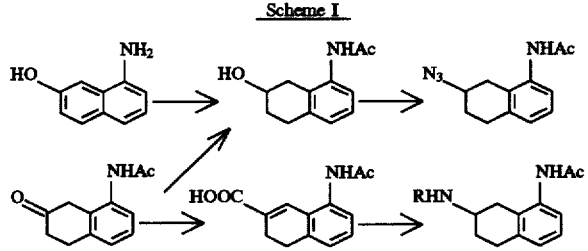

The tetrahydronaphthalene derivatives substituted on the saturated ring, as shown in Scheme 1, are readily available or prepared by those skilled in the art. For example, 1-amino-7-hydroxynaphthalene can be hydrogenated at a pressure from about 50 to about 1000 psi and at a temperature of about 20° C. to about 100° C. to form the tetrahydronaphthalene adduct, which can then act as a starting material for hydroxy and ether adducts, or via conversion to a leaving group such as a mesylate, tosylate, halide or the like, can be further elaborated to an azide by treatment with sodium azide, or displaced by an amine by nucleophilic substitution. Stereochemistry at the chiral center can be controlled by means known to those skilled in the art, such as Mitsunobu inversion, or by separation via chiral salts or chiral chromatography, or by reacting with a chiral protecting group and separating the resulting disastereomeric mixture.

Alternatively, a β-tetralone (or α-tetralone) derivative can be reduced directly to the alcohol using any number of reducing agents such as sodium borohydride, or converted to the carboxylic acid adduct by formation of the cyanohydrin, followed by elimination and hydrolysis. Subsequent treatment with diphenylphosphoryl azide or the like (Schmidt rearrangement), followed by heating and alcoholysis (or hydrolysis) can lead to either the carbamate or unprotected amine.

Another embodiment of this invention is directed to a second novel process of preparing the compound of Formula I in the following manner.

Scheme II set forth below illustrates a method of preparing novel intermediates and the substituted alicyclic fused ring 2,3-quinoxalinediones of this invention employing starting materials that are either readily available or prepared via Scheme I.

Scheme II

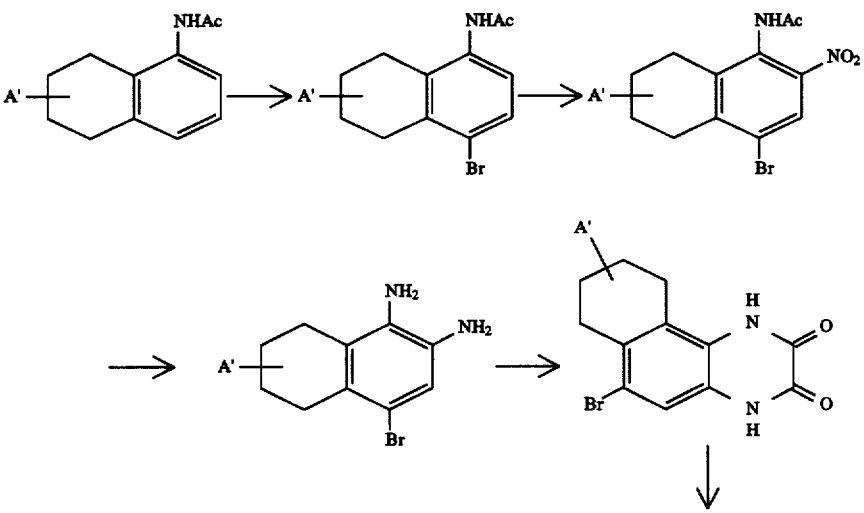

-continued
Scheme II

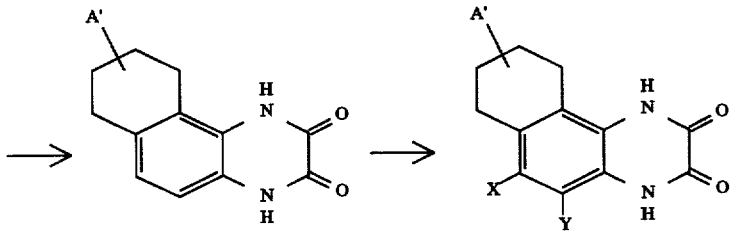

As shown in Scheme II wherein A' is OH, N₃, a heterocyclic ring or a protected amine, the aromatic ring can be manipulated by sequential electrophilic aromatic substitution reactions, bromination and nitration, to obtain the desired substitution pattern. Reduction of the nitro functionality via catalytic hydrogenation can be done under conditions that give the diamine with the bromine intact, or give the diamine and dehalogenation. Subsequent condensation with oxalic acid provides the benzo(f)quinoxalinedione. Hydrogenolysis of the bromine followed by electrophilic aromatic substitution provides aryl substituted derivatives.

The compounds of this invention may be prepared employing the compound prepared via Scheme II. This is illustrated by Scheme III below.

Scheme III

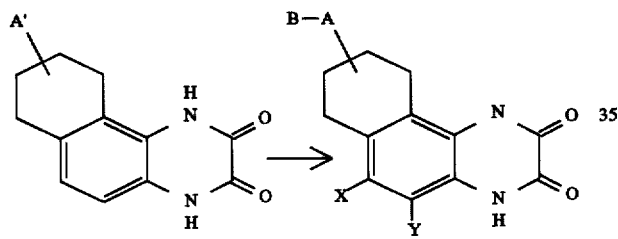

When A' is OH or NH₂, the alcohol or amine can be reacted with an electrophilic reagent, such as an alkyl halide, mesylate or tosylate or the like, or an acid chloride, acylimidazole or the like, to generate ethers, esters, secondary amine or amides. When A' is COOH, it can be activated as an acylimidazole, or the like, with carbonyldiimidazole (or dicyclohexylcarbodiimide) and then reacted with amines or alcohols to form the reverse amide or ester. When X,Y are nonreactive species, hydride reagents can be used to reduce the amide derivatives to amines; in the case where A' is NHCO— the amine is directly attached to the cyclohexyl ring, and when A' is CONR—, a methylene spacer separates the amine from the cyclohexyl ring. Preparation of analogs that incorporate a fused cyclopentyl ring rather than the cyclohexyl ring can be accomplished in a similar manner.

Yet another embodiment of this invention is directed to the process of preparing substituted cyclopentyl fused ring 2,3-quinoxalinediones compounds of Formula I as shown below.

Scheme IV

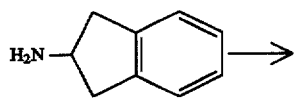

-continued
Scheme IV

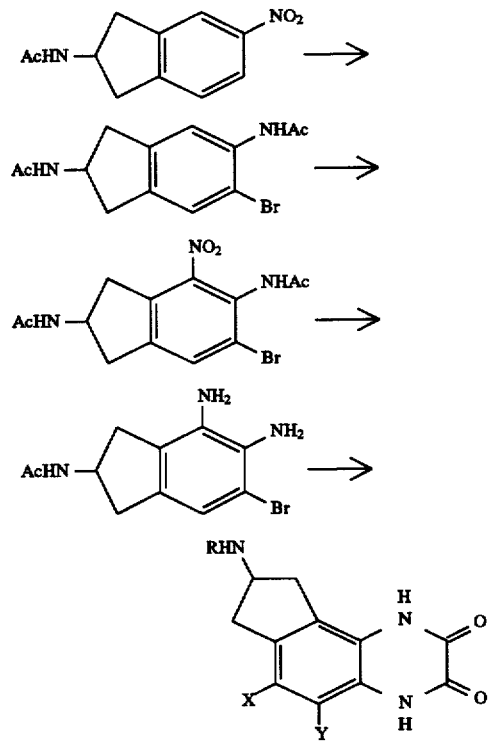

The disposition of the functional groups on the aromatic ring in the cyclopentyl ring fused analogs can be established by traditional aromatic electrophilic substitution reactions as shown in Scheme IV. Introduction of the nitro functionality followed by reduction and acetylation of the aniline allows bromination to proceed primarily in the least hindered positions ortho to the acetamide. Nitration is then directed to the open ortho position which establishes the correct regiochemistry for the entire aromatic ring. After formation of the quinoxalinedione, the final substitution pattern on the aromatic ring can be established by standard chemistry known to those skilled in the art. The exo amino functionality on the cyclopentyl ring can be manipulated as shown before in Scheme III.

A preferred method for preparing the compound of formula (I) comprises the steps of:

(a) reacting a compound of formula

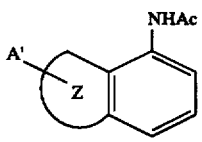

wherein Z is an alicyclic fused ring having 5 to 7 carbon atoms and A' is OH, N₃, COOH, COO-alkyl, COO-benzyl, a heterocyclic ring such as a pyrrolidine or a piperidine, or a protected amine such as phthalimide, acetamide or a carbamate (e.g., Boc or Cbz), with a brominating agent to produce a compound of formula

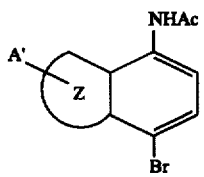

(b) nitrating the compound formed in step (a) to produce a compound of formula

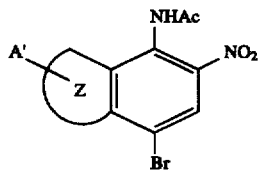

(c) catalytically hydrogenating the compound of step (b) to produce a compound of formula

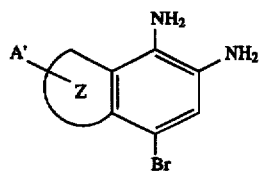

(d) condensation of the compound of step (c) with oxalic acid or an oxalic acid ester such as dimethyl oxalate or the like, to produce a compound of formula

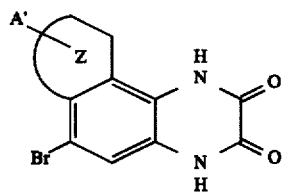

(e) optionally hydrogenating the compound of step (d) to produce a compound of formula

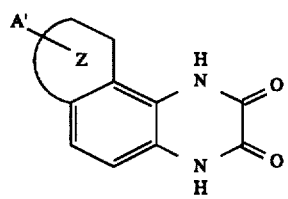

(f) optionally reacting the compound of steps (d) or (e) with an electrophilic substituent to produce a compound of formula

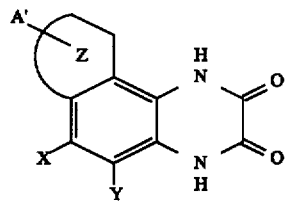

wherein X and Y are independently hydrogen, halogen, nitro, cyano, COOH, CONR²R³, SONR²R³, wherein R² and R³ are independently hydrogen, alkyl, cycloalkyl or aralkyl; and (g) optionally reacting the compound of steps (d), (e) or (f) wherein A' is NR⁴H or OH with a reagent selected from the group consisting of electrophilic reagents and hydride reagents, to produce a compound of formula

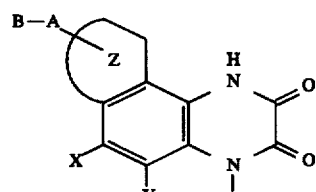

wherein A, B and R⁴ are as defined for formula (1). Exemplary electrophilic reagents include alkyl halides mesylates, tosylates, acid chlorides, acylimidazoles, isocyanates, aldehydes and the like. When A' is COOH, it can be activated with a coupling reagent such as CDI, DCC, thionyl chloride and the like and further reacted with an amine, including natural amino acids, or alcohols, to obtain the corresponding amides and esters. In this preferred method A' may also be a piperidine or pyrrolidine ring.

The preparation of substituted cyclopentyl fused ring quinoxalinediones can be preferably accomplished by:

(a) acetylating and nitrating a compound of the formula

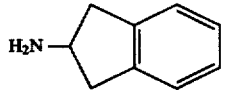

to form a compound of the formula

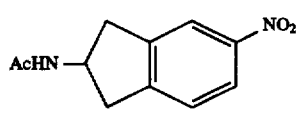

(b) reducing, acetylating and brominating the compound formed in step (a) to form a compound of the formula

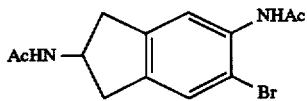

(c) nitrating the compound of step (b) to form a compound of the formula

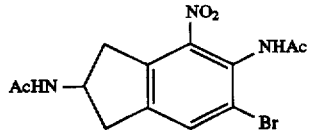

(d) hydrogenating the compound of step (c) to form a compound of the formula

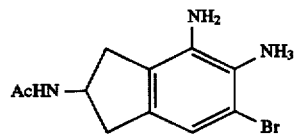

(e) optionally hydrogenating the compound of step (d) to form a compound of the formula

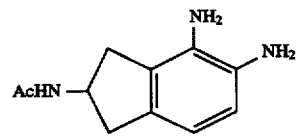

(f) condensation of the compound of steps (d) or (e) with oxalic acid to form a compound of the formula

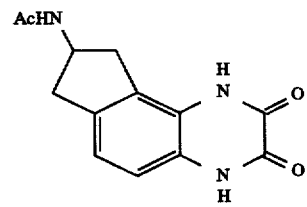

(g) optionally reacting the compound of step (f) with an electrophilic substituent to produce a compound of formula

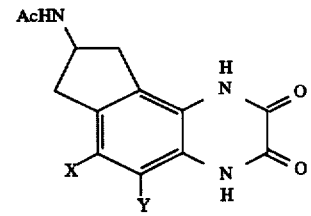

wherein X and Y are the same as defined for formula (I), and (h) optionally reacting the compound of steps (f) or (g) with a reagent selected from the group consisting of electrophilic reagents and hydride reagents, to produce a compound of the formula

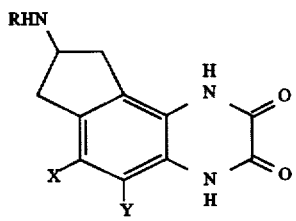

wherein R is hydrogen, alkyl, alkenyl, alkynyl, aryl, aralkyl, alkylheterocyclic, alkylcarbonyl, aralkylcarbonyl, alkylheterocycliccarbonyl, $CONR^5R^6$ wherein $R^5$ is hydrogen, alkyl, aralkyl or $NR^5$ is a cyclic amine and $R^6$ is alkyl, aryl, aralkyl or not present, or a common amino acid moiety joined by an amide bond.

The methods set forth herein, and particularly as illustrated in Schemes I, II, III and IV, may also be employed to prepare novel intermediates of this invention. The preferred novel intermediates include:

acetic acid 8-acetylamino-5-bromo-7-nitro-1,2,3,4-tetrahydronaphthalen-2-yl ester;
8-amino-5-bromo-7-nitro-1,2,3,4-tetrahydronaphthalen-2-ol;
7,8-diamino-5-bromo-1,2,3,4-tetrahydronaphthalen-2-ol;
methanesulfonic acid 8-acetyl-1,2,3,4-tetrahydronaphthalen-2-yl ester;
N-(7-azido-5,6,7,8-tetrahydronaphthalene-1-yl)acetamide;
N-(7-azido-4-bromo-5,6,7,8-tetrahydronaphthalen-1-yl) acetamide;
N-(7-azido-4-bromo-2-nitro-5,6,7,8-tetrahydronaphthalen-1-yl) acetamide;
7-azido-4-bromo-2-5,6,7,8-tetrahydro-naphthalen-1-ylamine;
N-7-benzyl-4-bromo-2-nitro-5,6,7,8-tetrahydronaphthalene-1,7-diamine;
N-(5-acetylamino-6-bromo-indan-2-yl)-acetamide;
N-(5-acetylamino-6-bromo-4-nitro-indan-2-yl)-acetamide;
N-(5-amino-6-bromo-4-nitro-indan-2-yl)-acetamide;
6-bromo-4-nitro-indan-2,5-diamine monohydrochloride; and
N-(4,5-diamino-6-bromo-indan-2-yl)-acetamide.

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazolepropionic acid (or kainic acid) binding site on AMPA (non-NMDA) receptors or the glycine site of NMDA receptors. The compounds generally have activity at both NMDA and non-NMDA receptors, and thus may act in disorders arising from over excitation of either receptor family.

The compounds of the present invention exhibit binding affinity for the AMPA receptors as described by Honoré T., et al., Neuroscience Letters 1985; 54:27–32. Preferred compounds demonstrate $IC_{50}$ values <100 µM in this assay. The compounds of the present invention exhibit binding affinity for the kainate site (non-NMDA receptor) as described by London, E. D. and Coyle, J, Mol. Pharmacol, 1979; 15:492. The compounds of the present invention exhibit binding affinity for the glycine site of the NMDA receptor as described by Jones, S. M. et al., Pharmacol. Methods 1989; 21:161. To functionally measure AMPA antagonist activity, the effects of the agent on AMPA-induced neuronal damage in primary cortical neuronal cultures was examined using techniques similar to those outlined by Koh, J.-Y. et al., *J. Neurosci*, 1990; 10:693. The neuronal damage produced by long-term exposure to 100 μM AMPA was measured by the release of the cytosolic enzyme lactate dehydrogenase (LDH).

Selected compounds of the present invention were tested by one or more of the above-described assays. The data obtained in these assays is set forth in Tables 1 and 2. The $IC_{50}$ values set forth in Tables 1 and 2 are a measure of the concentration (μM) of the test substance which inhibits 50% of an induced release from the tested receptors.

TABLE 1

Cyclohexyl-fused Analogs

| Compound of Example | AMPA ($IC_{50}$ μM) | Kainate ($IC_{50}$ μM) | Glycine ($IC_{50}$ μM) | LDH ($IC_{50}$ μM) |
|---|---|---|---|---|
| (7) | 17 | 3 | 1.5 | |
| (8) | 14 | >100 | | |
| (15) | 0.7 | 2.8 | 1.8 | 20 |
| (17) | 0.56 | 2.2 | 0.62 | >30 |
| (19) | 25 | >100 | >100 | |
| (36) | 0.42 | 0.9 | 0.09 | 30 |
| (37) | 1.1 | 1.4 | 0.5 | 28 |
| (40) | 0.27 | 0.82 | 0.28 | 25 |
| (41) | 0.96 | 1.4 | >1 | |
| (42) | 0.15 | 0.83 | 0.18 | |
| (52) | 0.79 | 2.8 | >1 | |
| (53) | 1.1 | 1.6 | | |
| (86) | 2.2 | 3.8 | | |

TABLE 2

Cyclopentyl-fused Analogs

| Compound of Example | AMPA ($IC_{50}$ μM) | Kainate ($IC_{50}$ μM) | Glycine ($IC_{50}$ μM) | LDH ($IC_{50}$ μM) |
|---|---|---|---|---|
| (28) | >100 | >100 | | |
| (29) | 5.1 | | | |
| (30) | 25 | 87 | | |
| (32) | 0.4 | 0.9 | 1.3 | |
| (35) | 0.12 | 0.28 | <1 | |
| (38) | 2.6 | 2.1 | | |
| (39) | 0.11 | 0.48 | 0.4 | 18 |
| (54) | 0.05 | 0.18 | 0.3 | |
| (59) | 0.14 | 0.38 | >1 | 14 |
| (60) | 0.10 | 0.36 | 0.4 | 14 |
| (61) | 0.20 | 1.03 | >1 | 28 |
| (62) | 0.56 | 1.9 | >1 | |
| (63) | 0.58 | 1.1 | >1 | >30 |
| (64) | 0.64 | 0.86 | >1 | |
| (65) | 1.3 | 8.1 | | |
| (66) | 1.3 | 2.3 | | |
| (67) | 3.6 | 1.6 | | |
| (68) | 7.4 | 1.9 | | |
| (69) | 0.42 | 1.6 | >100 | |
| (78) | 0.42 | 1.9 | 14 | |
| (80) | 1.6 | 3.9 | | |
| (90) | 0.91 | 2.6 | 12 | |
| (100) | 1.2 | 2.2 | | |
| (101) | 1.1 | 1.4 | | |
| (104) | 1.5 | 2.2 | | |
| (105) | 2.2 | 2.2 | | |
| (108) | 3.4 | 1.6 | | |
| (109) | 5.1 | 5.4 | | |

Additionally, as a preliminary indicator of in vivo CNS activity related to anticonvulsant activity and potential neuroprotection, a maximal electroshock assay in CF-1 strain mice (20–25 g) was performed with corneal electrodes by conventional methods as described previously (Krall et al., *Epilepsia* 1988; 19:409–428. The compounds of this invention generally demonstrated $ED_{50}$ values of <50 mg/kg.

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprises conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, and accordingly suitable representative unit dosage forms.

Solid forms of pharmaceutical compositions for PO administration and injectable solutions are preferred.

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 50 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The examples which follow are intended as an illustration of certain preferred embodiments of the invention, and no limitation of the invention is implied.

EXAMPLE 1

Preparation of N-(7-hydroxy-5,6,7,8-tetrahydronaphthalen-1-yl)-acetamide

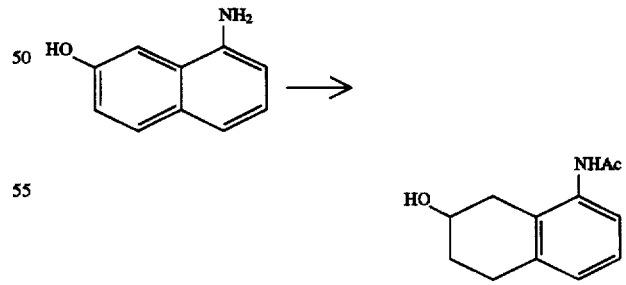

A mixture of 1-amino-7-hydroxynaphthalene (16.5 g, 0.1 mol), lithium hydroxide hydrate (4.3 g) and 20% palladium on carbon (4 g) was suspended in 600 mL 4:1 methanol and water and shaken on a Parr hydrogenation apparatus under a hydrogen atmosphere (52 psi) for about one hour. The hydrogen atmosphere was then recharged, and the mixture shaken an additional hour. After filtration through celite, the filtrate was concentrated and the pH adjusted with aqueous HCl to 7. Acetic anhydride (15 g) was added and swirled for 15 min. The solution was saturated with sodium chloride and extracted with ethyl acetate (3×). The combined organic layer was dried over magnesium sulfate, filtered and evaporated to give the product (9.5 g) in 46% yield.

EXAMPLE 2

Preparation of acetic acid 8-acetylamino-1,2,3,4-tetrahydronaphthalen-2-yl ester

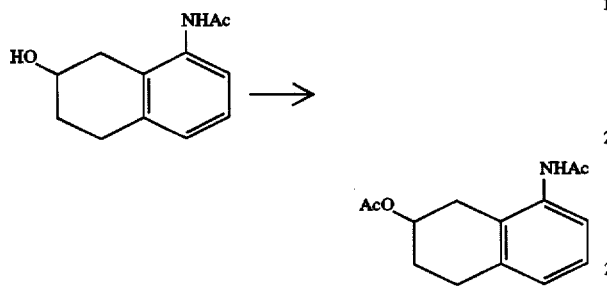

A mixture of N-(7-hydroxy-5,6,7,8-tetrahydronaphthalen-1-yl)-acetamide (3 g, 15 mmol), acetic anhydride (2 g, 200 mmol) in pyridine (50 mL) was stirred at room temperature for 18 h. Solvent was removed by rotoevaporation and the residue was purified by column chromatography on silica gel (1:1 ethyl acetate:hexane as eluant) to give the product (2.2 g) as a tan solid in 59% yield.

EXAMPLE 3

Preparation of acetic acid 8-acetylamino-5-bromo-1,2,3,4-tetrahydronaphthalen-2-yl ester

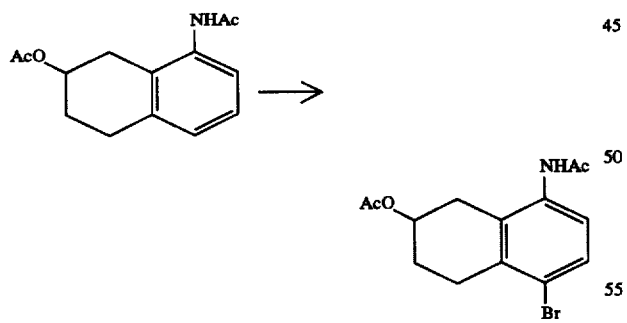

A mixture of acetic acid 8-acetylamino-1,2,3,4-tetrahydronaphthalen-2-yl ester (2.2 g, 8.9 mmol) and bromine (1.7 g, 10.7 mmol) in 50 mL of acetic acid was stirred at room temperature for 18 h. The solvent was removed by rotoevaporation, and the residue was taken up in a diethyl ether/water mixture. The resulting solid was collected by filtration, and washed with diethyl ether. After drying the product (2.75 g) was obtained in 95% yield.

EXAMPLE 4

Preparation of acetic acid 8-acetylamino-5-bromo-7-nitro-1,2,3,4-tetrahydronaphthalen-2-yl ester

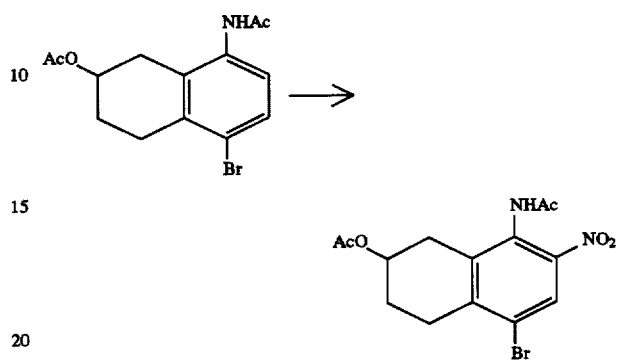

A solution of acetic acid 8-acetylamino-5-bromo-1,2,3,4-tetrahydronaphthalen-2-yl ester (2.6 g, 8 mmol) in 40 mL of trifluoroacetic acid was cooled in an ice bath. Fuming nitric acid (2 mL) was added dropwise and the mixture was stirred for 2.5 h. The solvent was removed by rotoevaporation, and water was added to the residue which induced solidification. The solid was collected by filtration, washed with ether and dried to give the product (2.4 g) in 81% yield.

EXAMPLE 5

Preparation of 8-amino-5-bromo-7-nitro-1,2,3,4-tetrahydronaphthalen-2-ol

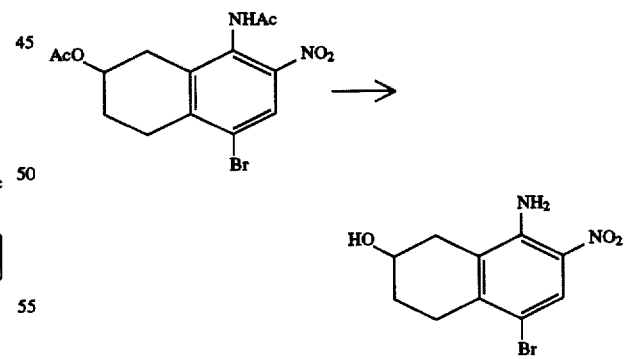

A mixture of acetic acid 8-acetylamino-5-bromo-7-nitro-1,2,3,4-tetrahydronaphthalen-2-yl ester (2 g, 5.4 mmol), acetic acid (15 mL) and 6N HCl (30 mL) was stirred at 90° C. for 18 h. The solvent was removed by rotoevaporation to give the product (1.6 g) as an orange solid in quantitative yield.

EXAMPLE 6

Preparation of 7,8-diamino-5-bromo-1,2,3,4-tetrahydronaphthalen-2-ol

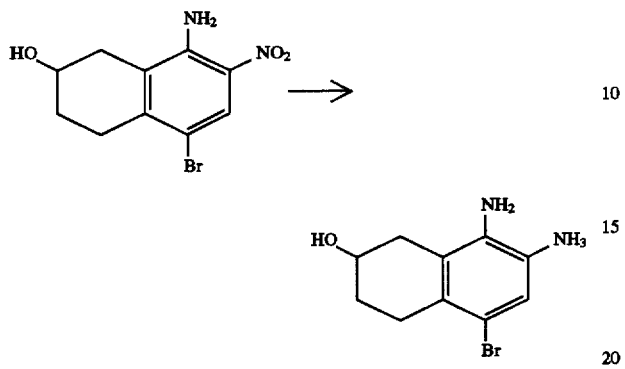

Raney nickel was deactivated prior to use by washing twice with acetone, and then washing twice with tetrahydrofuran. A mixture of 8-amino-5-bromo-7-nitro-1,2,3,4-tetrahydronaphthalen-2-ol (1.8 g) and Raney nickel (4 g) in tetrahydrofuran (100 mL) was stirred under a hydrogen atmosphere (1 atm) for 1 h. The catalyst was removed by filtration, and the filtrate evaporated. The solid residue was washed with diethyl ether and then dried to give the desired product.

EXAMPLE 7

Preparation of 6-bromo-9-hydroxy-1,4,7,8,9,10-hexahydro-benzo[f]quinoxaline-2,3-dione

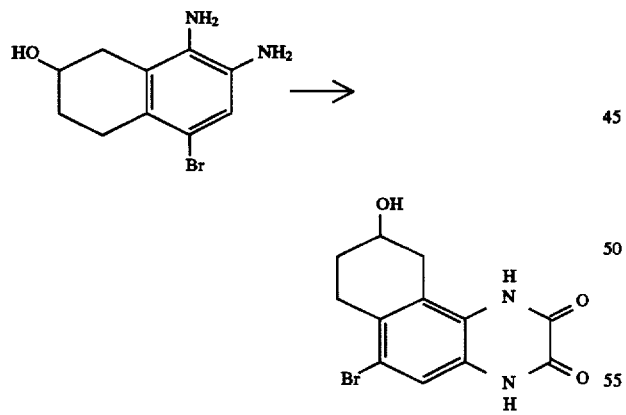

A mixture 7,8-diamino-5-bromo-1,2,3,4-tetrahydronaphthalen-2-ol (0.5 g, 2 mmol) and oxalic acid (0.5 g, 4 mmol) in 2N HCl (20 mL) was heated at 90° C. for 3 h. A solid was collected by filtration, washed consecutively with water and diethyl ether and dried to give the quinoxalinedione product (0.33 g). CHN: calc'd for $C_{12}H_{11}BrN_2O_3 \cdot 1.5H_2O$—C, 42.62; H, 4.17; N; 8.29; found-C, 42.87; H, 3.73; N, 8.29.

EXAMPLE 8

Preparation of 9-benzyloxy-6-bromo-1,4,7,8,9,10-hexahydro-benzo[f]quinoxaline-2,3-dione

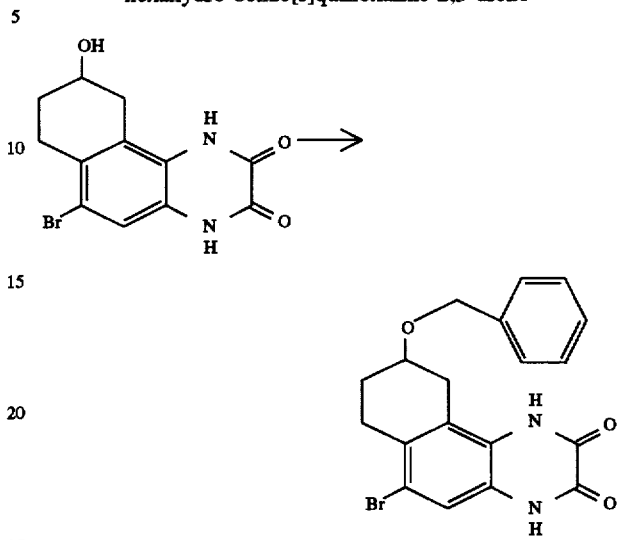

A mixture of 6-bromo-9-hydroxy-1,4,7,8,9,10-hexahydrobenzo[f]quinoxaline-2,3-dione (0.1 g, 0.32 mmol) and sodium hydride (16 mg, 0.4 mmol) in dimethylformamide (1 mL) was stirred at 0° C. for 30 min, and then treated with benzyl bromide (70 mg, 0.4 mmol). The reaction mixture was stirred for 48 h and warmed to room temperature during that time. The solvent was removed by rotoevaporation, the residue triturated in ethyl acetate, and the solid collected by filtration and dried. CI MS m/e (M+1) 402, 404. H-NMR (200 MH$_2$, dmso): 1H, s, 12.05; 1H, s, 11.95; 5H, m, 7.4–7.2; 1H, s, 7.05; 2H, s, 5.4; 1H, s, 4.75; 1H, m, 3.9; +ring protons.

EXAMPLE 9

Preparation of methanesulfonic acid 8-acetylamino-1,2,3,4-tetrahydronaphthalen-2-yl ester

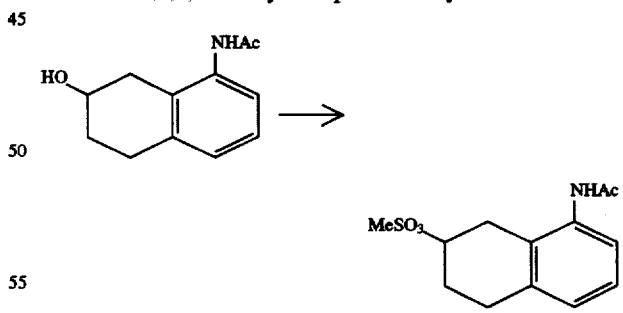

A solution of N-(7-hydroxy-5,6,7,8-tetrahydronaphthalen-1-yl)-acetamide (5 g, 24 mmol), methylsulfonylchloride (6.9 g, 60 mmol) and pyridine (4.7 g, 60 mmol) in methylene chloride (100 mL) was heated at reflux for 8 h. The mixture was then cooled and washed with water. The organic layer was dried over magnesium sulfate, filtered and evaporated. The resulting solid was washed with diethyl ether and dried (3.8 g, 51% yield) without further purification.

EXAMPLE 10

Preparation of N-(7-azido-5,6,7,8-tetrahydronaphthalen-1-yl)-acetamide

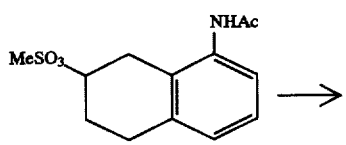

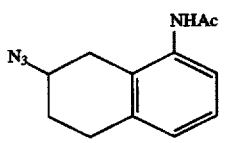

A mixture of methanesulfonic acid 8-acetylamino-1,2,3,4-tetrahydronaphthalen-2-yl ester (3.8 g, 13 mmol) and sodium azide (1.7 g, 27 mmol) in dimethylformamide (70 mL) was heated at 50° C. for 6 h. The solvent was removed by rotoevaporation in vacuo and the residue partitioned between methylene chloride and water. The organic layer was separated, dried over sodium sulfate, filtered and evaporated to give a dark solid. The product was purified by column chromatography on silica gel (1:1 ethyl acetate:hexane as eluant) to give a white solid (2.9 g) in 97% yield.

EXAMPLE 11

Preparation of N-(7-azido-4-bromo-5,6,7,8-tetrahydronaphthalen-1-yl)-acetamide

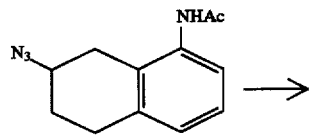

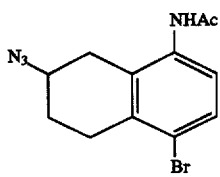

A solution of N-(7-azido-5,6,7,8-tetrahydronaphthalen-1-yl)-acetamide (1 g, 4.3 mmol) in acetic acid (40 mL) was treated dropwise with bromine (1 g, 6.5 mmol) and stirred at room temperature for 3 h. The solvent was evaporated and the solid residue was washed with ether, collected by filtration and dried to give the product (1.5 g) in 89% yield.

EXAMPLE 12

Preparation of N-(7-azido-4-bromo-2-nitro-5,6,7,8-tetrahydronaphthalen-1-yl) acetamide

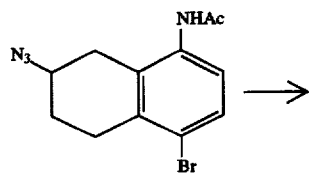

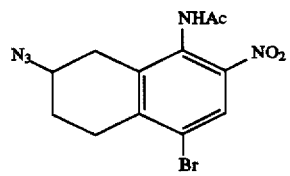

A solution of N-(7-azido-4-bromo-5,6,7,8-tetrahydronaphthalen-1-yl)-acetamide (1.5 g) was cooled in an ice bath and treated with fuming nitric acid (2 mL). After stirring for 2 h the solvent was removed by rotoevaporation and water was added to the residue to give a solid. The product was collected by filtration and dried (1.1 g, 81% yield).

EXAMPLE 13

Preparation of 7-azido-4-bromo-2-5,6,7,8-tetrahydronaphthalen-1-ylamine

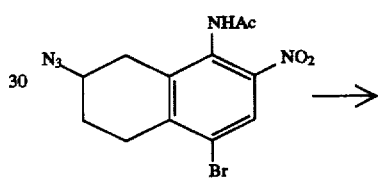

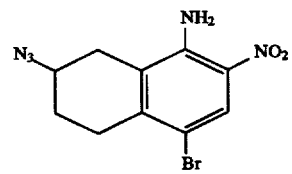

A mixture of N-(7-azido-4-bromo-2-nitro-5,6,7,8-tetrahydronaphthalen-1-yl)-acetamide, 2N HCl (150 mL) and acetic acid (30 mL) was heated at 85° C. for 48 h. The mixture was concentrated by rotoevaporation in vacuo, and the resulting solid was collected by filtration, washed with water and then dried to give the desired aniline (4.25 g) in 86% yield.

EXAMPLE 14

Preparation of 9-amino-1,4,7,8,9,10-hexahydro-benzo[f]quinoxaline-2,3-dione

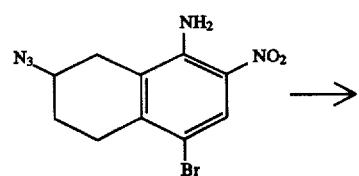

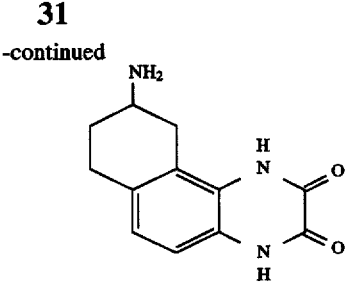

A solution of 7-azido-4-bromo-2-nitro-5,6,7,8-tetrahydronaphthalen-1-ylamine (1.7 g, 5.4 mmol) in tetrahydrofuran (50 mL) and methanol (50 mL) was treated with 20% palladium on charcoal (0.5 g) and shaken in a Parr apparatus under a hydrogen atmosphere (50 psi) for 15 h. The catalyst was removed by filtration, the filtrate was evaporated and the residue was dissolved in 2N HCl and treated with oxalic acid (1.7 g). After heating at 85° C. for 2.5 h, the solid that formed was collected by filtration and washed with methanol and dried in vacuo to give the product (1.02 g, 82% yield).

EXAMPLE 15

Preparation of 9-amino-6-nitro-1,4,7,8,9,10-hexahydro-benzo[f]quinoxaline-2,3-dione

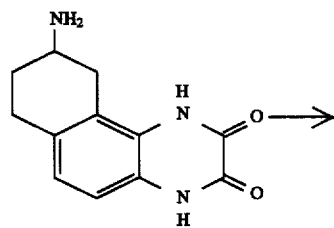

A mixture of 9-amino-1,4,7,8,9,10-hexahydrobenzo[f]quinoxaline-2,3-dione and trifluoroacetic acid (10 mL) was cooled in an ice bath and then treated with fuming nitric acid (0.5 mL) and stirred for 3 h at 0° C. and then 1 h at room temperature. After removing the solvent by rotoevaporation, the residue was triturated with acetone and the resulting solid collected by filtration to give the product (0.22 g, 93% yield). The solid was stirred in 2N HCl for 15 min, collected by filtration and dried to give the hydrochloride salt. Anal. calc'd for $C_{12}H_{12}N_4O_4 \cdot HCl \cdot H_2O$—C, 43.58; H, 4.57; N, 16.94; found -C, 43.56; H, 4.08; N, 16.51.

EXAMPLE 16

Preparation of piperidine-4-carboxylic acid (6-nitro-2,3-dioxo-1,2,3,4,7,8,9,10-octahydro-benzo[f]quinoxalin-9-yl) amide

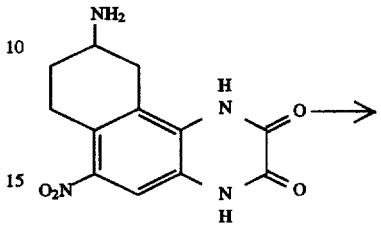

N-t-butyloxycarbonylpiperidine-4-carboxylic acid (0.35 g, 1.5 mmol) and carbonyldiimidazole (0.24 g, 1.5 mmol) were refluxed in tetrahydrofuran (5 mL) for 15 min. The mixture was added to a solution of 9-amino-6-nitro-1,4,7,8,9,10-hexahydro-benzo[f]quinoxaline-2,3-dione (0.15 g, 1.5 mmol) in dimethylformamide (5 mL) and heated to 70° C. After 15 min, triethylamine (0.15 g, 1.5 mmol) was added and heating continued at 70° C. for 6 h. The solvent was removed by rotoevaporation in vacuo and the residue triturated with diethyl ether to form a solid. The solid was collected by filtration, washed with water and dried to give the crude product (0.23 g, 94% yield). For further purification, the solid was suspended and stirred in 2N HCl, and then filtered and dried. Anal. calc'd for $C_{23}H_{29}N_5O_7 \cdot 1.5$ $NaCl \cdot H_2O$: C, 40.82; H, 4.57; N, 13.22; found-C, 40.35; H, 4.70:N, 12.91.

EXAMPLE 17

Preparation of N-(6-nitro-2,3-dioxo-1,2,3,4,7,8,9,10-octahydro-benzo[f]quinoxalin-9-yl)-acetamide

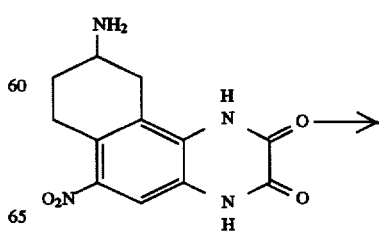

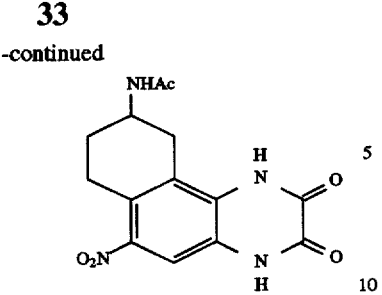

A mixture of 9-amino-6-nitro-1,4,7,8,9,10-hexahydro-benzo[f]quinoxaline-2,3-dione (0.15 g, 0.5 mmol), acetic anhydride (0.1 g, 1 mmol) and triethylamine (0.2 g, 2 mmol) in dimethylformamide (5 mL) was stirred at room temperature for 3 h. The solvent was removed by rotoevaporation, and the residue suspended in water and 2N HCl. The solid which formed was collected by filtration, washed with diethyl ether and dried to give the acetamide (0.14 g) in 88% yield. Anal. calc'd for $C_{14}H_{14}N_4O_5 \cdot H_2O$: C, 50.00; H, 4.80; N, 16.66; found-C, 49.92; H, 4.77; N, 16.04.

EXAMPLE 18

Preparation of N-7-benzyl-4-bromo-2-nitro-5,6,7,8-tetrahydronaphthalene-1,7-diamine

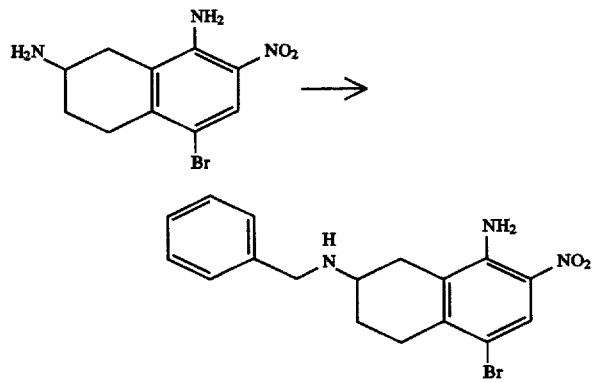

A solution of 1,7-diamino-2-nitro-4-bromotetralin hydrochloride (0.32 g, 1 mmol) and benzaldehyde (0.16 g, 1.5 mmol) in 2:1 methanol:water (10 mL) was stirred at room temperature and treated with sodium cyanoborohydride (0.19 g, 3 mmol). After stirring for 18 h, the mixture was concentrated and extracted with methylene chloride. The organic layer was dried over magnesium sulfate, filtered and evaporated to give a yellow solid. Purification was accomplished by silica gel chromatography (chloroform, then 2% methanol in chloroform as eluant) to give the benzylamine derivative (0.18 g).

EXAMPLE 19

Preparation of 9-benzylamino-6-bromo-1,4,7,8,9,10-hexahydro-benzo[f]quinoxaline-2,3-dione

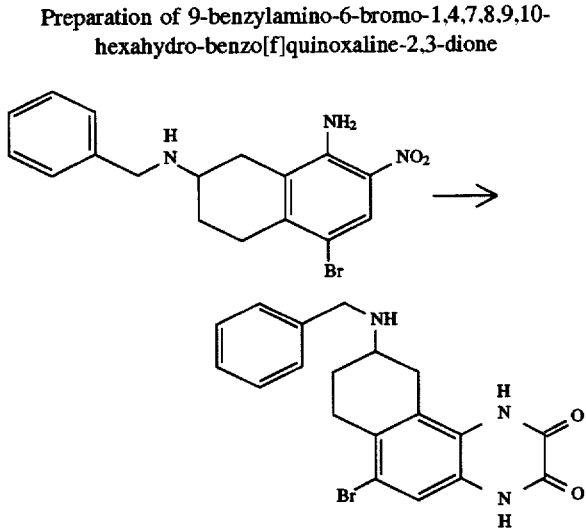

Raney nickel was deactivated by stirring with acetone and washing with tetrahydrofuran as before. A mixture of N-7-benzyl-4-bromo-2-nitro-5,6,7,8-tetrahydronaphthalene-1,7-diamine (0.18 g) and Raney nickel (0.5 g) in tetrahydrofuran (20 mL) was stirred under a hydrogen atmosphere (1 atm) for 30 min. The catalyst was removed by filtration and washed with excess tetrahydrofuran. The filtrate was evaporated to a white solid. The catalyst was washed further with 2N HCl and the filtrate was combined with the white solid from above and oxalic acid (0.6 g) and the mixture heated at 75° C. for 2 h. The solid that formed was collected by filtration and dried in vacuo. CI MS m/e (M+1) 400, 402. H-NMR (400 MHz, TFA): 1H, s, 12.05; 1H, s, 11.95; 1H, s, 7.7; 5H, s, 7.5; 1H, d, 4.8; 1H, d, 4.55; 1H, m, 3.95; 1H, m, 3.87; 2H, m, 3.2–2.4; 1H, m, 3.0–2.85; 1H, m, 2.6; 1H, m, 2.2–2.0.

EXAMPLE 20

Preparation of N-indan-2-yl-acetamide

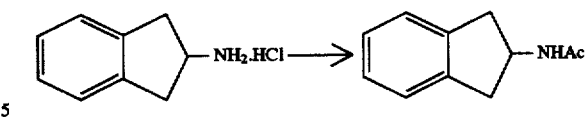

A mixture of 2-aminoindan hydrochloride (13.3 g, 78 mmol), acetic anhydride (6 g, 0.157 mmol) and saturated sodium bicarbonate (100 mL) in ether (100 mL) was stirred at room temperature for 1 h. The organic phase was separated, and the aqueous layer back washed with ether. The combined organic layer was washed with saturated chloride solution, dried over magnesium sulfate, filtered and evaporated to give the acetamide (13.6 g) in quantitative yield.

EXAMPLE 21

Preparation of N-(5-nitro-indan-2-yl)-acetamide

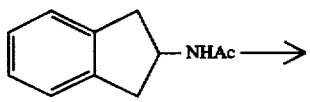

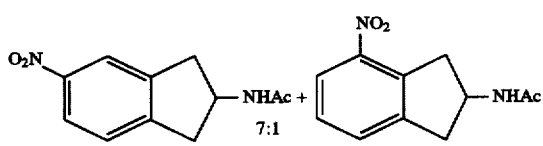

N-Indan-2-yl-acetamide (14 g, 80 mmol) was dissolved in trifluoroacetic acid (150 mL) and cooled in an ice bath to 0° C. Fuming nitric acid (20 mL) was added slowly via a pipette, and the mixture was stirred for 2 h while maintaining the temperature at 0°. After evaporating the solvent in vacuo, the residue was dissolved in a mixture of ether and water. The water layer was extracted several times with ether, and the combined organic layer was washed with saturated sodium chloride solution, dried over magnesium sulfate, filtered and evaporated to give the nitrated adduct(s) as a syrupy solid (20.5 g). This material (7:1 mixture by NMR) was used without further purification.

EXAMPLE 22

Preparation of N-(5-acetylamino-indan-2-yl)-acetamide

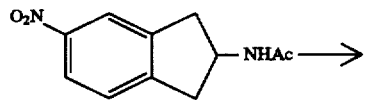

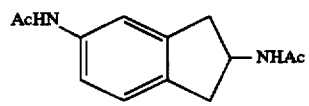

The mixture of N-(5-nitro-indan-2-yl)-acetamide (20.5 g, 93 mmol) in tetrahydrofuran (200 mL) was combined with acetic anhydride (10 mL) and Raney nickel (5 g) and stirred under an atmosphere of hydrogen gas (in a balloon) at room temperature for 24 h. Additional Raney nickel was added and the balloon recharged with hydrogen gas and stirred an additional 24 h. After removing the Raney nickel by filtration through a celite pad and washing with methanol several times, the filtrate was evaporated to a syrup. The residue was triturated with ether/water and the resulting white solid collected by filtration (9.2 g, 52% yield overall from 2-aminoindan, prepared in Example 20).

EXAMPLE 23

Preparation of N-(5-acetylamino-6-bromo-indan-2-yl)acetamide

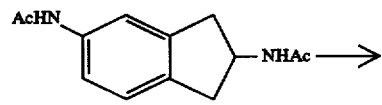

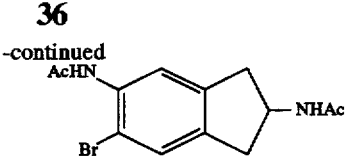

A solution of N-(5-acetylamino-indan-2-yl)-acetamide (9.8 g, 42 mmol) and bromine (8.5 g, 53 mmol) in acetic acid (200 mL) was stirred at room temperature for 3 h. After evaporation of the solvent, the syrupy residue was dissolved in ether and washed with water. The organic layer was washed with aqueous sodium bisulfite and dried over magnesium sulfate. The solvent was concentrated and the resulting solid collected by filtration (10 g, 77% yield).

EXAMPLE 24

Preparation of N-(5-acetylamino-6-bromo-4-nitro-indan-2-yl)-acetamide

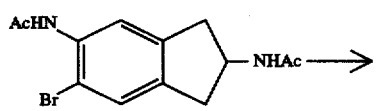

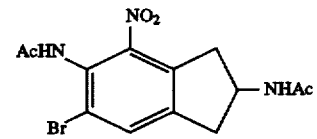

A solution of N-(5-acetylamino-6-bromo-4-indan-2-yl) acetamide (10 g, 32 mmol) in trifluoroacetic acid (175 mL) was cooled in an ice bath to 0° C. and then treated with fuming nitric acid (25 mL). After stirring for 2 h at 0° C., the reaction mixture was warmed to room temperature and stirred for an additional 2 h. The solvent was removed by rotoevaporation and the residue was triturated with an ether/water mixture. The resulting solid was collected by filtration and washed consecutively with water and ether, and then dried in vacuo to give the product (10 g) in 87% yield.

EXAMPLE 25

Preparation of N-(5-amino-6-bromo-4-nitro-indan-2-yl)acetamide

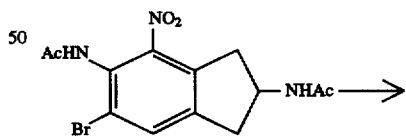

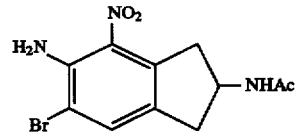

N-(5-Acetylamino-6-bromo-4-nitro-indan-2-yl)-acetamide (1 g, 2.8 mmol) was suspended in a 2:1 mixture of sulfuric acid and water (30 mL) and heated at 90° C. for 12 h. The mixture was poured onto ice and the resulting yellow solid was collected by filtration and dried in vacuo to give (0.7 g, 80% yield).

EXAMPLE 25

Preparation of 6-bromo-4-nitro-indan-2,5-diamine monohydrochloride

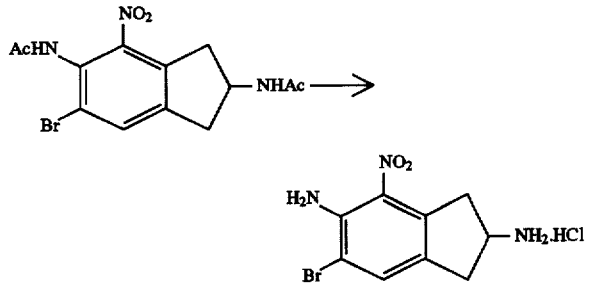

N-(5-Acetylamino-6-bromo-4-nitro-indan-2-yl)-acetamide (1 g, 2.8 mmol) was stirred in 3N HCl (80 mL) at reflux for 3 h. The resulting solid was collected by filtration and dried in vacuo. Additional material was obtained by evaporation of the filtrate to give a combined yield of 93% of the yellow orange product (0.8 g).

EXAMPLE 27

Preparation of N-(4,5-diamino-6-bromo-indan-2-yl) acetamide

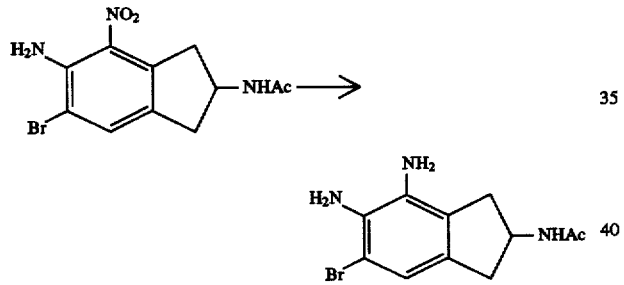

N-(5-Amino-6-bromo-4-nitro-indan-2-yl)-acetamide (0.7 g, 2.2 mmol) was dissolved in tetrahydrofuran (20 mL) and then treated with Raney nickel and stirred under a hydrogen atmosphere (1 atm) at room temperature for 1 h. The catalyst was removed by filtration through a celite pad, and washed repeatedly with methanol. The combined organic filtrate was removed by rotoevaporation to give a syrup that solidified upon standing. This product was used without further purification.

EXAMPLE 28

Preparation of N-(5-bromo-2,3-dioxo-2,3,4,7,8,9-hexahydro-1H-cyclopenta[f]quinoxalin-8-yl)-acetamide

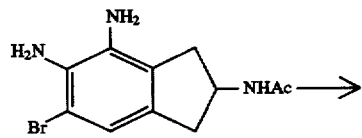

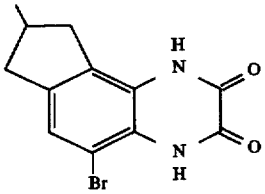

N-(4,5-Diamino-6-bromo-indan-2-yl)-acetamide (~2.2 mmol) was combined with oxalic acid (0.5 g) in 2N HCl (15 mL) and heated at 80° C. for 3 h. The resulting precipitate was collected by filtration and washed consecutively with methanol, water and ether, and then dried in vacuo to give the quinoxalinedione (0.37 g) in 50% yield for the hydrogenation and condensation steps. CHN calc'd for $C_{13}H_{12}BrN_3O_3 \cdot 2.2H_2O$: C, 41.33; H, 4.37; N, 11.12; Found: C, 41.12; H, 3.91; N, 11.24.

EXAMPLE 29

Preparation of N-(5-bromo-6-nitro-2,3-dioxo-2,3,4,7,8,9-hexahydro-1H-cyclopenta[f]quinoxalin-8-yl) acetamide N-(5-Bromo-2,3-dioxo-2,3,4,7,8,9-hexahydro-1H-cyclopenta[f]quinoxalin-8-yl)-acetamide (0.24 g, 0.7 mmol) was dissolved in trifluoroacetic acid (10 mL), cooled in an ice bath to 0° C., and then treated with fuming nitric acid (0.5 mL) and stirred for 4 h at 0° C. After removing the solvent by rotoevaporation, the syrupy residue was triturated with water and the resulting solid was collected by filtration, washed with water and then ether and dried in vacuo (0.22 g, 81% yield). Anal. calc'd for $C_{13}H_{11}BrN_4O_5 \cdot H_2O$: C, 38.92; H, 3.27; N, 13.94. Found: C, 38.60; H, 3.00; N, 13.66.

EXAMPLE 30

Preparation of N-(2,3-dioxo-2,3,4,7,8,9-hexahydro-1H-cyclopenta[f]quinoxalin-8-yl)-acetamide

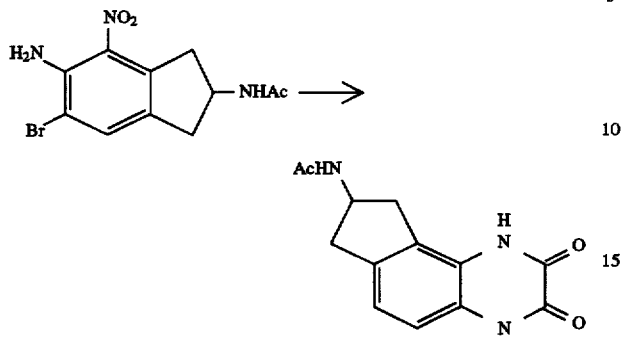

A mixture of N-(5-amino-6-bromo-4-nitro-indan-2-yl) acetamide (0.5 g, 1.6 mmol), 5% palladium on carbon (0.2 g) and sodium acetate (0.16 g) in methanol (75 mL) was placed on a Parr hydrogenation apparatus under a hydrogen atmosphere (51 psi) and shaken for 18 h. After removing the catalyst by filtration, the solvent was evaporated and the residue was suspended in 2N HCl, treated with oxalic acid (0.5 g) and then heated at 80° C. for 4 h. The water was evaporated and the residue dissolved in saturated sodium bicarbonate and acetic anhydride (1 mL) was added. The resulting solid was collected by filtration and dried in vacuo to give a brown solid (0.15 g) in 36% yield.

EXAMPLE 31

Preparation of N-(2,3-dioxo-2,3,4,7,8,9-hexahydro-1H-cyclopenta[f]quinoxalin-8-yl)-acetamide

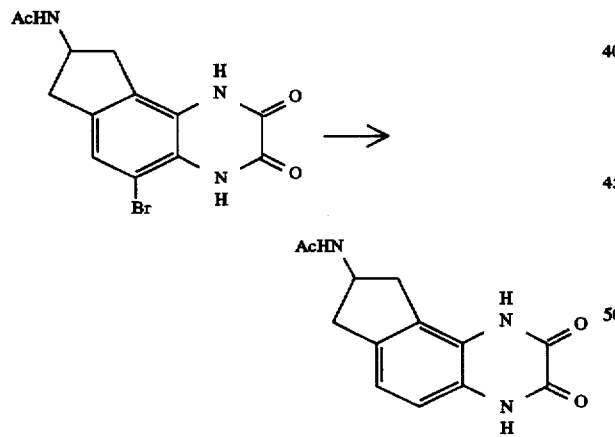

N-(5-Bromo-2,3-dioxo-2,3,4,7,8,9-hexahydro-1H-cyclopenta[f]quinoxalin-8-yl)-acetamide (1 g, 3 mmol) was dissolved in dimethylformamide (75 mL) and treated with potassium acetate (0.33 g) and 20% palladium on carbon (0.2 g) and shaken on a Parr apparatus under a hydrogen atmosphere (51 psi) for 7 min. The catalyst was removed by filtration, the filtrate evaporated and the residue triturated in water. The resulting solid was collected by filtration and dried in vacuo to give the debrominated product (0.75 g) in 98% yield. Anal. Calc'd for $C_{13}H_{13}N_3O_3 \cdot 1.7 H_2O$: C, 53.85; H, 5.70; N, 14.49. Found: C, 53.87; H, 5.04; N, 14.15.

EXAMPLE 32

Preparation of N-(6-nitro-2,3-dioxo-2,3,4,7,8,9-hexahydro-1H-cyclopenta[f]quinoxalin-8-yl)-acetamide

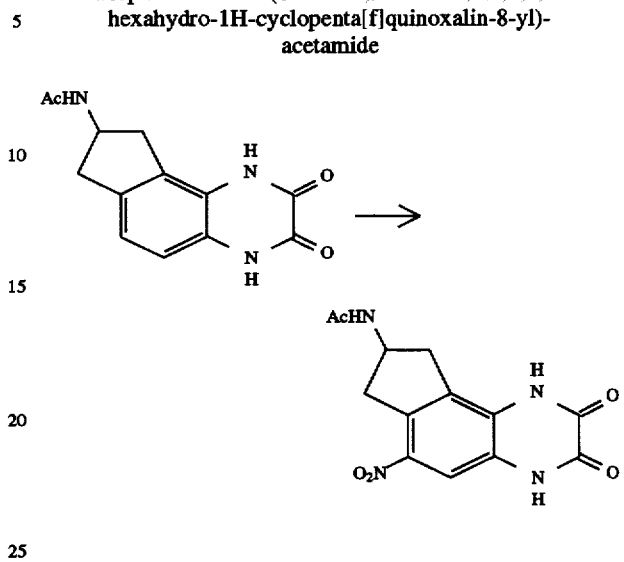

A mixture of N-(2,3-dioxo-2,3,4,7,8,9-hexahydro-1H-cyclopenta[f]quinoxalin-8-yl)-acetamide (0.15 g, 0.6 mmol), potassium nitrate (0.07 g, 0.7 mmol) and sulfuric acid (5 mL) was stirred at room temperature for 3 h. After pouring onto ice, the aqueous solution was saturated with sodium chloride and allowed to stand overnight. The resulting precipitate was collected by filtration, washed with water and dried in vacuo to give a solid (35 mg, 19% yield). Anal. calc'd for $C_{13}H_{12}N_4O_5 \cdot 0.75$ NaCl: C, 44.85; H, 3.47; N, 16.09. Found: C, 45.18; H, 3.87; N, 15.87.

EXAMPLE 33

Preparation of 8-amino-4,7,8,9-tetrahydro-1H-cyclopenta[f]quinoxaline-2,3-dione hydrochloride

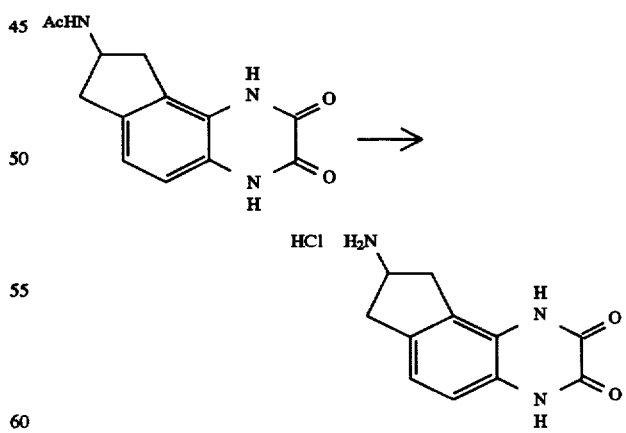

N-2,3-Dioxo-2,3,4,7,8,9-hexahydro-1H-cyclopenta[f] quinoxalin-8-yl)-acetamide (0.5 g, 1.9 mmol) was stirred in 2N HCl (20 mL) at reflux for 72 h. The solid was collected by filtration and dried in vacuo (0.4 g, 83% yield).

EXAMPLE 34

Preparation of 4-(2,3-dioxo-2,3,4,7,8,9-hexahydro-1H-cyclopenta[f]quinoxalin-8-ylcarbamoyl)-piperidine-1-carboxylic acid tert-butyl ester

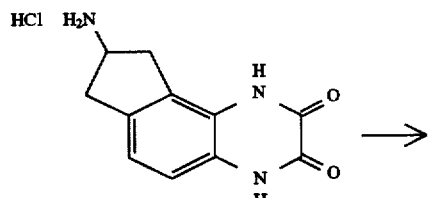

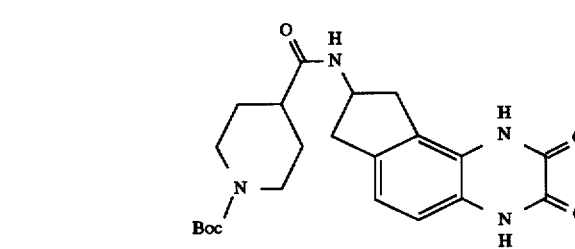

A mixture of N-Boc-piperidine-4-carboxylic acid (0.23 g, 1 mmol) and 1,1'-carbonyldiimidazole (0.16 g, 1 mmol) in tetrahydrofuran (5 mL) was heated at 80° C. for 15 min. After cooling, it was added to a solution of 8-amino-4,7,8,9-tetrahydro-1H-cyclopenta[f]quinoxaline-2,3-dione hydrochloride (0.11 g, 0.5 mmol) and the mixture was heated at 70° C. for 2 days. After filtration to remove precipitate, the filtrate was evaporated and the residue suspended in water. The resulting solid was collected by filtration, washed with diethyl and dried in vacuo (0.15 g, 70% yield).

EXAMPLE 35

Preparation of 4-(6-nitro-2,3-dioxo-2,3,4,7,8,9-hexahydro-1H-cyclopenta[f]quinoxalin-8-ylcarbamoyl)piperidine hydrochloride

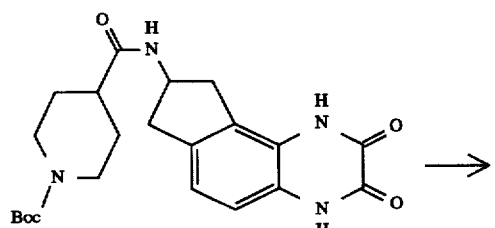

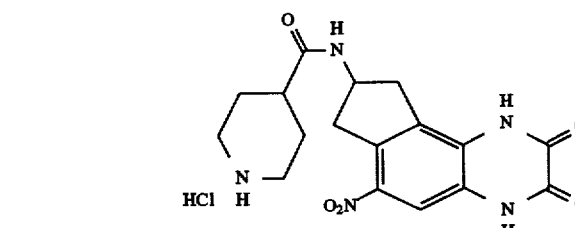

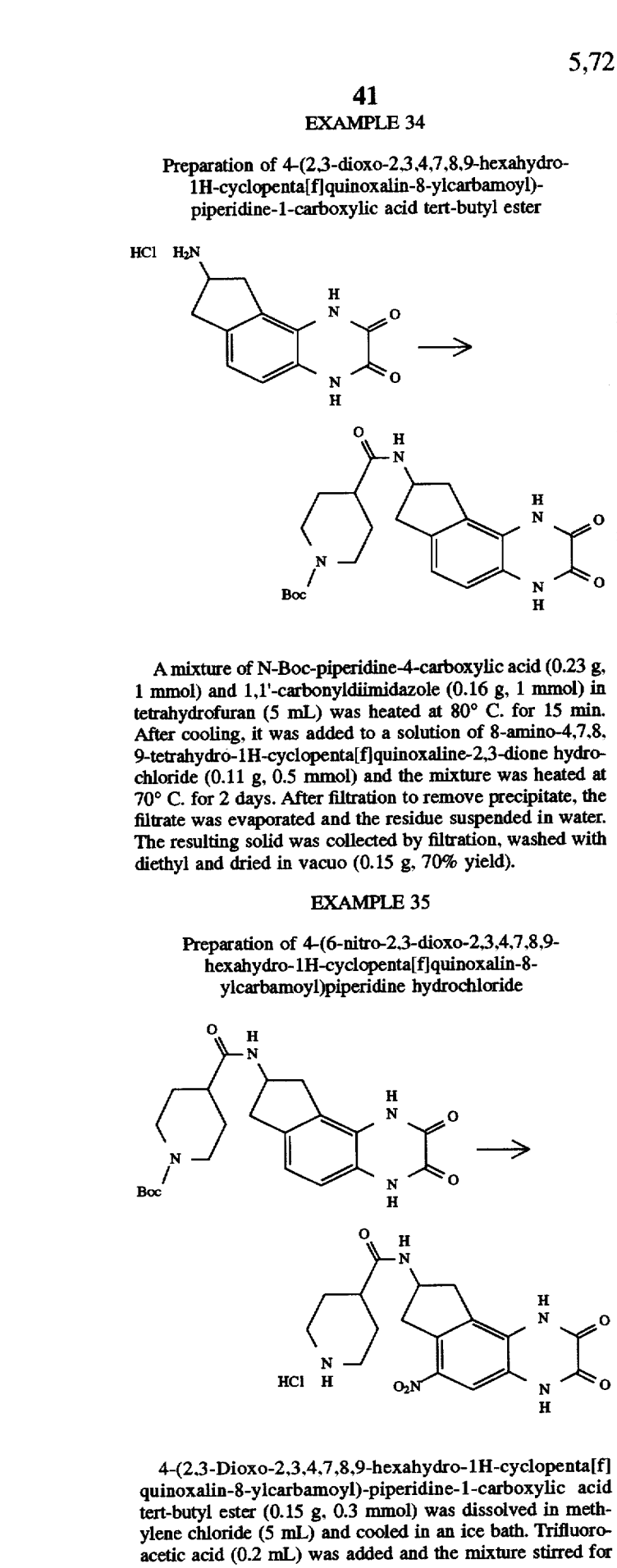

4-(2,3-Dioxo-2,3,4,7,8,9-hexahydro-1H-cyclopenta[f] quinoxalin-8-ylcarbamoyl)-piperidine-1-carboxylic acid tert-butyl ester (0.15 g, 0.3 mmol) was dissolved in methylene chloride (5 mL) and cooled in an ice bath. Trifluoroacetic acid (0.2 mL) was added and the mixture stirred for 20 min. The solvent was evaporated and the residue dissolved in trifluoroacetic acid (5 mL), cooled in an ice bath and treated with fuming nitric acid (0.5 ML), stirred for 2 h at 0° C. and then warmed to room temperature for an additional 1 h. The trifluoroacetic acid was removed by rotoevaporation, and the residue triturated with 2N HCl. The resulting solid was collected by filtration and dried in vacuo (60 mg, 42% yield).

EXAMPLE 36

Preparation of N-(6-nitro-2,3-dioxo-1,2,3,4,7,8,9,10-octahydrobenzo[f]quinoxalin-9-yl)-benzamide

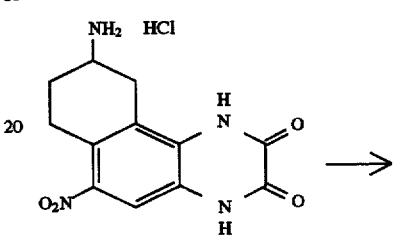

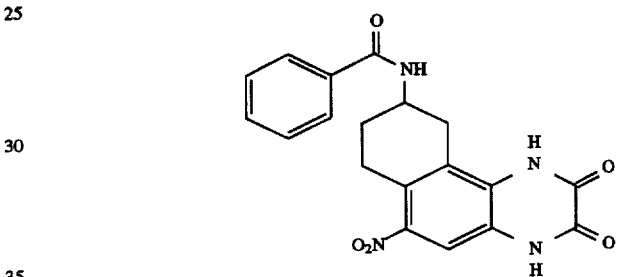

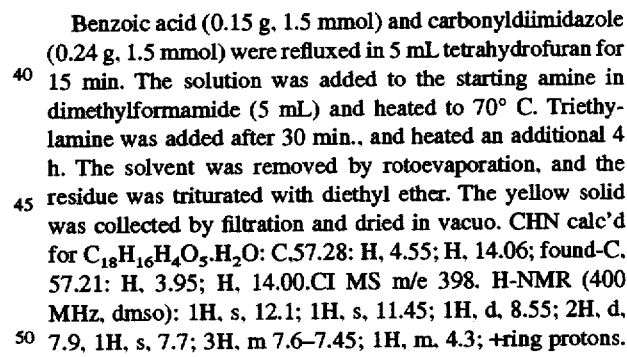

Benzoic acid (0.15 g, 1.5 mmol) and carbonyldiimidazole (0.24 g, 1.5 mmol) were refluxed in 5 mL tetrahydrofuran for 15 min. The solution was added to the starting amine in dimethylformamide (5 mL) and heated to 70° C. Triethylamine was added after 30 min., and heated an additional 4 h. The solvent was removed by rotoevaporation, and the residue was triturated with diethyl ether. The yellow solid was collected by filtration and dried in vacuo. CHN calc'd for $C_{18}H_{16}H_4O_5 \cdot H_2O$: C,57.28; H, 4.55; H, 14.06; found-C, 57.21: H, 3.95; H, 14.00.Cl MS m/e 398. H-NMR (400 MHz, dmso): 1H, s, 12.1; 1H, s, 11.45; 1H, d, 8.55; 2H, d, 7.9, 1H, s, 7.7; 3H, m 7.6–7.45; 1H, m, 4.3; +ring protons.

EXAMPLE 37

Preparation of N-(6-nitro-2,3-dioxo-1,2,3,4,7,8,9,10-octahydrobenzo[f]quinoxalin9-yl)cyclohexylamide

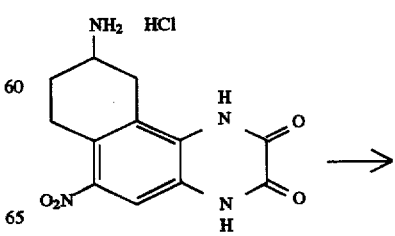

-continued

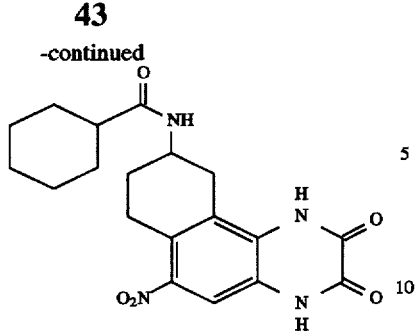

Cyclohexanecarboxylic acid (0.13 g, 1 mmol) and carbonyldiimidazole (0.16 g, 1 mmol) were refluxed in 2 mL tetrahydrofuran for 15 min. The solution was added to the starting amine in dimethylformamide (2 mL) and heated to 60° C. Triethylamine was added after 30 min, and heated an additional 16 h at 60° C. The solvent was removed by rotoevaporation, and the residue was taken up in 2N HCl. The yellow solid was collected by filtration and dried in vacuo to give 90 mg material. CHN calc'd for $C_{18}H_{22}N_4O_5 \cdot 0.75H_2O$: C, 57.06; H, 5.92; N, 14.01; found- C, 57.11; H, 5.50; N, 13.63. CI MS m/e 387. H-NMR (400 MHz, dmso): 1H, s, 12.1; 1H, s, 11.45; 1H, d, 7.85; 1H, s, 7.7; 1H, m, 4.0; +ring protons.

EXAMPLE 38

Preparation of 8-amino-6-nitro-4,7,8,9-tetrahydro-1H-cyclopenta[f]quinoxaline-2,3-dione hydrochloride

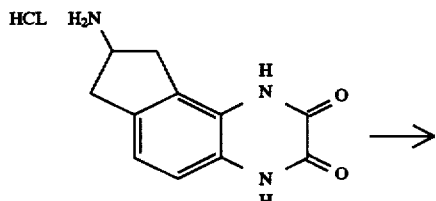

The parent quinoxalinedione (Example 33) was mixed with 50 mL trifluoroacetic acid and 1 mL fuming nitric acid at 0° C. and stirred for 3 h, then warmed to room temperature for 2 h. The solvent was evaporated, the residue taken up in acetone, and the solid collected by filtration. After washing with water and then tetrahydrofuran, the material was dried to give 1.3 g of the compound as the hydrochloride salt. CHN calc'd for $C_{11}H_{10}N_4O_4 \cdot HCl \cdot 0.5H_2O$: C, 38.39; H, 3.52; N, 16.28; found-C, 38.54; H, 3.57; N, 17.39. CI MS m/e (M+1) 263. H-NMR (400 MHz, dmso) 1H, s, 12.2; 1H, s, 12.12; 2H, br s, 8.1; 1H, s, 7.9; 1H, br s, 4.2; 1H, dd, 3.7; 2H, m, 3.4; 1H dd, 3.1.

EXAMPLE 39

Preparation of N-(6-nitro-2,3-dioxo-4,7,8,9-tetrahydro-1H-cyclopenta[f]quinoxalin-8-yl)-benzamide

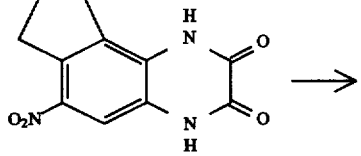

The product of Example 38 (0.13 g, 0.5 mmol), benzoic anhydride (0.23 g, 1 mmol) and triethylamine (0.1 g) were combined in 5 mL dimethylformamide and stirred at room temperature for 24 h. The solvent was evaporated, the residue washed with methanol, collected by filtration and dried to give 0.1 g. CHN calc'd for $C_{18}H_{14}N_4O_5 \cdot H_2O$: C, 56.24; H, 4.20; N, 14.58; found-C, 56.33; H, 3.82; N, 14.32. CI MS m/e 367. H-NMR (400 MHz, dmso) 1H, s, 12.18; 1H, s, 11.95; 1H, d, 8.7; 3H, m, 7.82; 3H, m, 7.55–7.4; 1H, m, 4.8; +ring protons.

EXAMPLE 40

Preparation of 4-(6-nitro-2,3-dioxo-1,2,3,4,7,8,9,10-octahydrobenzo[f]quinoxaline-9-ylcarbamoyl)-piperidine hydrochloride

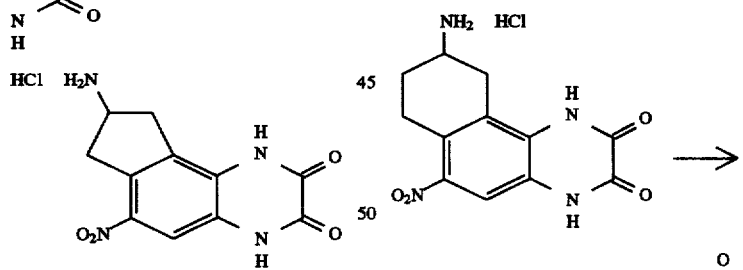

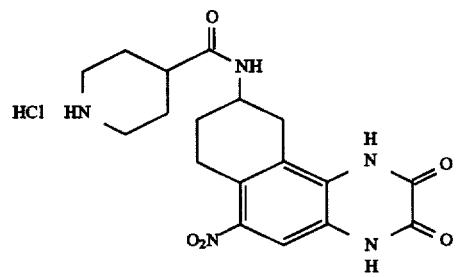

A mixture of N-Boc-piperidine-4-carboxylic acid (0.92 g, 4 mmol) and carbonyldiimidazole (0.65 g, 4 mmol) in 10 mL tetrahydrofuran was heated at reflux for 15 min. The mixture was added to the starting amine (Example 15, 0.6 g, 2 mmol)

in 10 mL dimethylformamide and heated at 70° C. for 30 min. Triethylamine (0.4 g) was added and the mixture heated an additional 18 h. The solvent was evaporated and the yellow solid was washing with tetrahydrofuran, collected by filtration and dried to give 0.74 g. The solid was suspended in 50 mL methylene chloride, cooled in an icebath and treated with trifluoroacetic acid (1 g). After evaporating the solvent, the solid was washed with ether and acetone mixture and dried. Calc'd for $C_{18}H_{21}N_5O_5 \cdot 1.5HCl \cdot H_2O$: C, 40.82; H, 4.57; N, 13.22; found-C, 40.35; H, 4.70; N, 12.91.

EXAMPLE 41

Preparation of 2-(6-nitro-2,3-dioxo-1,2,3,4,7,8,9,10-octahydrobenzo[f]quinoxaline-9-ylcarbamoyl)ethyl-(4-hydroxy)benzene

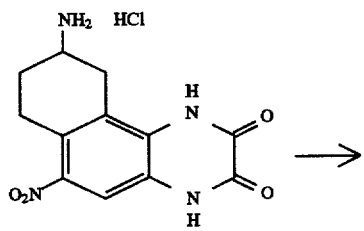

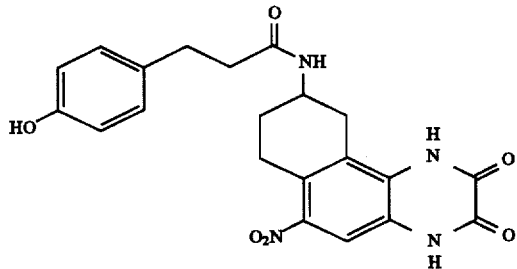

Hydroxyphenylpropionic acid (0.17 g, 1 mmol) and carbonyldiimidazole (0.16 g, 1 mmol) in 5 mL tetrahydrofuran were stirred at reflux for 15 min. The mixture was added to the starting amine (example 15, 0.15 g, 0.5 mmol) and heated at 60° C. for 30 min. Triethylamine (0.1 g) was added and the mixture heated an additional 5 h. The solvent was removed by rotoevaporation, and the residue suspended in tetrahydrofuran. The solid was collected by filtration and dried. CI MS m/e (M+1) 425. H-NMR (400 MHz, dmso) 1H, s, 12.1; 1H, s, 11.45; 5 Ar H, 8.0–6.6 including 1H, s, 7.65; 1H, m, 4.1; +other ring protons.

EXAMPLE 42

Preparation of N-phenyl-N'-(6-nitro-2,3-dioxo-1,2,3,4,7,8,9,10-octahydrobenzo[f]quinoxalin-9-yl)urea

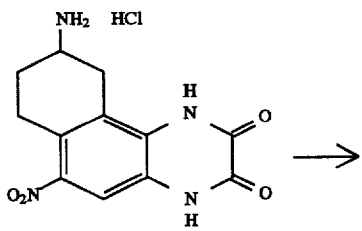

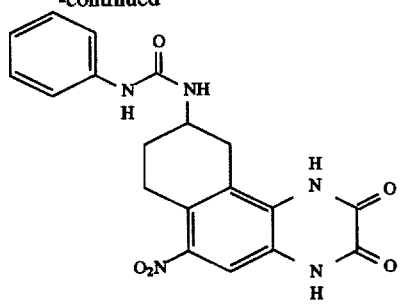

The product of Example 15 (0.15 g, 0.5 mmol), phenylisocyanate (0.1 g, 1 mmol) and triethylamine (0.1 g) in 5 mL dimethylformamide were stirred at room temperature for 18 h. The solvent was removed by rotoevaporation and the residue suspended in methanol/dimethylformamide. After heating, the solid was collected by filtration and dried in vacuo. CHN calc'd for $C_{19}H_{17}N_5O_5 \cdot 0.5H_2O \cdot HCON(Me)_2$: C, 55.34; H, 5.27; N, 17.60 found-C, 55.38; H, 4.95; N, 17.04. H-NMR (400 MHz, dmso) 1H, s, 12.1; 1H, s, 11.45; 1H, s, 8.4; 1H, s, 7.95; 1H, s, 7.7; 2H, d, 7.4; 2H, t, 7.23; 1H, t, 6.9 1H, d, 6.35; 1H, t, 4.1; +ring protons.

EXAMPLE 43

8-Acetamido-2-methoxynaphthalene

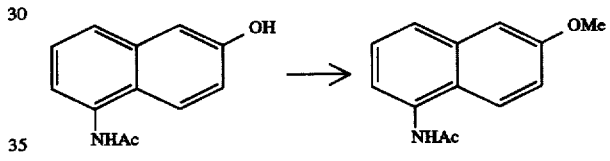

A mixture of 8-Acetamido-2-naphthol (21 g, 0.104 mol), dimethyl sulfate (15.1 g, 0.12 mol) and potassium carbonate (41 g, 0.3 mol) in acetone (200 mL) was stirred at room temperature for 48 h. Solids were removed by filtration and washed with methanol, and the filtrate evaporated. The residue was washed in 1:1 hexane:toluene, collected by filtration and dried (24.7 g).

EXAMPLE 44

8-Acetamido-2-tetralone

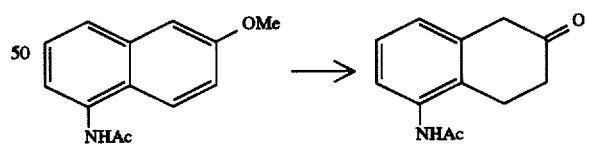

Ammonia (300 mL) was condensed in a flask containing 8-Acetamido-2-methoxynaphthalene (24.5 g, 115 mmol), t-butyl alcohol (34 g, 0.46 mol) and THF (300 mL). Sodium (8 g, 0.35 mol) was added in portions and the mixture was stirred for 3 h and allowed to warm to room temperature. The mixture was poured onto ice and saturated sodium chloride, and then extracted with THF (3×). The combined organic layers were washed with saturated sodium chloride, dried over magnesium sulfate, filtered and evaporated to give a dark solid. The residue was dissolved in 50% acetic acid and heated at 95° C. for 18 h. After evaporation, the residue was suspended in dimethyl ether and collected by filtration and dried. The filtrate was purified by silica gel chromatography (3:2 EtOAc:hexane) and combined with the other product to give a tan solid (10 g).

EXAMPLE 45

1-Acetamido-7-benzylamino-5,6,7,8-tetrahydronaphthalene

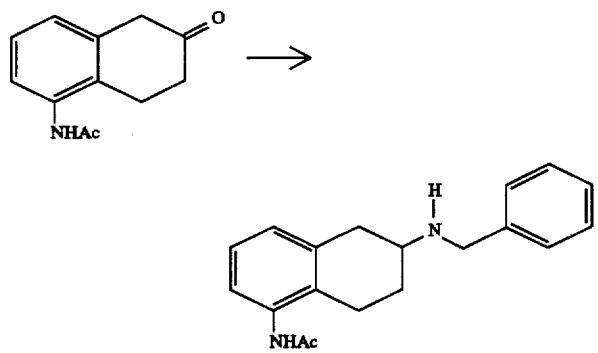

A solution of 8-acetamido-2-tetralone (15.5 g, 76 mmol), benzylamine (16.3 g, 150 mmol) and tosic acid (0.2 g) in benzene (200 mL) and DMF (50 mL) was refluxed with a Dean-Stark trap attached for 18 h. The solvent was evaporated and the residue dissolved in 1:1 methanol:THF (250 mL). After cooling in an ice bath, sodium cyanoborohydride was added and the mixture warmed to room temperature and stirred for 5 h. The mixture was basified with 12.5% NaOH and the solvent concentrated. The residue was dissolved in methylene chloride:water and filtered through a celite pad. The aqueous layer was extracted with methylene chloride, and the combined organic layers were dried over sodium sulfate, filtered and evaporated. The dark residue was purified by column chromatography (9:1 EtOAc:methanol) to give the product (15 g).

EXAMPLE 46

1-Acetamido-7-benzylmethylamino-5,6,7,8-tetrahydronaphthalene

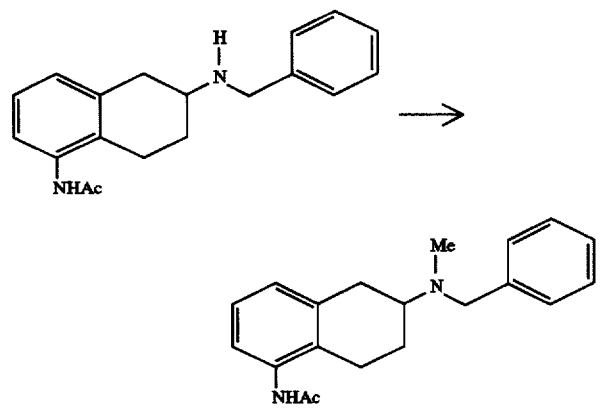

A mixture of 1-acetamido-7-benzylamino-5,6,7,8-tetrahydronaphthalene (14.3 g, 50 mmol), paraformaldehyde (15 g, 0.5 mol) and sodium cyanoborohydride (15.7 g, 0.25 mol) in acetic acid (250 mL) was stirred at room temperature for 48 h. The solvent was removed and the residue taken up in water:diethyl ether. The aqueous phase was basified with 12.5% NaOH and back extracted with ether. The combined ether layers were washed with saturated NaCl, dried over magnesium sulfate, filtered and evaporated to give a viscous syrup (16 g).

EXAMPLE 47

1,7-Bis($N^7$-methyl)acetamido-5,6,7,8-tetrahydronaphthalene

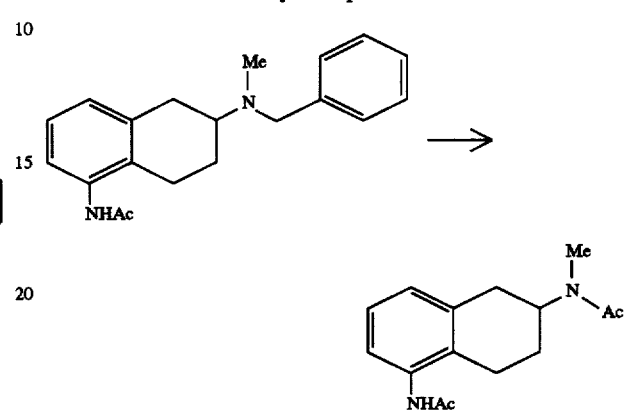

A mixture of 1-acetamido-7-benzylmethylamino-5,6,7,8-tetrahydronaphthalene (14 g, 45 mmol) and 20% Pd/C(3 g) in acetic acid (200 mL) was shaken on a Parr hydrogenation apparatus under a hydrogen atmosphere (50 psi) for several hours (hydrogen replaced periodically). After removing the catalyst the solvent was evaporated and the residue portioned between methylene chloride and water. The aqueous layer was basified with 12.5% NaOH and back extracted. The combined organic layers were dried over sodium sulfate, filtered and evaporated. The residue was purified by column chromatography (gradient from 30–100% methanol in EtOAc) to give the methylamine adduct (7.4 g) as a clear solid. The methylamine (5 g, 23 mmol) was dissolved in THF (50 mL) and treated with acetic anhydride (6 g, 60 mmol) and the mixture stirred at room temperature for 1 h. The solvent was removed, and the residue triturated with dimethyl ether and the solid collected by filtration and dried (5.6 g).

EXAMPLE 48

1,7-Bis($N^7$-methyl)acetamido-4-bromo-5,6,7,8-tetrahydronaphthalene

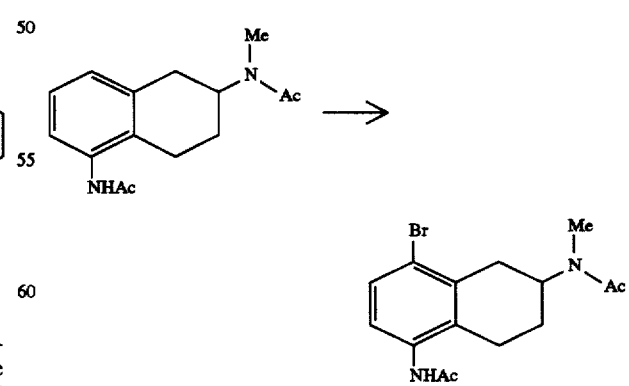

A solution of 1,7-bis($N^7$-methyl)acetamido-5,6,7,8-tetrahydronaphthalene (7 g, 27 mmol) and sodium acetate trihydrate (5.5 g, 51 mmol) in acetic acid (100 mL) was treated with bromine (5.2 g, 32 mmol) and stirred at room temperature for 18 h. Sodium bisulfite was added and the solvent remove. The residue was taken up in water:methylene chloride and the aqueous phase back extracted. The combined organic layers were evaporated to give an off-white solid. This was washed with dimethyl ether and dried to give the product (8.5 g) as a white solid.

EXAMPLE 49

1,7-Bis(N$^7$-methyl)acetamido-4-bromo-2-nitro-5,6,7,8-tetrahydronaphthalene

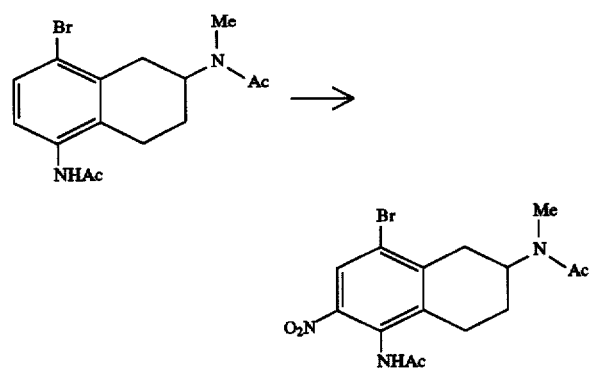

A mixture of 1,7-bis(N$^7$-methyl)acetamido-4-bromo-5,6,7,8-tetrahydronaphthalene (8.5 g, 25 mmol) in trifluoroacetic acid (100 mL) was cooled in an ice bath and treated with fuming nitric acid (10 mL). The reaction mixture was warmed to room temperature after 1 h and stirred for 3 h longer. The solvent was removed and the residue taken up in methylene chloride:water. The aqueous layer was backed extracted and the combined organic layers were dried over sodium sulfate, filtered and evaporated to give the product as a yellow syrup (9.2 g).

EXAMPLE 50

1,7-Di(N$^7$-methyl)amino-4-bromo-2-nitro-5,6,7,8-tetrahydronaphthalene hydrochloride

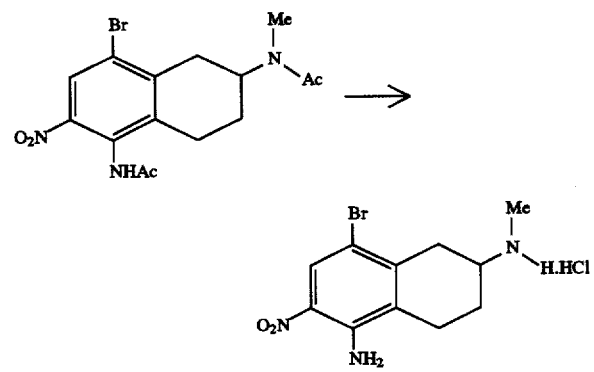

1,7-Di(N$^7$-methyl)amino-4-bromo-2-nitro-5,6,7,8-tetrahydronaphthalene was hydrolyzed in 3N HCl (100 mL) and acetic acid (20 mL) at 100° C. for 72 h. The mixture was cooled in an ice bath for 1 h, and the orange precipitate collected by filtration and dried (7.6 g).

EXAMPLE 51

9-Methylamino-1,4,7,8,9,10-hexahydrobenzo[f]quinoxaline-2,3-dione hydrochloride

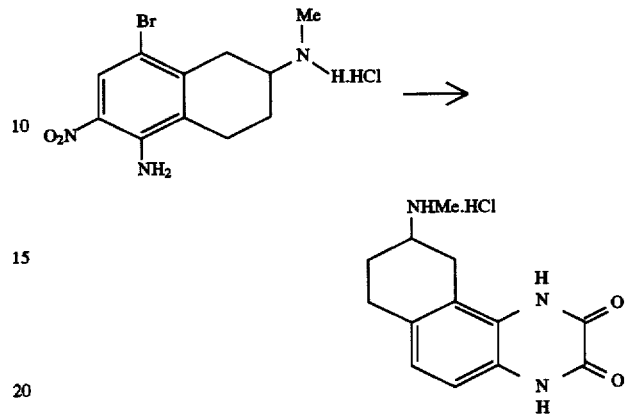

A mixture of 1,7-di(N$^7$-methyl)amino-4-bromo-2-nitro-5,6,7,8-tetrahydronaphthalene hydrochloride (7.6 g, 23 mmol) and 20% Pd/C (1 g) in methanol (250 mL) was shaken on a Parr hydrogenator under a hydrogen atmosphere (52 psi) for 18 h. After removing the catalyst, the solvent was removed and the residue dissolved in 2N HCl (100 mL). Oxalic acid (6.3 g, 50 mmol) was added and the reaction heated at 100° C. for 3 h. After cooling to room temperature, the precipitate was collected by filtration and dried.

EXAMPLE 52

9-Methylamino-6-nitro-1,4,7,8,9,10-hexahydrobenzo[f]quinoxaline-2,3-dione

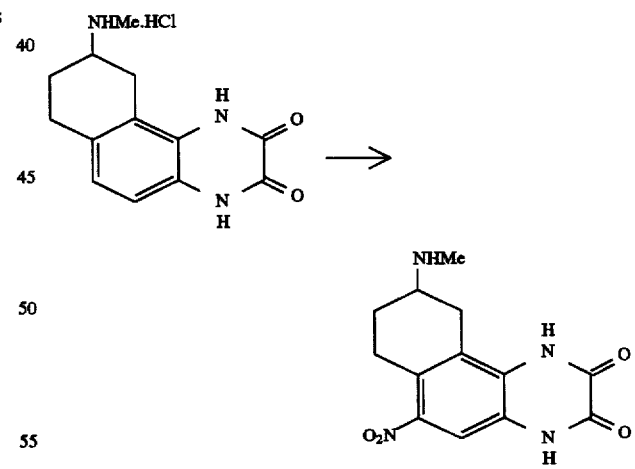

9-Methylamino-1,2,3,4,7,8,9,10-octahydrobenzo[f]quinoxaline-2,3-dione hydrochloride (1 g, 3.5 mmol) was nitrated using fuming nitric acid (1 mL) and trifluoroacetic acid (30 mL) from 0° C. to room temperature for 1 h. The solvent was removed and their residue triturated in acetone:water and collected by filtration and dried to give the product (1.1 g). Calc'd for $C_{13}H_{14}N_4O_4 \cdot HCl$: C, 47.79; H, 4.63; N, 17.15; found: C, 43.36; H, 4.22; N, 18.85. MS M+1 (291).

EXAMPLE 53

N-Methyl-N-(6-nitro-2,3-dioxo-1,2,3,4,7,8,9,10-octahydro-benzo[f]quinoxalin-9-yl)-benzamide

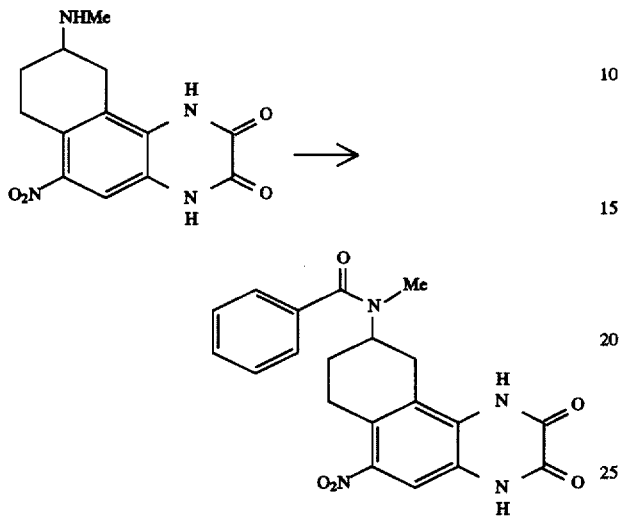

A mixture of 9-Methylamino-6-nitro-1,2,3,4,7,8,9,10-octahydrobenzo[f]quinoxaline-2,3-dione (0.16 g, 0.5 mmol), benzoic anhydride (0.22 g, 1 mmol) and triethylamine (0.1 g, 1 mmol) in DMF (5 mL) was stirred at room temperature for 18 h. The solvent was removed, and the residue suspended in 2N HCl. The solid was collected by filtration, washed successively with water and dimethyl ether and dried. Calc'd for $C_{20}H_{18}N_4O_5 \cdot H_2O$: C, 59.81; H, 4.72; N, 13.95; found: C, 59.98; H, 4.60; N, 13.60.

EXAMPLE 54

Thiophene-2-carboxylic acid (6-nitro-2,3-dioxo-2,3,4,7,8,9-hexahydro-1H-cyclopenta[f]quinoxaline-8-yl)-amide

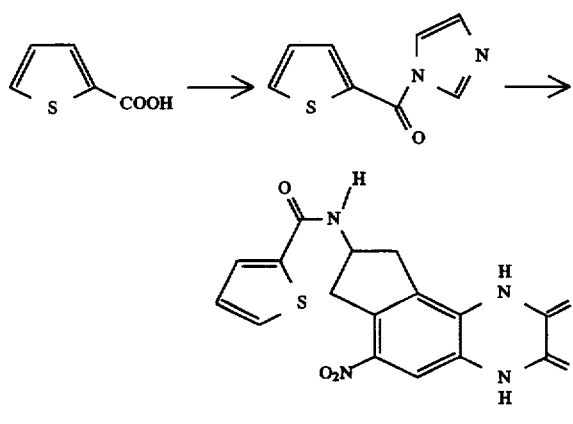

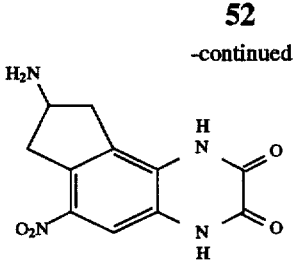

A solution of thiophene-2-carboxylic acid (1 mmol) in anhydrous tetrahydrofuran (THF) was treated with carbonyldiimidazole (1.2 mmol) and triethyl amine (1 mL) and heated at 60° C. for 30 min. After cooling to room temperature a solution of 8-amino-6-nitro-4,7,8,9,-tetrahydro-1H-cyclopenta[f]quinoxaline-2,3-dione (1 mmol) in dimethylformamide (DMF) was added. The reaction mixture as stirred at room temperature for 2 h, then heated at 70° C. for 2 h. The solvent was evaporated and the residue triturated with acetone. The solid was collected by filtration, washed with diethyl ether and dried in vacuo. Calc'd for $C_{16}H_{12}N_4O_5S \cdot H_2O$: C, 49.22; H, 3.61; N, 14.35, found: C, 49.06; H, 312; N, 15.05. MS M+1 (373).

EXAMPLE 55

Resolution of 2,5-diamino-6-bromo-4-nitroindane

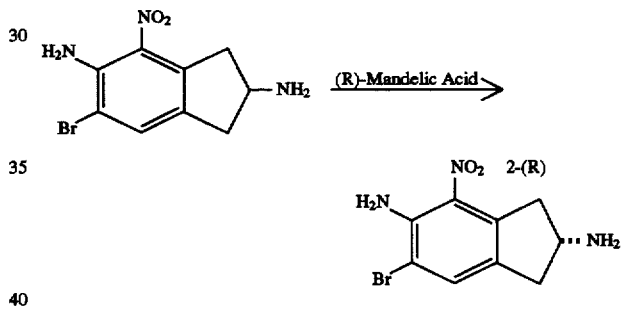

The amine (10.1 g) was dissolved in 185 mL of 4:1 isopropanol:water. (R)-Mandelic acid (2.8 g, 0.5 eq) was added and the mixture allowed to crystallize at room temperature for 18 h. The crystals were collected by filtration and dried. The solid was partitioned between methylene chloride: 1N NaOH, and the aqueous layer was back extracted. The combined organic layers were dried over sodium sulfate, and evaporated to give a solid (3.2 g). The recrystallization with (R)-mandelic acid was repeated a total of four times to give an enantiomeric excess of 99% of (R)-2,5-diamino-6-bromo-4-nitroindane as determined by chiral HPLC. Absolute configuration was determined by x-ray crystallography. The (R)- and (S)-enantiomers were carried individually through the remaining synthesis to give chiral quinoxalinedione adducts.

EXAMPLE 56

(S)-2,5-diamino-6-bromo-4-nitroindane

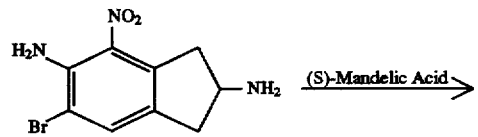

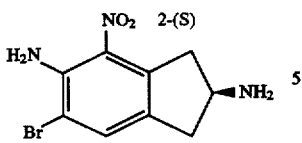

The title compound was obtained by an identical procedure to Example 55 except that the racemate was cocrystallized with (S)-mandelic acid.

EXAMPLE 57

(R)-Thiophene-2-carboxylic acid (6-nitro-2,3-dioxo-2,3,4,7,8,9-hexahydro-1H-cyclopenta[f]quinoxalin-8-yl)-amide

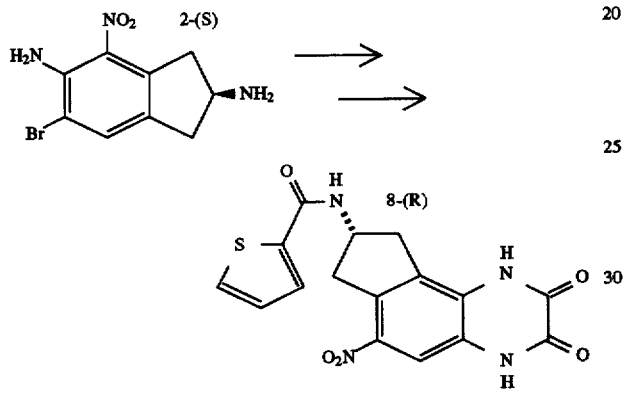

(S)-2,5-diamino-6-bromo-4-nitroindane was hydrogenated to the desbromotriamine and then condensed with oxalic acid (3N HCl at reflux) to give the 8-amino-4,7,8,9-tetrahydro-1H-cyclopenta[f]quinoxaline-2,3-dione. This intermediate was nitrated at C-6 in a solution of trifluoroacetic acid and fuming nitric acid at a temperature of 0° C. and then warmed to room temperature. The thienyl amide title compound was formed in an identical manner as described in example 54.

EXAMPLE 58

(S)-Thiophene-2-carboxylic acid (6-nitro-2,3-dioxo-2,3,4,7,8,9-hexahydro-1H-cyclopenta[f]quinoxalin-8-yl)-amide

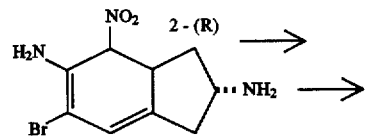

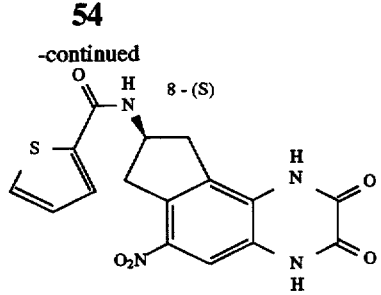

The title compound was prepared from (R)-2,5-diamino-6-bromo-4-nitroindane in a manner similar to that described in Example 57.

EXAMPLE 59

Furan-3-carboxylic acid (6-nitro-2,3-dioxo-2,3,4,7,8,9-hexahydro-1H-cyclopenta[f]quinoxalin-8-yl)-amide

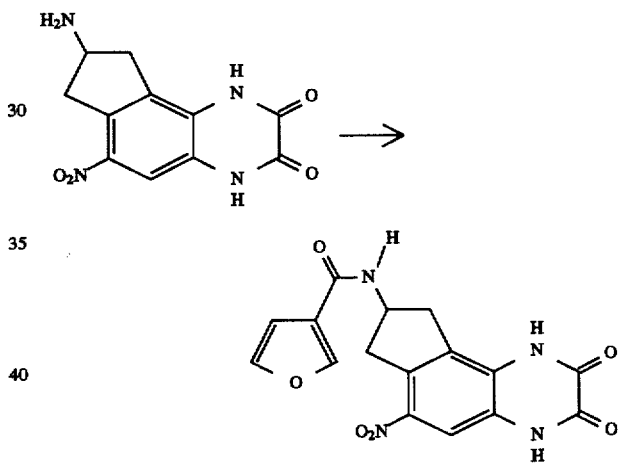

A solution of furan-3-carboxylic acid (1 mmol) in anhydrous THF was treated with carbonyldiimidazole (1.2 mmol) and triethyl amine (1 mL) and heated at 60° C. for 30 min. After cooling to room temperature a solution of 8-amino-6-nitro-4,7,8,9-tetrahydro-1H-cyclopenta[f]quinoxaline-2,3-dione (1 mmol) in DMF was added. The reaction mixture as stirred at room temperature for 2 h, then heated at 70° C. for 2 h. The solvent was evaporated and the residue triturated with acetone. The solid was collected by filtration, washed with diethyl ether and dried in vacuo. Calc'd for $C_{16}H_{12}N_4O_6 \cdot H_2O$: C, 51.34; H, 3.77; N, 14.97; found: C, 50.97; H, 3.18; N, 14.89. MS M+1 (357).

EXAMPLE 60

Thiophene-3-carboxylic acid (6-nitro-2,3-dioxo-2,3,4,7,8,9-hexahydro-1H-cyclopenta[f]quinoxalin-8-yl)amide

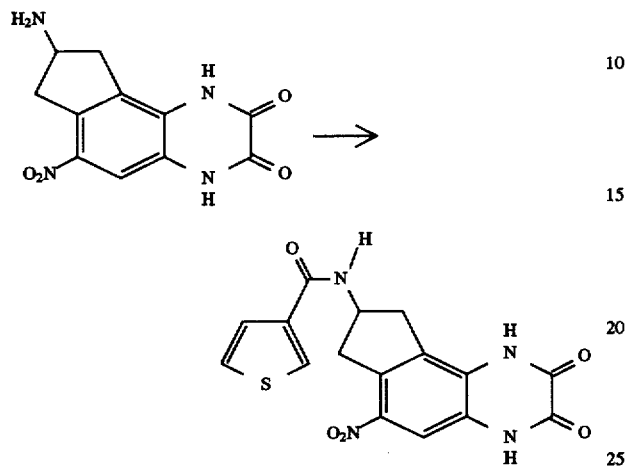

The title compound was prepared by a method identical to that used in example 54 except thiophene 3-carboxylic acid was used as a reactant. Calc'd for $C_{16}H_{12}N_4O_5S$: C, 51.61; H, 3.25; N, 15.05; found: C, 48.04; H, 3.45; N, 15.87. MS M+1 (373).

EXAMPLE 61

N-(6-Nitro-2,3-dioxo-2,3,4,7,8,9-hexahydro-1H-cyclopenta[f]quinoxalin-8-yl)-nicotinamide

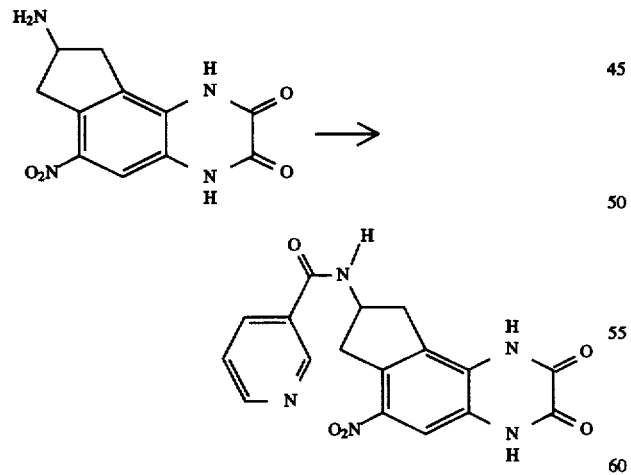

The title compound was prepared by a method identical to that used in example 54 except that nicotinic acid was used as a reactant. Calc'd for $C_{17}H_{13}N_5O_5$: C, 55.59; H, 3.57; N, 19.07; found: C, 50.27; H, 3.56; N, 18.70. MS M+1 (368).

EXAMPLE 62

Pyridine-2-carboxylic acid (6-nitro-2,3-dioxo-2,3,4,7,8,9-hexahydro-1H-cyclopenta[f]quinoxalin-8-yl)-amide

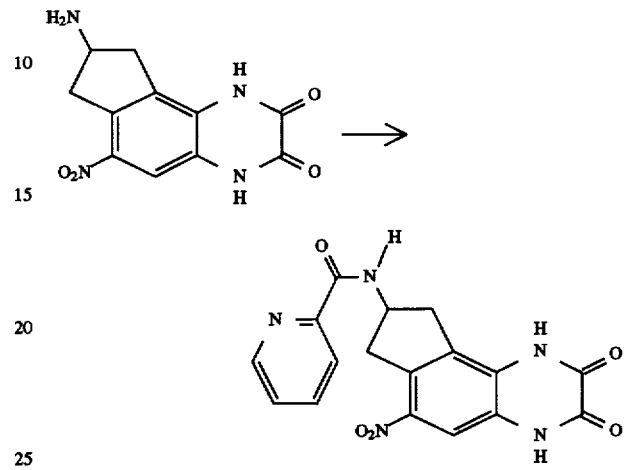

The title compound was prepared by a method identical to that used in example 54 except that pyridine-2-carboxylic acid was used as a reactant. Calc'd for $C_{17}H_{13}N_5O_5 \cdot H_2O$: C, 52.98; H, 3.92; N, 18.17; found: C, 52.70; H, 3.76; N, 18.29.

EXAMPLE 63

2,3,4,5-Tetrahydroxy-tetrahydro-furan-2-carboxylic acid (6-nitro-2,3-dioxo-2,3,4,7,8,9-hexahydro-1H-cyclopenta[f]quinoxalin-8-yl)-amide

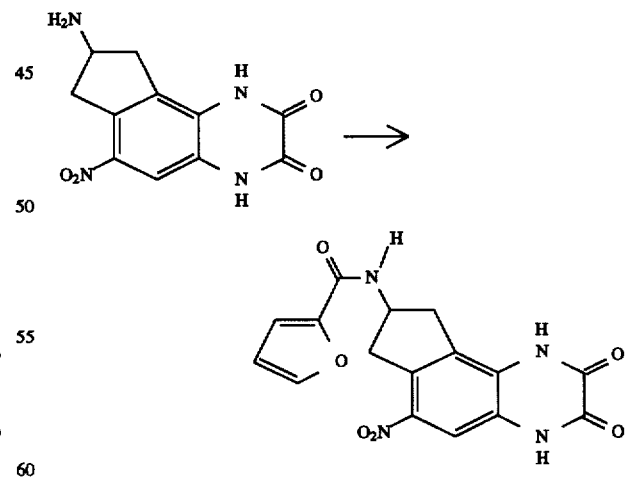

The title compound was prepared by a method identical to that used in example 54 except that furan-2-carboxylic acid was used as a reactant. Calc'd for $C_{16}H_{16}N_4O_{10} \cdot H_2O$: C, 40.19; H, 4.35; N 13.39; found: C, 40.11; H, 4.50; N, 13.41.

EXAMPLE 64

Pyrrolidine-2-carboxylic acid (6-nitro-2,3-dioxo-2,3,4,7,8,9-hexahydro-1H-cyclopenta[f]quinoxalin-8-yl)-amide

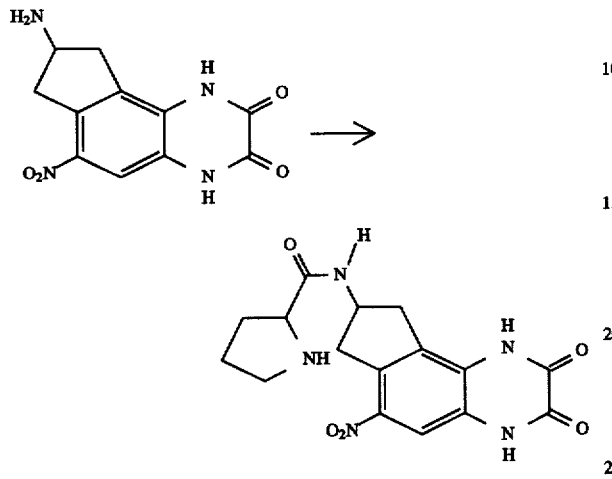

The title compound was prepared by a method identical to that used in example 54 except that pyrrolidine-2-carboxylic acid was used as a reactant. Calc'd for $C_{16}H_{17}N_5O_5 \cdot C_2HF_3O_2$: C, 45.67; H, 3.83; N, 14.79; found: C, 40.70; H, 3.66; N, 12.43.

EXAMPLE 65

Benzo[b]thiophene-2-carboxylic acid (6-nitro-2,3,-dioxo-2,3,4,7,8,9-hexahydro-1H-cyclopenta[f]quinoxalin-8-yl)-amide

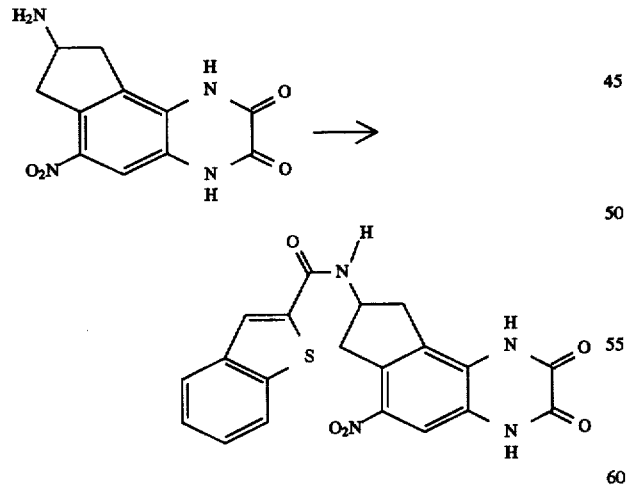

The title compound was prepared by a method identical to that used in example 54 except that benzo[b]thiophene-2-carboxylic acid was used as a reactant. Calc'd for $C_{20}H_{14}N_4O_5S$: C, 56.87; H, 3.34; N, 13.26; found: C, 50.99; H, 3.78; N, 14.38. MS M+1 (423).

EXAMPLE 66

2-(1H-Indol-3-yl)-N-(6-nitro-2,3-dioxo-2,3,4,7,8,9-hexahydro-1H-cyclopenta[f]quinoxalin-8-yl)-acetamide

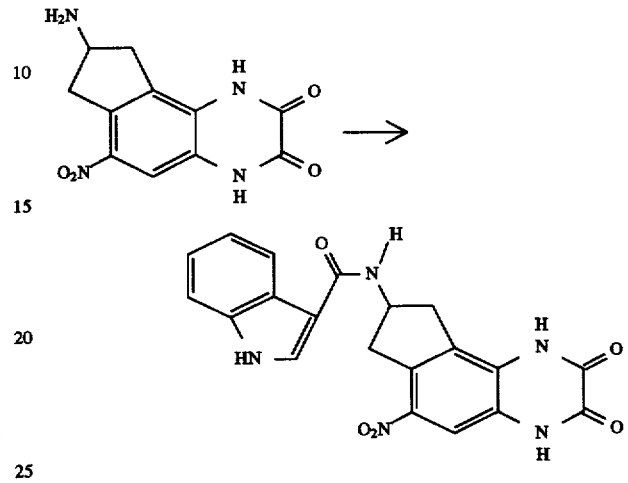

The title compound was prepared by a method identical to that used in example 54 except that 3-indolyl acetic acid was used as a reactant. Calc'd for $C_{12}H_{17}N_5O_5 \cdot H_2O$: C, 57.66; H, 4.38; N, 16.01; found: C, 57.56; H, 4.28; N, 15.67.

EXAMPLE 67

Thiophene-2-carboxylic acid methyl-(6-nitro-2,3-dioxo-2,3,4,7,8,9-hexahydro-1H-cyclopenta[f]quinoxalin-8-yl)-amide

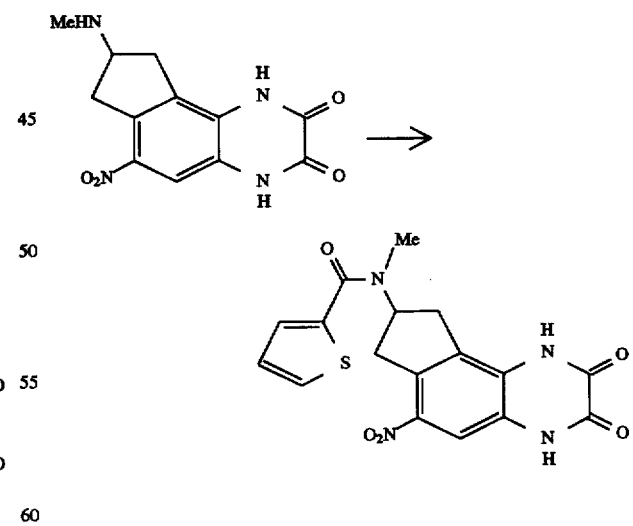

The title compound was prepared by a method identical to that used in example 54 except that 8-(N-methyl)amino-6-nitro-4,7,8,9-tetrahydro-1H-cyclopenta[f]quinoxaline-2,3-dione was used as a reactant. Calc'd for $C_{17}H_{14}N_4O_5S \cdot 0.75 H_2O$: C, 51.05; H, 3.91; N, 14.01; found: C, 50.81; H, 3.60; N, 13.48. MS M+1 (387).

EXAMPLE 68

N-Methyl-N-(6-nitro-2,3-dioxo-2,3,4,7,8,9-hexahydro-1H-cyclopenta[f]quinoxalin-8-yl)-benzamide

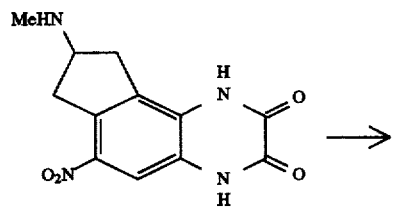

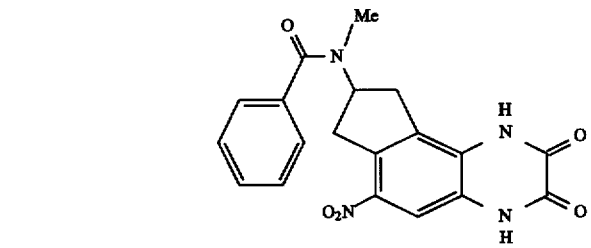

The title compound was prepared by a method identical to that used in example 67 except that benzoic acid was used as a reactant. Calc'd for $C_{19}H_{16}N_4O_5 \cdot 0.5\ H_2O$: c, 58.60; H, 4.40; N, 14.39; found: C, 58.62; H, 4.35; N, 13.26. MS M+1 (381).

EXAMPLE 69

6-Nitro-2,3-dioxo-2,3,4,7,8,9-hexahydro-1H-cyclopenta[f]quinoxaline-8-carboxylic acid methyl-phenyl-amide

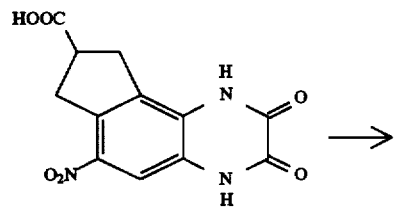

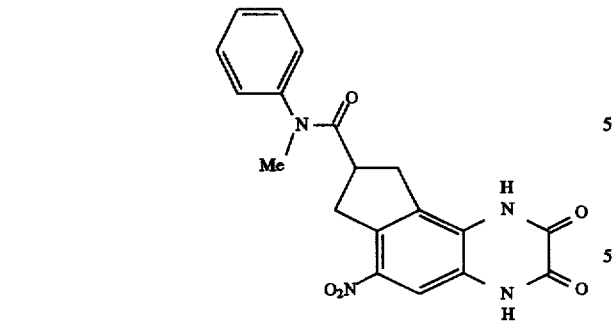

A solution of 6-nitro-2,3,-dioxo-2,3,4,7,8,9-hexahydro-1H-cyclopenta[f]quinoxaline-8-carboxylic acid (1 mmol, example 78) in anhydrous DMF was treated with carbonyldiimidazole (2 mmol) and triethylamine (1 mL) and then heated at 70° C. for 45 min. After cooling to room temperature methylphenylamine (1.2 mL) was added and the mixture stirred at 50° C. for 6 h. The solvent was removed in vacuo, and the residue triturated with acetone. The solid was collected by filtration, washed with diethyl ether and dried in vacuo. Calc'd for $C_{19}H_{16}N_4O_5 \cdot 1.2\ H_2O$: C, 56.77; H, 4.61; N, 13.93; found: C, 56.22; H, 4.13; N, 14.62. MS M+1 (381).

EXAMPLE 70

2-Carboxyethyl-1-indanone

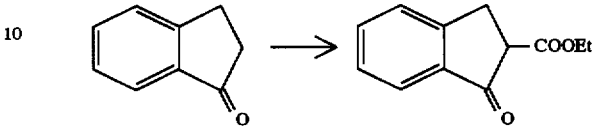

A mixture of 1-indanone (26.4 g, 0.2 mol), diethyl carbonate (35.4 g, 0.3 mol) and sodium hydride (16 g, 0.4 mol, 60% in oil) in THF (600 mL) was stirred at 40° C. for 2 h. The mixture was then poured onto 500 mL of 2N HCl and ice. The organic phase was separated, and the aqueous phase extracted with ether. The combined organic layers were washed with saturated NaCl, dried over Magnesium sulfate, filtered and evaporated to give the product as a syrup (38.3 gm).

EXAMPLE 71

2-Carboxyethylindane

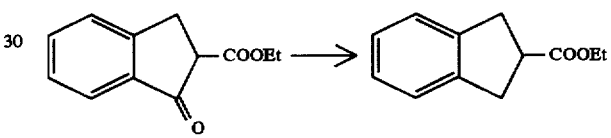

A mixture of 2-carboxyethyl-1-indanone (38.3 gm, 0.19 mol), 20% Pd/C (4 gm) and concentrated sulfuric acid (4 drops) in ethanol (400 mL) was shaken on a Parr hydrogenation apparatus under a hydrogen atmosphere (50.5 psi) for 15 h. After removal of the catalyst by filtration, the solvent was evaporated and the residue purified by silica gel chromatography (4:1 hexane:EtOAc) to give the product (28.8 gm).

EXAMPLE 72

2-Carboxyethyl -5-nitroindane

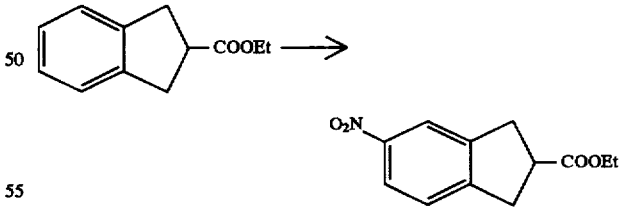

A mixture of 2-carboxyethylindane (28.8 g, 0.15 mol) and trifluoroacetic acid (300 mL) was cooled in an ice bath and then treated with fuming nitric acid (50 mL). The reaction mixture was slowly warmed to room temperature and allowed to stir for 18 h. After removing the solvent, the residue was dissolved in an either:water mixture. The ether layer was separated and washed with water, and then saturated NaCl, and dried over magnesium sulfate. The filtrate was evaporated to give a dark syrup (34.3 gm, 3:1 ratio of isomers).

EXAMPLE 73

5-Acetamido-2-carboxyethylindane

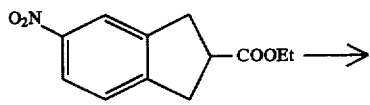

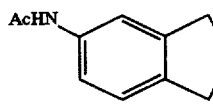

A mixture of 2-carboxyethyl-5-nitroindane (34 g, 0.15 mol), Raney nickel (5 g), acetic anhydride (25 mL) and acetic acid (225 mL) was shaken on a Parr hydrogenation apparatus under a hydrogen atmosphere (50 psi) for 30 h. After removing the catalyst, the filtrate was evaporated to give a dark syrup. The residue was purified by column chromatography (3:2 hexane:EtOAc).

EXAMPLE 74

5-Acetamido-6-bromo-2-carboxyethylindane

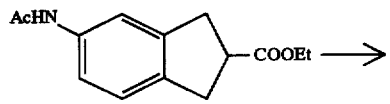

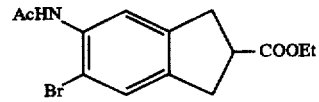

A solution of 5-acetamido-2-carboxyethylindane (18 g, 73 mmol), sodium acetate (9 g, 110 mmol) in acetic acid (300 mL) was treated dropwise with bromine (14.1 g, 88 mmol) and then stirred for 18 h. After removing the solvent, the residue was dissolved in an ether:water mixture, and sodium bisulfite was added. The ether layer was separated and the aqueous layer back extracted. The combined organic layers were washed with saturated NaCl, dried over magnesium sulfate, filtered and evaporated. The syrup was purified by silica gel chromatography (3:2 hexane:EtOAc) to give the product.

EXAMPLE 75

5-Acetamido-6-bromo-2-carboxyethyl-4-nitroindane

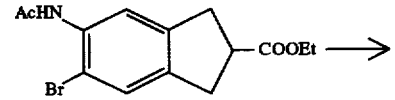

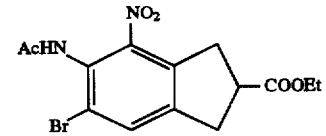

A mixture of 5-acetamido-6-bromo-2-carboxyethylindane (7 g, 20 mmol) and trifluoroacetic acid (150 mL) was cooled in an ice bath and treated with fuming nitric acid (10 mL). After 2 h at 0° C., the solvent was removed and the residue solidified upon addition of water. The solid was collected by filtration, washed with ether and dried. Crystallization from hot toluene gave the pure product (7 g).

EXAMPLE 76

5-Amino-6-bromo-4-nitroindane-2-carboxylic acid

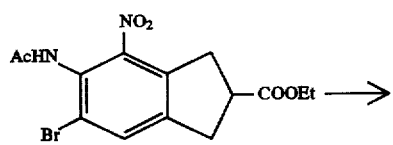

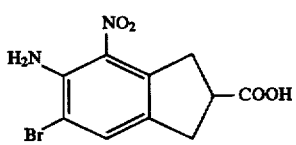

A mixture of 5-acetamido-6-bromo-2-carboxyethyl-4-nitroindane (7.1 g, 19 mmol) in acetic acid (25 mL) and 3N HCl (100 mL) was heated at 100° C. for 18 h. The mixture was concentrated by rotoevaporation, and the resulting orange solid was collected by filtration, washed with ether and dried to give the product (5.5 g).

EXAMPLE 77

2,3-Dioxo-2,3,4,7,8,9-hexahydro-1H-cyclopenta[f]quinoxaline-8-carboxylic acid

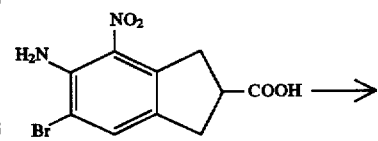

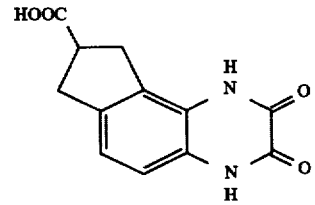

A mixture of 5-amino-6-bromo-4-nitroindane-2-carboxylic acid (5.5 g, 18 mmol) and 20% Pd/C (0.5 g) in 95% ethanol (250 mL) and tetrahydrofuran (250 mL) was shaken on a Parr hydrogenation apparatus under a hydrogen atmosphere (51 psi) for 30 h. After removing the catalyst, the solvent was evaporated to give a solid. The solid was dissolved in 2N HCl (150 mL) and treated with oxalic acid (4.6 g), and then the mixture was heated at 90° C. for 5 h. After cooling to room temperature, the precipitate was collected by filtration and dried in vacuo (4.0 g).

EXAMPLE 78

6-Nitro-2,3,-dioxo-2,3,4,7,8,9-hexahydro-1H-cyclopenta[f]quinoxaline-8-carboxylic acid

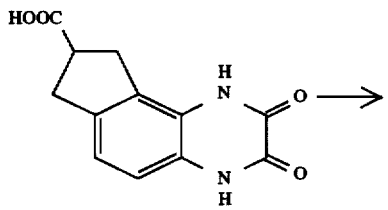

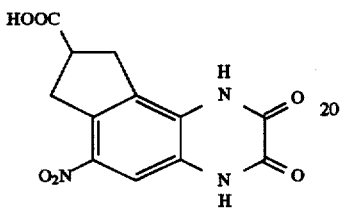

A mixture of 2,3-dioxo-2,3,4,7,8,9-hexahydro-1H-cyclopenta[f]quinoxaline-8-carboxylic acid (4 g, 16 mmol) in trifluoroacetic acid (75 mL) was cooled to 0° C. and then treated with fuming nitric acid (5 mL). After stirring in an ice bath for 3 h, the mixture was warmed to room temperature for 1 h, the solvent evaporated, and the residue was suspended in water. A solid precipitate was collected by filtration, washed with ether and dried in vacuo (4 g). Calc'd for $C_{12}H_9N_3O_6 \cdot 0.5\ H_2O$: C, 48.00; H, 3.36; N, 14.00; found: C, 48.64; H, 3.13; N, 13.86. MS M+1 (292).

EXAMPLE 79

General Procedure for Amide Preparation

A mixture of 6-nitro-2,3-dioxo-2,3,4,7,8,9-hexahydro-1H-cyclopenta[f]quinoxaline-8-carboxylic acid (0.29 g, 1 mmol), the coupling reagent N-(3-dimethylaminopropyl)-N'-ethylcarbodiimide hydrochloride (EDAC) (0.29 g, 1.5 mmol), and the 'generic amine' (1.5 mmol) in dimethylformamide (15 mL) was treated with dimethylaminopyridine (10 mg) and heated and 50° C. for 18 h. The solvent was evaporated, the residue taken up in water treated as necessary to cause precipitation of the product. The product was purified using standard methodologies. For example, aniline was couple by a similar method with 6-nitro-2,3-dioxo-2,3,4,7,8,9-hexahydro-1H-cyclopenta[f]quinoxaline-8-carboxylic acid to give the carboxylic acid phenylamide, example 57, and N-methylaniline was coupled to give example 55. Other couple reagents including carbonyldiimidazol (CDI), dicyclohexylcarbyldiimide (DCC), etc. can be substituted for EDAC.

EXAMPLE 80

6-Nitro-2,3,-dioxo-2,3,4,7,8,9-hexahydro-1H-cyclopenta[f]quinoxaline-8-carboxylic acid phenylamide

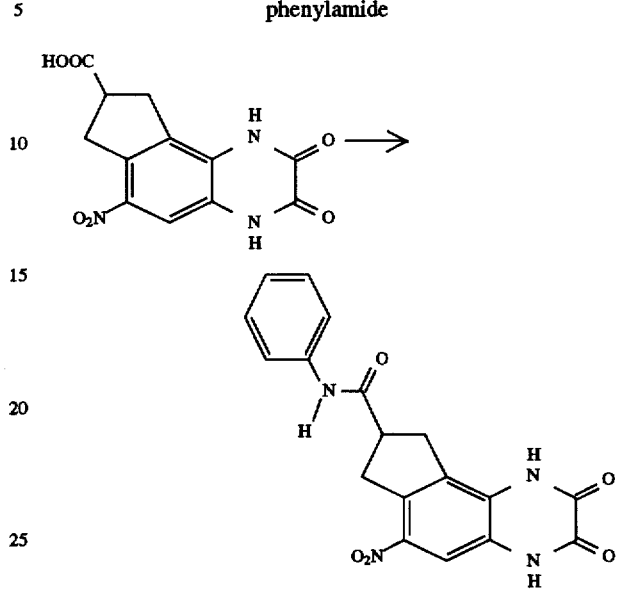

The title compound was prepared by a method identical to that used in example 69 except that aniline was used as a reactant. Calc'd for $C_{18}H_{14}N_4O_5 \cdot H_2O$: C, 56.24; H, 4.20; N, 14.58; found: C, 56.10; H, 4.04; N, 14.57. MS M+1 (367)

EXAMPLE 81

1-Acetamido-7-pyrrolidin-1-yl-5,6,7,8-tetrahydronaphthalene

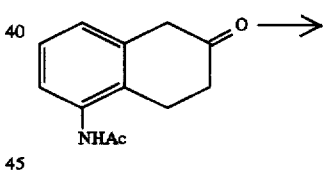

A mixture of 8-acetamido-2-tetralone (0.4 g, 2 mmol), pyrrolidine (0.28 g, 4 mmol) and tosic acid (10 mg) in benzene:DMF (5:1, 12 mL) was heated at reflux with a Dean-Stark trap for 4 h. The solvent was evaporated and the residue dissolved in 1:1 MeOH:THF (10 mL). Acetic acid (1 mL) and sodium cyanoborohydride (0.25 g, 4 mmol) were added, and the reaction stirred for 16 h. The solvent was evaporated and the residue taken up in water:methylene chloride. The aqueous layer was basified with 12.5% NaOH, and back extracted. The combined organic phase was dried over sodium sulfate, filtered and evaporated. The residue solidified upon standing, and was crystallized from tolune-:hexane to give the product (0.36 g).

EXAMPLE 82

1-Acetamido-4-bromo-7-pyrrolidin-1yl-5,6,7,8-tetrahydronaphthalene

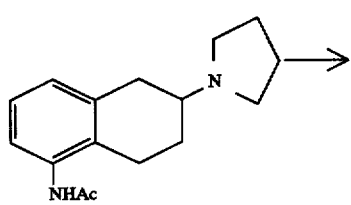

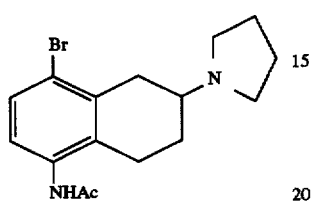

A solution of 1-acetamido-7-pyrrolidin-1-yl-5,6,7,8-tetrahydronaphthalene (0.36 g, 1.4 mmol) and sodium acetate trihydrate (0.38 g, 2.8 mmol) in acetic acid (15 mL) was treated with bromine (0.27 g, 1.7 mmol) and stirred at room temperature for 2 h. A precipitate was collected by filtration and the filtrate evaporated. The two solids were combined and dissolved in methylene chloride; water. The mixture was basified with 12.5% NaOH, and the organic phase separated. The aqueous layer was back extracted and the combined organic layers were dried over sodium sulfate, filtered and evaporated. The residue was heated in diethyl ether to form a solid, which was collected and dried (0.31 g).

EXAMPLE 83

1-Acetamido-4-bromo-2-nitro-7-pyrrolidin-1-yl-5,6,7,8-tetrahydronaphthalene

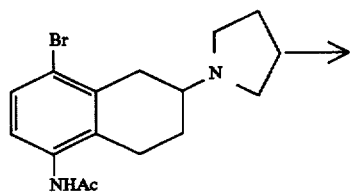

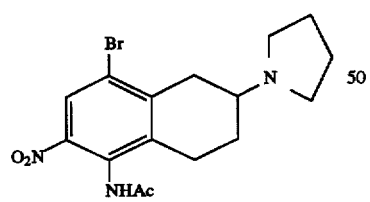

A mixture of 1-acetamido-4-bromo-7-pyrrolidin-1-yl-5,6,7,8-tetrahydronaphthalene (0.3 g) in trifluoroacetic acid (10 mL) was cooled in an icebath and treated with fuming nitric acid (0.5 mL). After stirring for 4 h, the solvent was evaporated and the residue taken up in methylene chloride-:water. The mixture was basified with 12.5% NaOH, and the aqueous layer back extracted. The combined organic layers were dried over sodium sulfate, filtered and evaporated to give a solid. Preparative thin layer chromatography (7:3 EtOAc:MeOH) was used to obtain the purified product (0.12 g).

EXAMPLE 84

1-Amino-4-bromo-2-nitro-7-pyrrolidin-1-yl-5,6,7,8-tetrahydronaphthalene hydrochloride

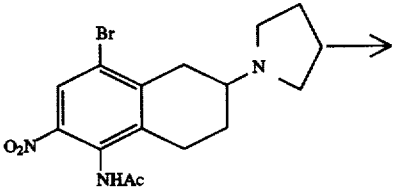

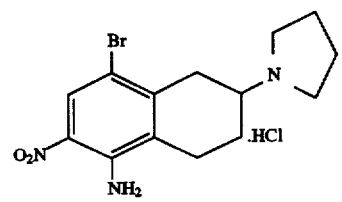

The acetamide (0.12 g) was hydrolyzed at 100° C. in 2N HCl while stirring for 18 h. The solvent was removed to give a yellow solid (0.1 g).

EXAMPLE 85

9-pyrrolidin-1-yl-1,4,7,8,9,10-hexahydrobenzo[f]quinoxaline-2,3,-dione hydrochloride

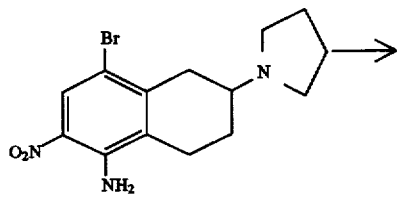

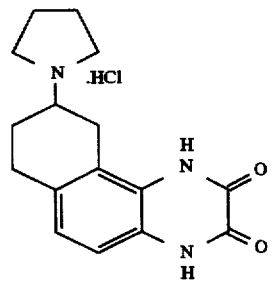

A mixture of 1-amino-4-bromo-2-nitro-7-pyrrolidin-1-yl-5,6,7,8-tetrahydronaphthalene hydrochloride (0.1 g, 0.27 mmol) and 20% Pd/C (0.03 g) in methanol (75 mL) was shaken on a Parr hydrogenation apparatus under a hydrogen atmosphere (51 psi) for 3 h. The solvent was evaporated and the residue dissolved in 2N HCl (5 mL). Oxalic acid (0.12 g) was added and the mixture heated at 100° C. for 3 h. After cooling to room temperature, the precipitate was collected by filtration and dried (0.04 g).

EXAMPLE 86

6-Nitro-9-pyrrolidin-1-yl-1,4,7,8,9,10-hexahydrobenzo[f]quinoxaline-2,3-dione

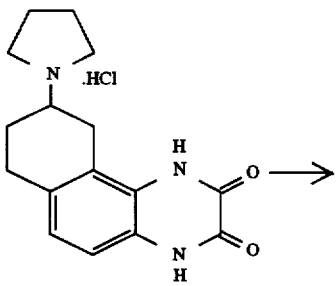

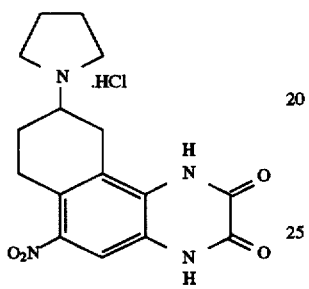

A mixture of 9-pyrrolidin-1-yl-1,4,7,8,9,10-hexahydrobenzo[f]quinoxaline-2,3-dione hydrochloride (35 mg) in trifluoroacetic acid (2 mL) was cooled in an ice bath and treated with 0.5 mL fuming nitric acid. After 2 h at room temperature, the solvent was evaporated and the residue suspended in acetone:water, and the resulting solid collected by filtration (35 mg). Calc'd for $C_{16}H_{18}N_4O_4 \cdot HCl$: C, 52.39; H, 5.22; H, 15.27; found: C, 42.95; H, 4.69; N, 16.28. MS M+1 (331).

EXAMPLE 87

2,5-Di-($N^2$-dimethyl)amino-6-bromo-4-nitroindane

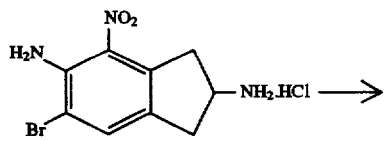

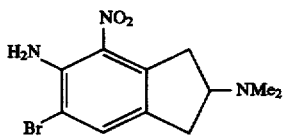

A mixture of 2,5-diamino-6-bromo-4-nitroindane hydrochloride (1.5 g, 5 mmol), paraformaldehyde (0.9 g, mmol), sodium cyanoborohydride (0.63 g, 10 mmol) and sodium acetate (1.3 g, 10 mmol) in acetic acid was stirred at room temperature for 72 h, then heated at 50° C. for 6 h. The solvent was evaporated and the residue dissolved in water-:methylene chloride. The aqueous layer was basified with 12.5% NaOH and back extracted. The combined organic layers were dried over sodium sulfate, filtered and evaporated to give a yellow solid. Silica gel chromatography (30% methanol in EtOAc) gave the product as an orange solid (0.5 g).

EXAMPLE 88

2,5-Di-($N^2$-diethyl)amino-6-bromo-4-nitroindane

The title compound was prepared from 2,5-diamino-6-bromo-4-nitroindane hydrochloride (1.4 g, 5 mmol) and acetaldehyde (4.3 g, 0.1 mol) in acetic acid (50 mL) by reducing with sodium cyanoborohydride (1.3 g) in a manner similar to Example 88. The product (0.46 g) was purified by silica gel chromatography (5% methanol in EtOAc).

EXAMPLE 89

8-Dimethylamino-4,7,8,9-tetrahydro-1H-cyclopenta[f]quinoxaline-2,3-dione hydrochloride

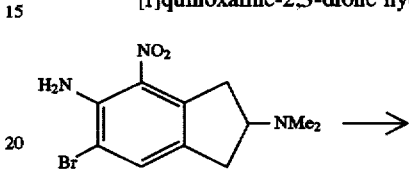

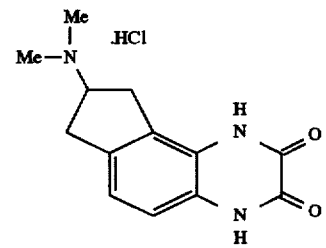

A solution of 2,5-di-($N^2$-dimethyl)amino-6-bromo-4-nitroindane (0.5 g, 1.7 mmol) and 20% Pd/C (0.1 g) in methanol (75 mL) was shaken on a Parr hydrogenation apparatus under a hydrogen atmosphere (52 psi) for 14.5 h. After removing the catalyst, the solvent was evaporated to give a white solid. The solid was dissolved in 2N HCl (25 mL) and then treated with oxalic acid (0.5 g, 4 mmol) and heated at 100° C. for 3 h. After cooling, the solution was basified, to pH 9 with 2N NaOH. The resulting precipitate was collected by filtration and dried (0.4 g).

EXAMPLE 90

8-Dimethylamino-6-nitro-4,7,8,9-tetrahydro-1H-cyclopenta[f]quinoxaline-2,3-dione

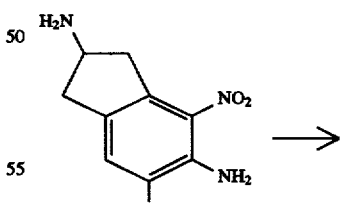

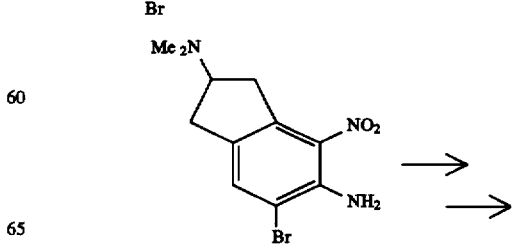

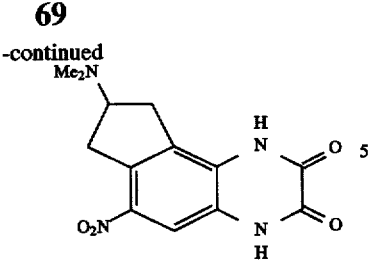

A mixture of 2,5-diamino-6-bromo-4-nitroindane (1 mmol) and paraformaldehyde (4 mmol) in acetic acid (100 mL) was treated portionwise with sodium cyanoborohydride (2 mmol), and then heated at 50° C. for 4 h. The dimethylamino derivative was purified by column chromatography and converted by sequential hydrogenation and condensation with oxalic acid to the quinoxalinedione. Nitration at C-6 was accomplished with fuming nitric acid in trifluoroacetic acid at 0° C. and then warming to room temperature. After stripping the solvent, the product was triturated with acetone, collected by filtration and washed with diethyl ether and dried in vacuo. Calc'd for $C_{13}H_{14}N_4O_4 \cdot HCl$: C, 47.79; H, 4.63; N, 17.15; found: C, 43.09; H, 4.08; N, 19.03. Ms M+1 (291).

EXAMPLE 91

8-Diethylamino-4-7,8,9-tetrahydro-1H-cyclopenta[f]quinoxaline-2,3-dione hydrochloride The title product was prepared in an identical manner to Example 89 using 2,5-di-($N^2$-diethyl)amino-6-bromo-4-nitroindane (0.46 g, 1.4 mmol) as a starting material.

EXAMPLE 92

2-Ethylcarbamoylindane

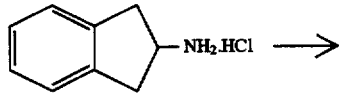

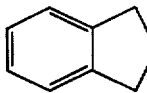

A mixture of 2-aminoindane hydrochloride (25 g, 0.15 mol) and ethyl chloroformate (21.7 g, 0.2 mol) in saturated sodium bicarbonate (200 mL) and ether (200 mL) was stirred at room temperature for 1 h. The ether layer was separated and the aqueous layer back extracted. The combined ether extracts were washed with saturated NaCl, dried over magnesium sulfate, filtered and evaporated to give a white solid (27 g).

EXAMPLE 93

2-(N-Methyl)acetamidoindane

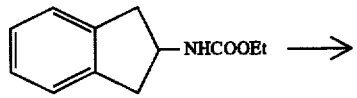

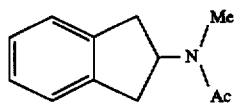

A solution of 2-ethylcarbamoylindane (20.5 g, 0.1 mol) in diethyl ether (250 mL) was cooled in an ice bath and then treated portionwise with lithium aluminum hydride (7.6 g, 0.2 mol). The reaction mixture was stirred over 16 h while warming to room temperature. The reduction was incomplete, and was then heated at reflux for an additional 24 h. The mixture was cooled to 0° C. and treated cautiously with water (8 mL), followed by 12.5% NaOH (6.5 mL) and water (16 mL). The white precipitate was removed by filtration and washed with ether and THF. The filtrate was treated with acetic anhydride (13 g) and the filtrate evaporated to a syrup. Silica gel chromatography (1:1 hexane:EtOAc) gave the product (12.2 g).

EXAMPLE 94

2-(N-Methyl)acetamido-5-nitroindane

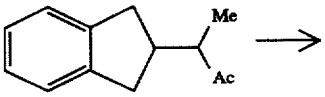

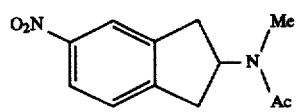

A mixture of 2-(N-methyl)acetamidoindane (16 g, 85 mmol) in trifluoroacetic acid (200 mL) was cooled in an ice bath and then treated with fuming nitric acid (20 mL). After stirring for 1 h in the ice bath, the reaction was stirred for an additional 3 h at room temperature. The solvent was removed and the residue taken up in methylene chloride-:water. The aqueous phase was extracted with methylene chloride and the combined organic layers were dried over magnesium sulfate, filtered and evaporated to give the product (20 g).

EXAMPLE 95

$N^2$-Methyl-2,5-diacetamidoindane

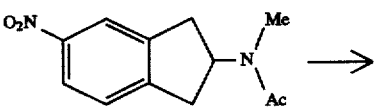

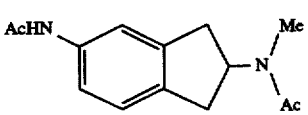

A mixture of 2-(N-methyl)acetamido-5-nitroindane (20.1 g, 85 mmol) and Raney nickel (10 g) in THF (100 mL) and methanol (100 mL) was stirred under a hydrogen atmosphere (balloon) at room temperature for 18 h. The catalyst was removed, and the filtrate was treated with acetic anhydride (18 g), and then evaporated to a brown syrup (22 g).

EXAMPLE 96

N²-Methyl-2,6-diacetamido-5-bromoindane

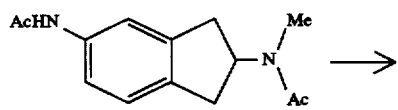

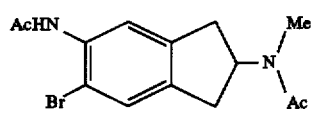

A mixture of N²-methyl-2,5-diacetamidoindane (22 g, 85 mmol) and sodium acetate trihydrate (23 g, 0.17 mmol) in acetic acid (250 mL) was treated dropwise with bromine (17 g, 0.11 mol) and stirred for 18 h at room temperature. The mixture was treated with sodium bisulfite and evaporated. The residue was taken up in methylene chloride:water, and the aqueous layer was back extracted with additional methylene chloride. The combined organic layers were dried over sodium sulfate, filtered and evaporated to give a syrup (26 g). The syrup was triturated with diethyl ether to give the product as a white solid.

EXAMPLE 97

N²-Methyl-2,5-diacetamido-6-bromo-4-nitroindane

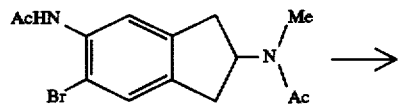

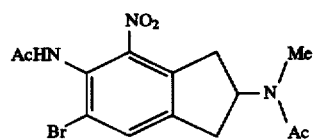

A mixture of N²-methyl-2,6-diacetamido-5-bromoindane (21.8 g, 67 mmol) in trifluoroacetic acid (200 mL) was cooled in an ice bath and treated with fuming nitric acid (25 mL). After stirring for 1 h, the mixture was warmed to room temperature and stirred for an additional 3 h. The solvent was removed and the residue taken up in water. The mixture was triturated in diethyl ether to give a precipitate, which was collected by filtration and dried to give the product (22.5 g).

EXAMPLE 98

N²-Methyl-2,5-diamino-6-bromo-4-nitroindane hydrochloride

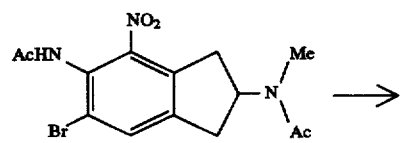

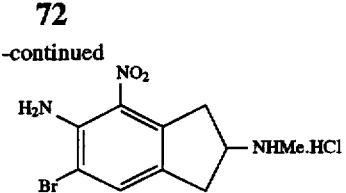

A mixture of N²-methyl-2,5-diacetamido-6-bromo-4-nitroindane (22.5 g, 61 mmol) in 3N HCl (150 mL) and acetic acid (50 mL) was heated at 100° C. for 24 h. The mixture was cooled in an ice bath and the orange precipitate was collected by filtration and dried (17.2 g).

EXAMPLE 99

8-Methylamino-4,7,8,9-tetrahydro-1H-cyclopenta[f]quinoxaline-2,3-dione

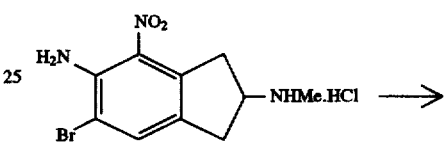

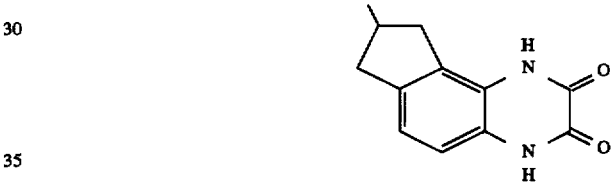

A mixture of N²-methyl-2,5-diamino-6-bromo-4-nitroindane hydrochloride (17.2 g, 53 mmol) and 20% Pd/C (1 g) in methanol (250 mL) was shaken on a Parr hydrogenation apparatus under a hydrogen atmosphere (50 psi) for 6 h. After removing the catalyst, the filtrate was evaporated and the residue taken up in 2N HCl 250 mL) and oxalic acid (13 g, 0.1 mmol) and heated at 100° C. for 5 h. The mixture was cooled in a refrigerator overnight, and the resulting precipitate was collected by filtration and washed with water and then diethyl ether and dried to give the product (9.9 g).

EXAMPLE 100

8-Methylamino-6-nitro-4,7,8,9-tetrahydro-1H-cyclopenta[f]quinoxaline-2,3-dione methane sulfonate salt

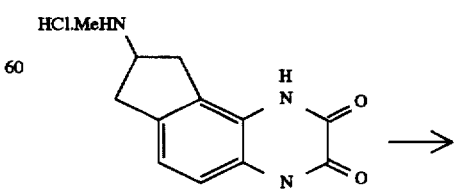

-continued

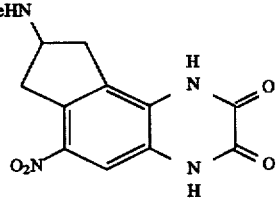

A mixture of 8-methylamino-4-7,8,9-tetrahydro-1H-cyclopenta[f]quinoxaline-2,3-dione (9.9 g) in trifluoroacetic acid was cooled in an ice bath and treated with fuming nitric acid (10 mL). After stirring at 0° C. for 1 h, the reaction mixture was warmed to room temperature for an additional 1 h. The solvent was removed, and the residue taken up in acetone:water. The yellow solid was collected by filtration, washed with water and dried (9.8 g). One gram was taken up in water and NaOH (1 eq) and stirred at room temperature for 3 h. The solid was collected by filtration and dried. The solid was suspended in methanol and treated with methanesulfonic acid and stirred for 15 min. A tan solid was collected by filtration and dried.

8-Methylamino-6-nitro-4,7,8,9-tetrahydro-1H-cyclopenta[f]quinoxaline-2,3-dione. A mixture of 8-dimethylamino-4,7,8,9-tetrahydro-1H-cyclopenta[f]quinoxaline-2,3-dione hydrochloride (0.39 g) in trifluoroacetic acid was cooled in an ice bath and then treated with fuming nitric acid (1 mL). After stirring for 1 h, the mixture was warmed to room temperature for 3 h. The solvent was evaporated and the residue suspended in methanol. The resulting yellow solid was collected by filtration and dried. Calc'd for $C_{12}H_{12}N_4O_4 \cdot CH_4O_3S$: C, 41.93; H, 4.33; N, 15.05; found: C, 39.56; H, 4.11; N, 13,61. Ms M+1 (277).

EXAMPLE 101

2-[Bis-(2-hydroxy-ethyl)-amino]-N-(6-nitro-2,3-dioxo-2,3,4,7,8,9-hexahydro-1H-cyclopenta[f]quinoxalin-8-yl)-acetamide A mixture of 2-[bis-(2-hydroxy)ethylglycine (1.6 g, 10 mmol), t-butyldimethylsilylchloride (6 g, 40 mmol) and imidazole (3.4 g, 50 mmol) in DMF (30 mL) was stirred at room temperature for 18 h. The solvent was evaporated and the residue dissolved in 1N HCl:methylene chloride. The layers were separated, and the aqueous layer back extracted. The combined organic layers were dried over sodium sulfate, filtered and evaporated to give a solid. The resulting silylated derivative was suspended in hexane, collected by filtration and dried.

A solution of bis(2-t-butyldimethylsilyloxy) ethylglycine (0.38 g, 1 mmol) and carbonyldiimidazole (0.16 g, 1 mmol) in THF (5 mL) was heated at reflux for 30 min. The mixture was then added to a solution of 8-amino-6-nitro-4,7,8,9-tetrahydro-1H-cyclopenta[f]quinoxaline-2,3-dione hydrochloride (0.15 g, 0.5 mmol) in DMF (20 mL) and stirred at 70° C. After 30 min, triethylamine (0.2 g, 4 eq) was added and the reaction mixture was heated for 18 h. Another equivalent of the adduct of the starting glycine adduct and CDI was prepared as before, and added to the mixture. After heating at 70° C. for 18 h longer, the mixture was filtered and the filtrate was evaporated. The residue was warmed in ethanol to give a solid, which was collected and dried. Calc'd for $C_{17}H_{21}N_5O_7 \cdot HCl \cdot 0.4 H_2O$: C, 45.08; H, 5.12; N, 15.47; found: C, 44.71; H, 4.70; N, 15.65.

EXAMPLE 102

5-Amino-6-bromo-4-nitro-2-pyrrolidin-1-yl-indane

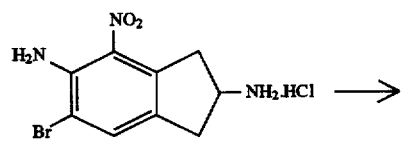

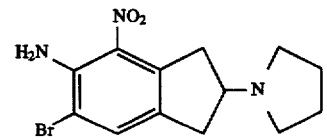

A mixture of 2,5-diamino-6-bromo-4-nitroindane hydrochloride (1.5 g, 5 mmol), 1-4-dibromobutane (1.3 g, 6 mmol) and diisopropylethylamine (1.9 g, 15 mmol) in DMF (100 mL) was heated at 70° C. for 24 h. The solvent was evaporated and the residue taken up in methylene chloride:water. The aqueous layer was basified with 1N NaOH and back extracted. The combined organic layers were dried over sodium sulfate, filtered and evaporated to give a dark syrup. The purified product (0.5 g) was obtained from column chromatography (4:1 EtOAc:methanol).

EXAMPLE 103

8-Pyrrolidin-1-yl-4,7,8,9-tetrahydro-1H-cyclopenta[f]quinoxaline-2,3-dione

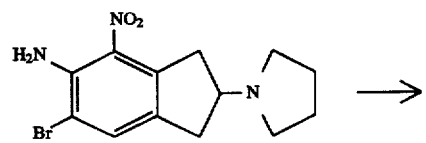

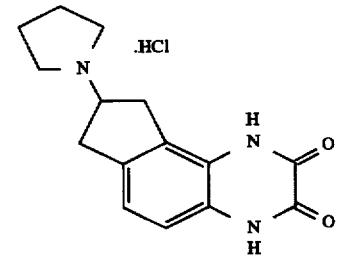

The title product was obtained by an analogous procedure to that described in Example 100 employing hydrogenation followed by condensation with oxalic acid to give the product (0.15 g).

EXAMPLE 104

6-Nitro-8-pyrrolidin-1-yl-4,7,8,9-tetrahydro-1H-cyclopenta[f]quinoxaline-2,3-dione Nitration of 8-pyrrolidin-1-yl-4,7,8,9-tetrahydro-1H-cyclopenta[f]quinoxaline-2,3-dione as described before with fuming nitric acid in trifluoroacetic acid gave the product as a yellow solid (0.1 g). $C_{15}H_{16}N_4O_4 \cdot HCL$. MS M+1 (317). HPLC 99%.

EXAMPLE 105

N-Methyl-N-(6-nitro-2,3,-dioxo-2,3,4,7,8,9-hexahydro-1H-cyclopenta[f]quinoxaline-8-yl)acetamide A mixture of 8-methylamino-6-nitro-4,7,8,9-tetrahydro-1H-cyclopenta[f]quinoxaline-2,3-dione (0.5 g, 1.6 mmol), acetic anhydride (0.5 g, 5 mmol), triethylamine (0.5 g, 5 mmol) in water (5 mL) was stirred for 15 min at room temperature. The solid was collected by filtration, washed with 2N HCl, then washed with diethyl ether and dried (0.5 g). Calc'd for $C_{14}H_{14}N_4O_5$: C, 52.83; H, 4.43; N, 17.60; found: C, 48.62; H, 4.26; N, 15.50.

EXAMPLE 106

5-Amino-6-bromo-4-nitro-2-piperidin-1-yl-indane

A mixture of 2,5-diamino-6-bromo-4-nitroindane hydrochloride (1.5 g, 5 mmol), 1,5-dibromopentane (1.4 g, 6 mmol) and diisopropylethylamine (1.3 g, 10 mmol) in DMF (100 mL) was heated at 50° C. for 24 h. The solvent was evaporated and the residue taken up in methylene chloride-:water. The aqueous layer was basified with 2N NaOH and back extracted. The combined organic layers were dried over sodium sulfate, filtered and evaporated to give a syrup. The purified product (0.8 g) was obtained from column chromatography (4:1 EtOAc:methanol).

EXAMPLE 107

8-Piperidin-1-yl-4,7,8,9-tetrahydro-1H-cyclopenta[f]quinoxaline-2,3,-dione hydrochloride The product (0.35 g) was obtained using a standard hydrogenation of 5-amino-6-bromo-4-nitro-2-piperidin-1-yl-indane (0.8 g, 2.6 mmol) over 20% Pd/C and condensation with oxalic acid.

EXAMPLE 108

6-Nitro-8-piperidin-1-yl-4,7,8,9-tetrahydro-1H-cyclopenta[f]quinoxaline-2,3-dione A yellow solid was obtained by an identical procedure as used for example 61. Calc'd for $C_{16}H_{18}N_4O_4HCl$: C, 52.39; H, 5.22; H, 15.27; found: C, 39.21; H, 4.60; N, 15.65 Ms M+1 (331).

EXAMPLE 109

8-Diethylamino-6-nitro-4,7,8,9,-tetrahydro-1H-cyclopenta[f]quinoxaline-2,3-dione Prepared by an identical procedure as used for example 61. Calc'd for $C_{15}H_{18}N_4O_4.HCL$; C, 42.39; H, 4.56; N, 16.29; found: C, 50.78; H, 5.40; N, 15.79. MS M+1 (319).

Other variations and modifications of this invention will be obvious to those skilled in the art.

What is claimed is:

1. A compound represented by the formula:

or a pharmaceutically acceptable salt thereof, wherein

Z is an alicyclic fused ring having 5 to 7 carbon atoms;
$R^1$ is hydrogen, an alkyl or an arylalkyl;
X and Y are independently hydrogen, halogen, nitro, cyano, COOH, $CONR^2R^3$, $SONR^2R^3$ wherein $R^2$ and $R^3$ are independently hydrogen, alkyl having 1 to 6 carbon atoms, cycloalkyl or aralkyl; and A is O, $CH_2$, $NR^4$, $CH_2NR^4$, CN, tetrazole or CO wherein $R^4$ is hydrogen, alkyl, hydroxyalkyl, aminoalkyl or aralkyl, wherein (i) when A is O, $CH_2$, $NR^4$ or $CH_2NR^4$ then B is hydrogen, alkyl, alkenyl, alkynyl, aryl, aralkyl, hydroxyalkyl, alkoxy, aminoalkyl, heterocyclic, alkylheterocyclic, heterocyclic-methyl, heterocyclic-ethyl, alkylcarbonyl, cycloalkylcarbonyl, arylcarbonyl, aralkylcarbonyl, heterocyclic-carbonyl, or alkylheterocyclic-carbonyl, any of which may be unsubstituted or substituted by one or more hydroxy, $CO_2H$, mercapto, amino, alkyl, bis-(hydroxyalkyl)amino butoxycarbonyl groups, $CONR^5R^6$ wherein $R^5$ is hydrogen, alkyl having 1 to 6 carbon atoms, aralkyl and $R^6$ is alkyl, aryl, or aralkyl or N, $R^5$, and $R^6$ taken together form a cyclic amine, or when A is $NR^4$ or $CH_2NR^4$ then B is a naturally occurring α-amino acid moiety joined by an amide bond or B joins with $R^4$ and the nitrogen to form a four to seven membered heterocyclic ring, provided that when Z is a fused cyclohexyl ring and $R^4$ is hydrogen then B is not hydrogen;

(ii) when A is CN then B is not present and Z is not a fused cyclohexyl ring;

(iii) when A is tetrazole then B is hydrogen or alkyl having 1 to 6 carbon atoms; and (iv) when A is CO then B is hydroxy, alkoxy, aralkoxy, alkyl having 1 to 6 carbon atoms, aralkyl, $NR^7R^8$ wherein $R^7$ is hydrogen, alkyl having 1 to 6 carbon atoms, aralkyl and $R^8$ is alkyl, aryl, aralkyl or N, $R^7$, and $R^8$ taken together form a cyclic amine.

2. A compound according to claim 1, wherein Z is a cyclopentyl fused ring or a cyclohexyl fused ring, $R^1$ is hydrogen, X and Y are independently hydrogen, nitro or halogen, A is O, $NR^4$, $CH_2NR^4$, CN, tetrazole or CO, and $R^4$ is hydrogen, methyl, ethyl or joined with B to form a heterocyclic ring.

3. A compound according to claim 2, wherein B is hydrogen, alkyl, aryl, aralkyl, heterocyclic, alkylheterocyclic, alkylcarbonyl, cycloalkylcarbonyl, arylcarbonyl, aralykylcarbonyl, heterocyclic-carbonyl, alkylheterocyclic-carbonyl, or alkoxy.

4. A compound according to claim 3, wherein A is O, $NR^4$ or CO and X is nitro.

5. A compound according to claim 4, wherein Z is a cyclohexyl fused ring, A is O, $NR^4$ or $CH_2NR^4$ and B is methyl, acetyl 6. A compound according to claim 4, wherein Z is a cyclopentyl fused ring, A is $NR^4$ or $CH_2NR^4$, and B is methyl, ethyl, acetyl,

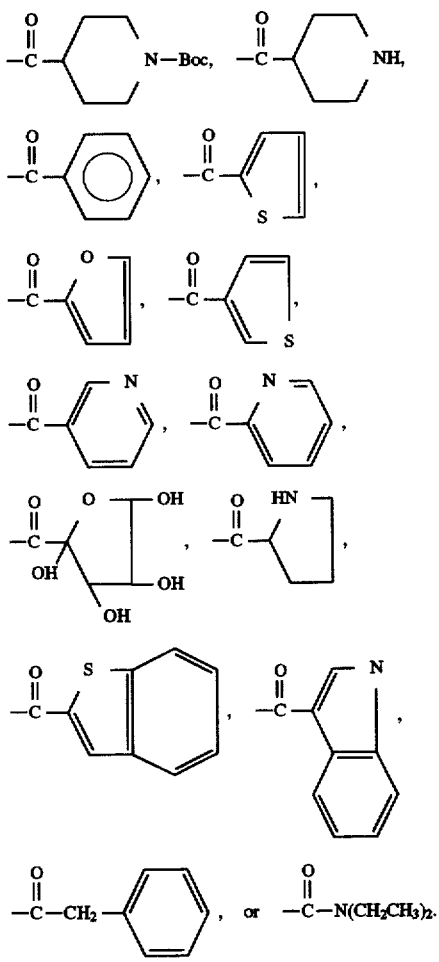

7. A compound according to claim 2, wherein the heterocyclic ring is a pyrrolidine ring or a piperidine ring.

8. A compound selected from the group consisting of:
9-benzyloxy-6-bromo-1,4,7,8,9,10-hexahydrobenzo[f]quinoxaline-2,3-dione;
6-bromo-9-hydroxy-1,4,7,8,9,10-hexahydro-benzo[f]quinoxaline-2,3-dione;
piperidine-4-carboxylic acid (6-nitro-2,3-dioxo-1,2,3,4,7,8,9,10-octahydro-benzo[f]quinoxalin-9-yl) amide;
N-(6-nitro-2,3-dioxo-1,2,3,4,7,8,9,10-octahydrobenzo[f]quinoxalin-9-yl)-acetamide;
9-benzylamino-6-bromo-1,4,7,8,9,10-hexahydrobenzo[f]quinoxaline-2,3-dione;
N-(5-bromo-2,3-dioxo-2,3,4,7,8,9-hexahydro-1H-cyclopenta[f]-quinoxalin-8-yl)-acetamide;
N-(5-bromo-6-nitro-2,3-dioxo-2,3,4,7,8,9-hexahydro-1H-cyclopenta[f]quinoxalin-8-yl)-acetamide;
N-(2,3-dioxo-2,3,4,7,8,9-hexahydro-1H-cyclopenta[f]quinoxalin-8-yl)-acetamide;
N-[6-nitro-2,3-dioxo-2,3,4,7,8,9-hexahydro-1H-cyclopenta[f]quinoxalin-8-yl)-acetamide;
8-amino-4,7,8,9-tetrahydro-1H-cyclopenta[f]quinoxaline-2,3-dione hydrochloride;
4-(2,3,-dioxo-2,3,4,7,8,9-hexahydro-1H-cyclopenta[f]-quinoxalin-8-ylcarbamoyl)-piperidine-1-carboxylic acid tert-butyl ester;
4-(6-nitro-2,3, -dioxo-2,3,4,7,8,9-hexahydro-1H cyclopenta[f]quinoxalin-8-yl-carbamoyl)-piperidine hydrochloride;
N-(6-nitro-2,3-dioxo-1,2,3,4,7,8,9,10-octahydrobenzo[f]quinoxalin-9-yl)-benzamide;
N-(6-nitro-2,3-dioxo-1,2,3,4,7,8,9,10-octahydrobenzo[f]quinoxalin-9-yl) cyclohexylamide;
8-amino-6-nitro-4,7,8,9-tetrahydro-1H-cyclopenta[f]-quinoxaline-2,3-dione hydrochloride;
N-(6-nitro-2,3-dioxo-4,7,8,9-tetrahydro-1H cyclopenta[f]quinoxalin-8-yl]-benzamide;
4-(6-nitro-2,3-dioxo-1,2,3,4,7,8,9,10-octahydrobenzo[f]quinoxalin-9-ylcarbamoyl)-piperidine hydrochloride;
2-(6-nitro-2,3-dioxo-1,2,3,4,7,8,9,10-octahydrobenzo[f]quinoxalin-9-ylcarbamoyl)ethyl-(4-hydroxy) benzene;
N-phenyl-N'-(6-nitro-2,3-dioxo-1,2,3,4,7,8,9,10-octahydrobenzo[f]quinoxalin-9-yl)-urea;
thiophene-2-carboxylic acid (6-nitro-2,3-dioxo-2,3,4,7,8,9-hexahydro-1H-cyclopenta[f]quinoxaline-8-yl)-amide;
furan-2-carboxylic acid (6-nitro-2,3-dioxo-2,3,4,7,8,9-hexahydro-1H -cyclopenta[f]quinoxalin-8-yl)-amide;
thiophene-3-carboxylic acid (6-nitro-2,3-dioxo-2,3,4,7,8,9-hexahydro-1H-cyclopenta[f]quinoxalin-8-yl)amide;
N-(6-nitro-2,3-dioxo-2,3,4,7,8,9-hexahydro-1H-cyclopenta[f]quinoxalin-8-yl)-nicotinamide;
pyridine-2-carboxylic acid (6-nitro-2,3-dioxo-2,3,4,7,8,9-hexahydro-1H-cyclopenta[f]quinoxalin-8-yl)-amide;
pyrrolidine-2-carboxylic acid (6-nitro-2,3-dioxo-2,3,4,7,8,9-hexahydro-1H-cyclopenta[f]quinoxalin-8-yl)-amide;
benzo[b]thiophene-2-carboxylic acid (6-nitro-2,3,-dioxo-2,3,4,7,8,9-hexahydro-1H-cyclopenta[f]quinoxalin-8-yl)-amide;
2-(1H-indol -3-yl)-N-(6-nitro-2,3-dioxo-2,3,4,7,8,9-hexahydro-1H -cyclopenta[f]quinoxalin-8-yl)-acetamide;
6-nitro-2,3,-dioxo-2,3,4,7,8,9-hexahydro-1H-cyclopenta[f]quinoxaline-8-carboxylic acid;
6-nitro-2,3,-dioxo-2,3,4,7,8,9-hexahydro-1H-cyclopenta[f]quinoxaline-8-carboxylic acid phenylamide;
6-nitro-9-pyrrolidin-1-yl-1,4,7,8,9,10-hexahydrobenzo[f]quinoxaline-2,3-dione;
6-nitro-8-pyrrolidin-1-yl-4,7,8,9-tetrahydro-1H-cyclopenta[f]quinoxaline-2,3-dione;
6-nitro-8-piperidin-1-yl-4,7,8,9-tetrahydro-1H-cyclopenta[f]quinoxaline-2,3-dione;
2-[2-hydroxy-phenyl)-N-(6-nitro-2,3-dioxo-2,3,4,7,8,9-hexahydro-1H-cyclopenta[f]quinoxalin-8-yl)-acetamide;
2-(2-hydroxy-phenyl)-N-(6-nitro-2,3-dioxo-1,4,7,8,9,10-hexahydro-benzo[f]quinoxalin-9-yl)-acetamide;
6-nitro-8-(pyridin-2-ylamino)-4,7,8,9-tetrahydro-1H-cyclopenta[f]quinoxaline-2,3-dione;
6-nitro-9-(pyridin-2-ylamino)-1,4,7,8,9,10-hexahydro-benzo[f]quinoxaline-2,3-dione;
2-hydroxy-benzoic acid 6-nitro-2,3-dioxo-2,3,4,7,8,9-hexahydro-1H -cyclopenta[f]quinoxalin-8-yl ester;
2-hydroxy-benzoic acid 6-nitro-2,3-dioxo-1,4,7,8,9,10-hexahydro-benzo[f]quinoxalin-9-yl ester;
2-hydroxy-N-(6-nitro-2,3-dioxo-2,3,4,7,8,9-hexahydro-1H-cyclopenta[f]quinoxalin-8-yl)-benzamide;
2-hydroxy -N-(6-nitro-2,3-dioxo-1,4,7,8,9,10-hexahydrobenzo[f]quinoxalin-9-yl)-benzamide; and
a pharmaceutically acceptable salt thereof.

9. A pharmaceutical composition comprising a pharmaceutically acceptable carrier or diluent and at least one compound of claim 1.

10. A method for treating convulsions which comprises administering to a human at least one compound of claim 1 in unit dosage form.

11. A method for treating anxiety which comprises administering at least one compound of claim 1 in unit dosage form.

12. A method for treating cerebral hypoxic/ischemia which comprises administering at least one compound of claim 1 in unit dosage form.

13. A method for treating Parkinsonism which comprises administering at least one compound of claim 1 in unit dosage form.

* * * * *